(12) United States Patent
Somanath et al.

(10) Patent No.: US 12,018,032 B2
(45) Date of Patent: Jun. 25, 2024

(54) CRYSTALLINE FORMS OF N-[4-[4-(4-MORPHOLINYL)-7H-PYRROLO[2,3-D]PYRIMIDIN-6-YL]PHENYL]-4-[[3(R)-[(1-OXO-2-PROPEN-1-YL)AMINO]-1-PIPERIDINYL]METHYL]-2-PYRIDINE-CARBOXAMIDE AS AN IRREVERSIBLE INHIBITOR OF MENIN-MLL INTERACTION

(71) Applicant: BIOMEA FUSION, INC., Redwood City, CA (US)

(72) Inventors: Priyanka Somanath, Dublin, CA (US); Daniel Lu, San Jose, CA (US); Taisei Kinoshita, San Jose, CA (US); Brian Law, San Jose, CA (US); Thomas Butler, Redwood City, CA (US); James T. Palmer, Warrandyte (AU); Nan-Horng Lin, Vernon Hills, IL (US); Heow Meng Tan, Cupertino, CA (US); Angelina Sau Man Wong, Redwood City, CA (US); Siyi Jiang, Shanghai (CN); Hongyan He, Shanghai (CN)

(73) Assignee: BIOMEA FUSION, INC., Redwood City, CA (US)

( * ) Notice: Subject to any disclaimer, the term of this patent is extended or adjusted under 35 U.S.C. 154(b) by 0 days.

(21) Appl. No.: 17/885,213

(22) Filed: Aug. 10, 2022

(65) Prior Publication Data
US 2023/0086137 A1  Mar. 23, 2023

Related U.S. Application Data

(60) Provisional application No. 63/235,662, filed on Aug. 20, 2021, provisional application No. 63/279,053, filed on Nov. 12, 2021, provisional application No. 63/310,076, filed on Feb. 14, 2022.

(51) Int. Cl.
| | |
|---|---|
| *A61K 31/4427* | (2006.01) |
| *A61K 9/00* | (2006.01) |
| *A61K 9/48* | (2006.01) |
| *A61P 35/00* | (2006.01) |
| *A61P 35/02* | (2006.01) |
| *C07D 401/14* | (2006.01) |
| *C07D 487/04* | (2006.01) |

(52) U.S. Cl.
CPC .......... *C07D 487/04* (2013.01); *A61K 9/0053* (2013.01); *A61K 9/4825* (2013.01); *A61K 9/485* (2013.01); *A61K 9/4858* (2013.01); *A61K 9/4866* (2013.01); *A61P 35/00* (2018.01); *A61P 35/02* (2018.01); *C07B 2200/13* (2013.01)

(58) Field of Classification Search
CPC .............................. A61K 31/4427; C07D 401/14
USPC ...................................... 514/338; 546/268.1
See application file for complete search history.

(56) References Cited

U.S. PATENT DOCUMENTS

| | | | |
|---|---|---|---|
| 7,034,049 B1 | 4/2006 | Pevarello et al. | |
| 7,514,448 B2 | 4/2009 | Green et al. | |
| 11,084,825 B2 | 8/2021 | Butler et al. | |
| 11,174,263 B2 | 11/2021 | Butler et al. | |
| 11,702,421 B2 | 7/2023 | Butler et al. | |
| 2002/0019526 A1 | 2/2002 | Blumenkopf et al. | |
| 2005/0209297 A1 | 9/2005 | Sanner et al. | |
| 2005/0282814 A1 | 12/2005 | Wrasidlo et al. | |
| 2006/0293336 A1 | 12/2006 | Green et al. | |
| 2009/0163545 A1 | 6/2009 | Goldfarb | |
| 2009/0215742 A1 | 8/2009 | Funk et al. | |
| 2010/0168084 A1 | 7/2010 | Huber et al. | |
| 2010/0256171 A1 | 10/2010 | Taunton et al. | |
| 2012/0263708 A1 | 10/2012 | Bader et al. | |
| 2013/0143926 A1 | 6/2013 | Donald et al. | |
| 2015/0376189 A1 | 12/2015 | Zorn et al. | |
| 2016/0185785 A1 | 6/2016 | Loannidis et al. | |
| 2018/0244654 A1 | 8/2018 | Schlitz et al. | |
| 2020/0255434 A1 | 8/2020 | Butler et al. | |
| 2022/0024936 A1 | 1/2022 | Butler et al. | |

(Continued)

FOREIGN PATENT DOCUMENTS

| | | |
|---|---|---|
| CN | 102266341 A | 12/2011 |
| CN | 105997965 A | 10/2016 |

(Continued)

OTHER PUBLICATIONS

International Search Report and Written Opinion for International Application PCT/US2019/069155, 10 pages, dated Apr. 24, 2020.

(Continued)

*Primary Examiner* — Douglas M Willis
(74) *Attorney, Agent, or Firm* — Squire Patton Boggs (US) LLP

(57) ABSTRACT

Described herein is N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (I)

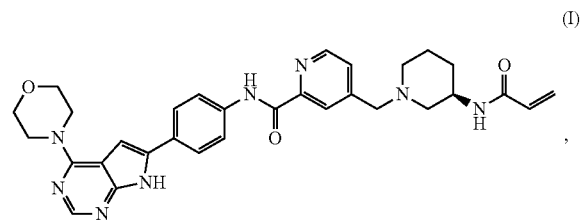

including crystalline forms, solvates, and pharmaceutically acceptable salts thereof. Also disclosed are pharmaceutical compositions that include compound (I), as well as methods of using compound (I), alone or in combination with other therapeutic agents, for the treatment of autoimmune diseases or conditions, heteroimmune diseases or conditions, cancer, including lymphoma, and inflammatory diseases or conditions.

19 Claims, 38 Drawing Sheets

(56) References Cited

U.S. PATENT DOCUMENTS

| | | |
|---|---|---|
| 2022/0169627 A1 | 6/2022 | Butler et al. |
| 2023/0120115 A1 | 4/2023 | Butler et al. |
| 2023/0150991 A1 | 5/2023 | Sands et al. |

FOREIGN PATENT DOCUMENTS

| | | |
|---|---|---|
| CN | 107176951 A | 9/2017 |
| CN | 108727295 A | 11/2018 |
| DE | 10219294 A1 | 11/2003 |
| DE | 102004048877 A1 | 4/2006 |
| EP | 2 924 039 A1 | 9/2015 |
| FR | 2878849 A1 | 6/2006 |
| JP | H09157392 A | 6/1997 |
| JP | 2014/166961 A | 9/2014 |
| JP | 2015/183128 A | 10/2015 |
| KR | 2014/125117 A | 10/2014 |
| RU | 2364597 C1 | 8/2009 |
| WO | WO 2001/012189 A1 | 2/2001 |
| WO | WO 2002/018346 A1 | 3/2002 |
| WO | WO 2002/048114 A1 | 6/2002 |
| WO | WO 2002/083648 A1 | 10/2002 |
| WO | WO 2003/000688 A1 | 1/2003 |
| WO | WO 2003/035065 A1 | 5/2003 |
| WO | WO 2003/035644 A1 | 5/2003 |
| WO | WO 2004/089415 A2 | 10/2004 |
| WO | WO 2004/089416 A2 | 10/2004 |
| WO | WO 2004/089470 A2 | 10/2004 |
| WO | WO 2005/002552 A2 | 1/2005 |
| WO | WO 2005/030206 A1 | 4/2005 |
| WO | WO 2005/041879 A2 | 5/2005 |
| WO | WO 2005/042495 A1 | 5/2005 |
| WO | WO 2005/095400 A1 | 10/2005 |
| WO | WO 2005/103050 A2 | 11/2005 |
| WO | WO 2005/121147 A1 | 12/2005 |
| WO | WO 2006/040279 A1 | 4/2006 |
| WO | WO 2006/058120 A1 | 6/2006 |
| WO | WO 2006/061493 A1 | 6/2006 |
| WO | WO 2006/091671 A1 | 8/2006 |
| WO | WO 2006/108640 A1 | 10/2006 |
| WO | WO 2006/123061 A2 | 11/2006 |
| WO | WO 2007/019416 A1 | 1/2007 |
| WO | WO 2007/017083 A1 | 2/2007 |
| WO | WO 2007/019344 A1 | 2/2007 |
| WO | WO 2007/019345 A1 | 2/2007 |
| WO | WO 2007/019346 A1 | 2/2007 |
| WO | WO 2007/019417 A1 | 2/2007 |
| WO | WO 2007/064902 A2 | 6/2007 |
| WO | WO 2007/064931 A2 | 6/2007 |
| WO | WO 2007/091106 A2 | 8/2007 |
| WO | WO 2007/117465 A2 | 10/2007 |
| WO | WO 2008/075196 A1 | 6/2008 |
| WO | WO 2009/019504 A1 | 2/2009 |
| WO | WO 2009/077956 A2 | 6/2009 |
| WO | WO 2010/011762 A1 | 1/2010 |
| WO | WO 2010/129620 A1 | 11/2010 |
| WO | WO 2012/135799 A1 | 10/2012 |
| WO | WO 2012/176763 A1 | 12/2012 |
| WO | WO 2004/030635 A2 | 4/2014 |
| WO | WO 2014/118135 A1 | 8/2014 |
| WO | WO 2015/000959 A1 | 1/2015 |
| WO | WO 2015/040425 A1 | 3/2015 |
| WO | WO 2015/144926 A1 | 10/2015 |
| WO | WO 2015/0195228 A1 | 12/2015 |
| WO | WO 2016/051193 A1 | 4/2016 |
| WO | WO 2016/148114 A1 | 9/2016 |
| WO | WO 2016/197078 A1 | 12/2016 |
| WO | WO 2016/202758 A1 | 12/2016 |
| WO | WO 2017/075367 A1 | 5/2017 |
| WO | WO 2017/152874 A1 | 9/2017 |
| WO | WO 2017/161002 A1 | 9/2017 |
| WO | WO 2017/161028 A1 | 9/2017 |
| WO | WO 2017/161280 A1 | 9/2017 |
| WO | WO 2017/0192543 A1 | 11/2017 |
| WO | WO 2017/214367 A1 | 12/2017 |
| WO | WO 2018/106818 A1 | 6/2018 |
| WO | WO 2018/132372 A1 | 7/2018 |
| WO | WO 2018/175537 A1 | 9/2018 |
| WO | WO 2018/183857 A1 | 10/2018 |
| WO | WO 2019/192962 A1 | 10/2019 |
| WO | WO 2020/142557 A1 | 7/2020 |
| WO | WO 2020/142559 A1 | 7/2020 |
| WO | WO 2022/133064 A1 | 6/2022 |
| WO | WO 2023/018825 A1 | 2/2023 |
| WO | WO 2023/022912 A1 | 2/2023 |

OTHER PUBLICATIONS

International Search Report and Written Opinion for International Application PCT/US2019/069157, 10 pages, dated Apr. 21, 2020.
S. Xu et al., "Design of the First-in-Class, Highly Potent Irreversible Inhibitor Targeting the Menin-MLL Protein-Protein Interaction", Angewandte Chemie International Ed. 57(6), 1601-1605 (2017).
Winters and Bernt, "MLL-Reaarranged Leukemias an Update on Science and Clinical Approaches", 21 pages, Front. Pediatr. 5, 4 (2017).
Borisa et al., "3D-QSAR (CoMFA, CoMFA-RG, CoMSIA) and molecular docking study of thienopyrimidine and thienopyridine derivatives to explore structural requirements for aurora-B kinase inhibition", European Journal of Pharmaceutical Sciences (2015), 13 pages, 79, 1-12.
Dorwald, F. Zaragoza, Side Reactions in organic Syntehsis: A guide to Successful Synthesis Design, Weinheim: Wiley-VCH Verlag Gmbh & Co. KGaA 2005 Preface.
European Search Report for EP Application No. 19906970.9, 56 pages, dated Sep. 15, 2022.
Hackam, et al., JAMA 296(14): 1731-1732 (2006).
Jordan, V.C. Nature Reviews: Drug Discovery 2: 2003:205.
Pevarello et al., 3-Aminopyrazole Inhibitors of CDK2/Cyclin A as Antitumor Agents. 2. Lead Optimization:, Journal Med. Chem. 2005, 13 pages, 48:2944-2956.
Pevarello et al., 3-Aminopyrazole Inhibitors of CDK2/Cyclin A as Antitumor Agents. 2. Lead Optimization:, Additions and Corrections, Journal Med. Chem. 2005, 13 pages, 45:5058.
Stella, Valentino "Prodrugs: Some Thoughts and Current Issues", Journal of Pharmaceutical Sciences, 2010, 99(12) pp. 4755-4765.
International Search Report and Written Opinion for International Application No. PCT/US2021/063761, 16 pages, dated Mar. 16, 2022.
CAS SciFinder; Returned Reference Search Report for References of US20200223853; 15 pages, dated Jun. 30, 2021.
Butler Thomas et al.: "Oral Long-Acting Menin Inhibitor, BMF-219, Normalizes Type 2Diabetes Mellitus in Two Rat Models", ADA 2022, Jun. 1, 2022 (Jun. 1, 2022), XP093001069, Retrieved from the Internet: URL:https:// biomeafusion.com/wp-content/uploads/2022/06/ADA-Poster-2022_Regular-Abstract_052622_Final2.pdf.
International Search Report and Written Opinion for International Application No. PCT/US2022/039990, 13 pages, dated Dec. 2, 2022.
International Search Report and Written Opinion for International Application No. PCT/US2022/039941, 20 pages, dated Jan. 23, 2023.
Jian et al.: "Menin-regulated Pbk controls high fat diet-induced compensatory beta cell proliferation", EMBO Molecular Medicine, vol. 13, No. 5, Apr. 6, 2021 (Apr. 6, 2021), XP093001179, US ISSN: 1757-4676, DOI: 10.15252/emmm.202013524 Retrieved from the Internet: URL:https://onlinelibrary.wiley.com/doi/full-XML/10.15252/emmm.202013524.
Somanath Priyanka et al.: "Oral Menin Inhibitor, BMF-219, displays a significant and durable reduction in HbA1c in a Type 2 Diabetes Mellitus Rat Model", Jun. 1, 2022 (Jun. 1, 2022), XP093001072, Retrieved from the Internet: URL:https://biomeafusion.com/wp-content/uploads/2022/06/ADA-Poster-2022_Late-Breaking_052622_Final.pdf.
Yang et al. "Reversal of preexisting hyperglycemia in diabetic mice by acute deletion of the Men1 gene", Proceedings of the National Academy of Sciences, vol. 107, No. 47, Nov. 8, 2010 (Nov. 8, 2010), pp. 20358-20363, XP093000810, ISSN: 0027-8424, DOI:

(56) References Cited

OTHER PUBLICATIONS 10.1073/pnas. 1012257107 Retrieved from the Internet: URL:https://www.ncbi.nlm.nih.gov/pmc/articles/PMC2996686/pdf/pnas.201012257.

Figure 1A XRPD Pattern of Free Form Pattern A (Compound A, Form A)
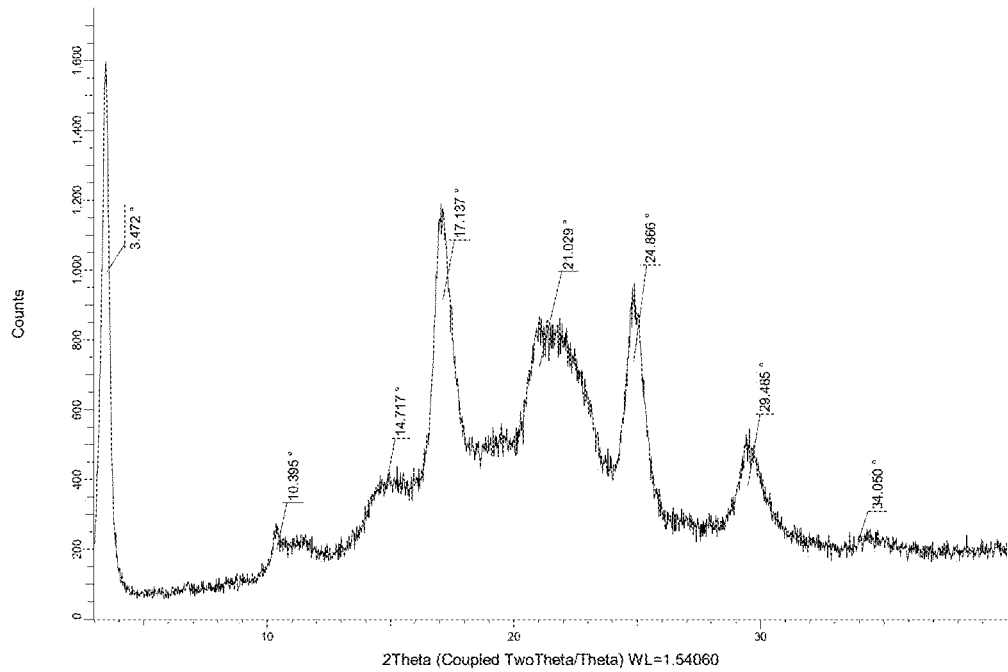

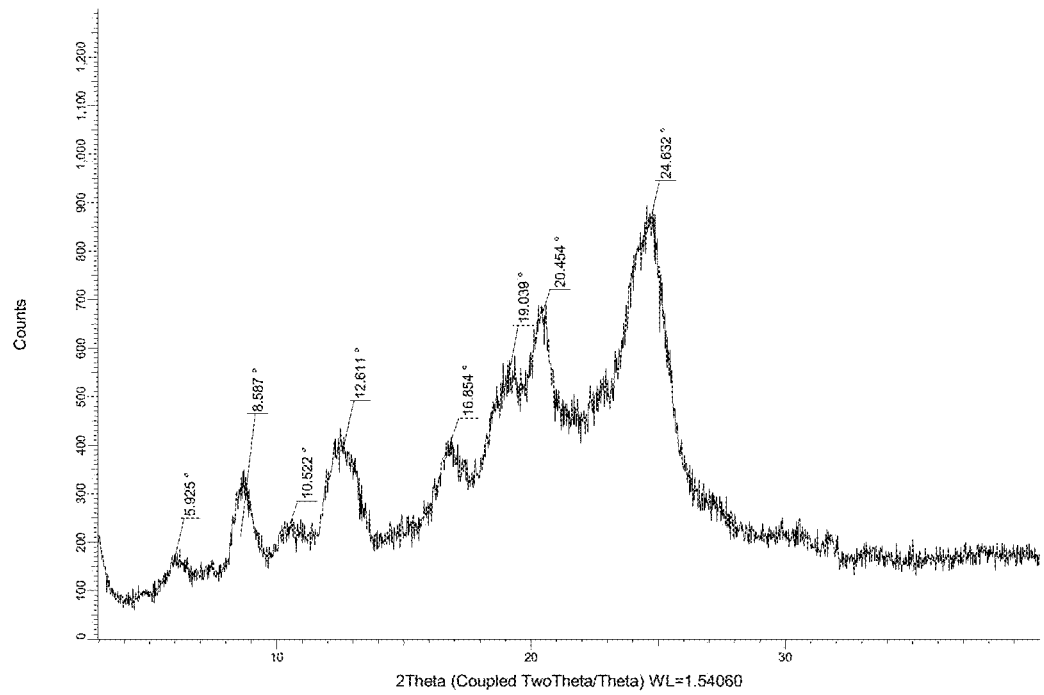
Figure 2A XRPD Pattern of Free Form Pattern B (Compound A, Form B)

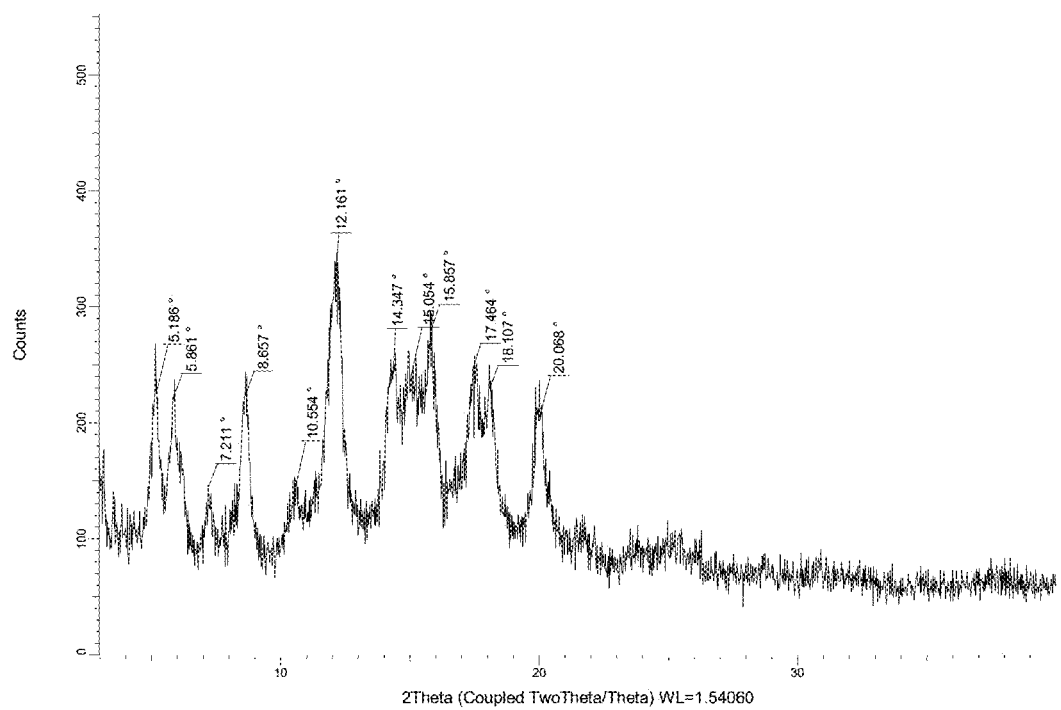
Figure 3A XRPD Pattern of Free Form Pattern C (Compound A, Form C)

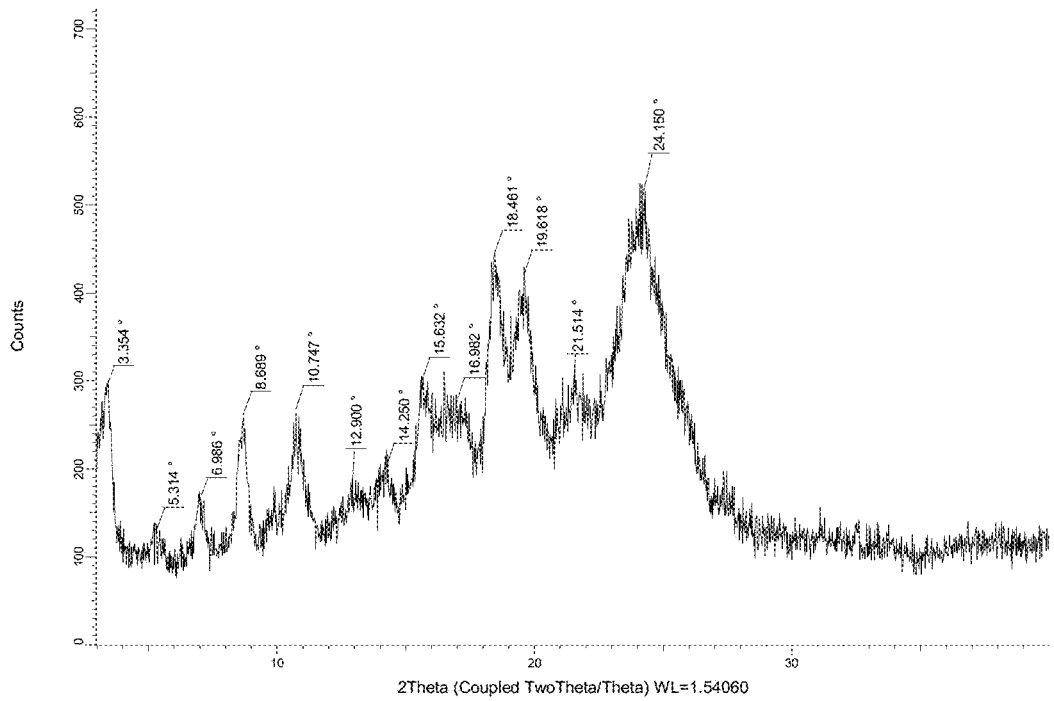
Figure 4A XRPD Pattern of Free Form Pattern D (Compound A, Form D)

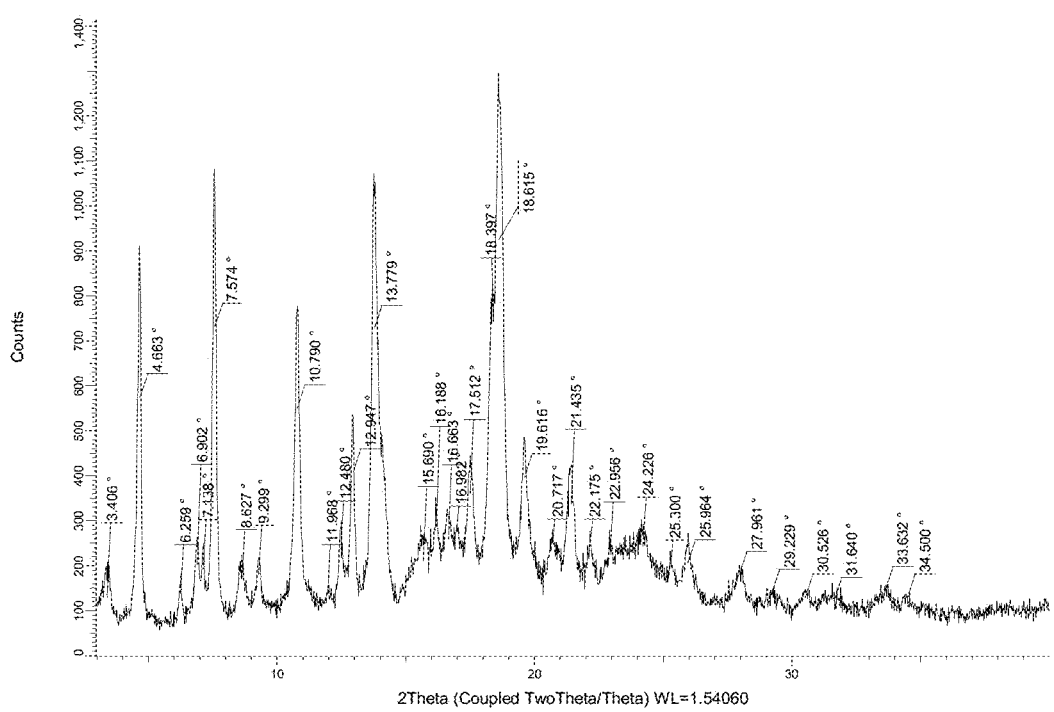
Figure 5A XRPD Pattern of Free Form Pattern E (Compound A, Form E)

Figure 6A XRPD Pattern of Free Form Pattern F (Compound A, Form F)
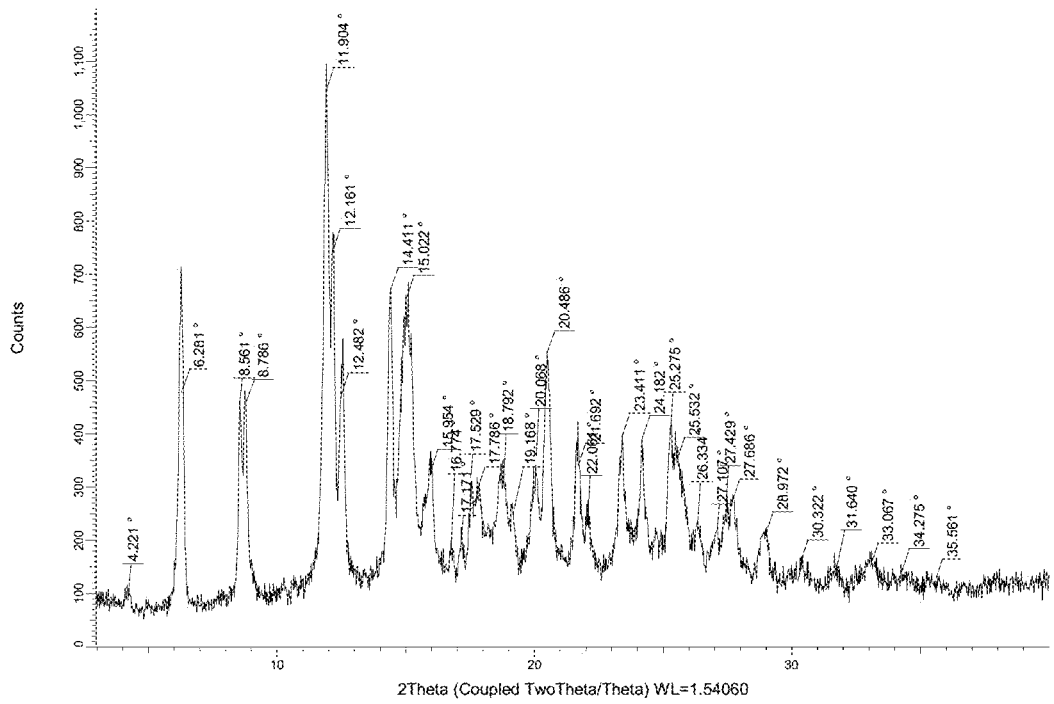

Figure 7A XRPD Pattern of Free Form Pattern G (Compound A, Form G)
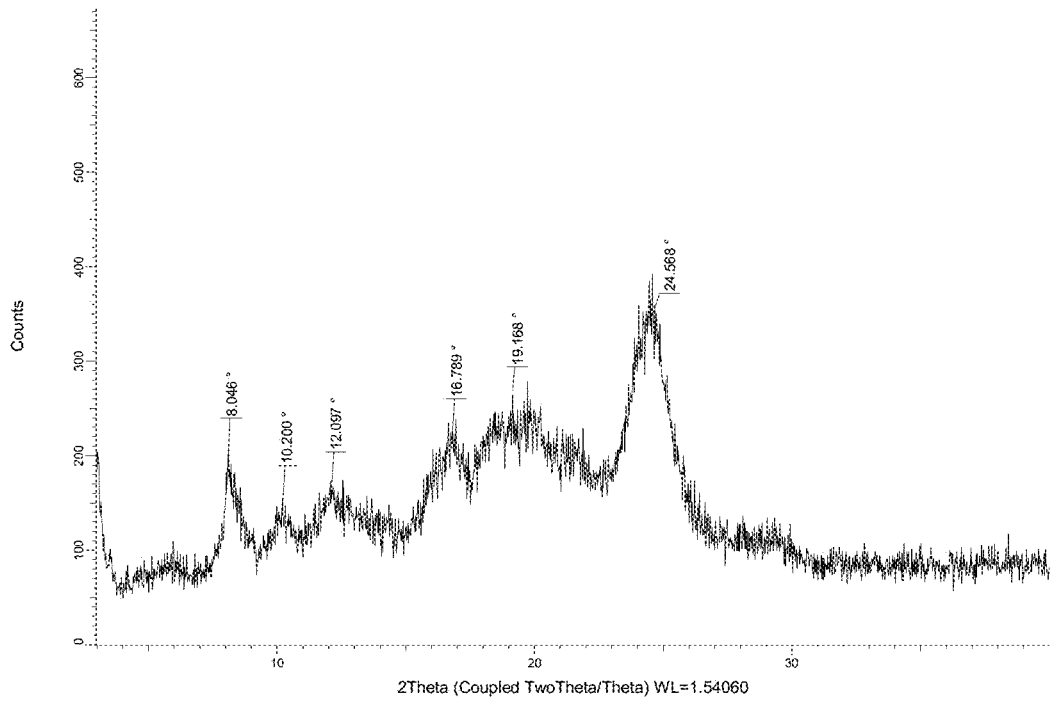

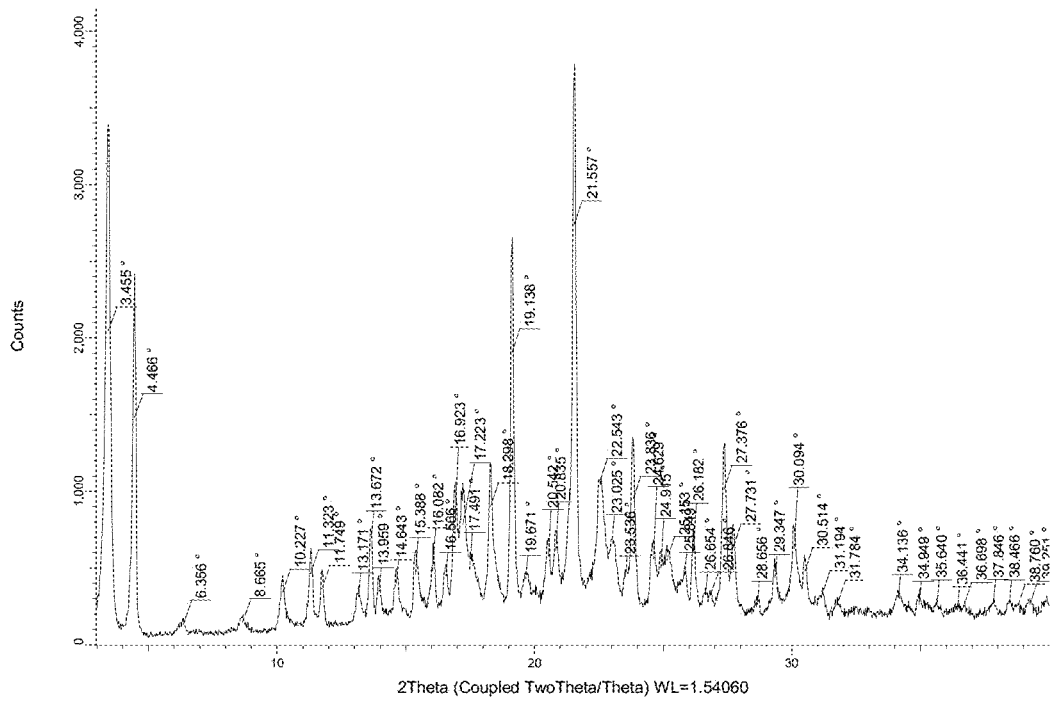
Figure 8A XRPD Pattern of Free Form Pattern J (Compound A, Form J)

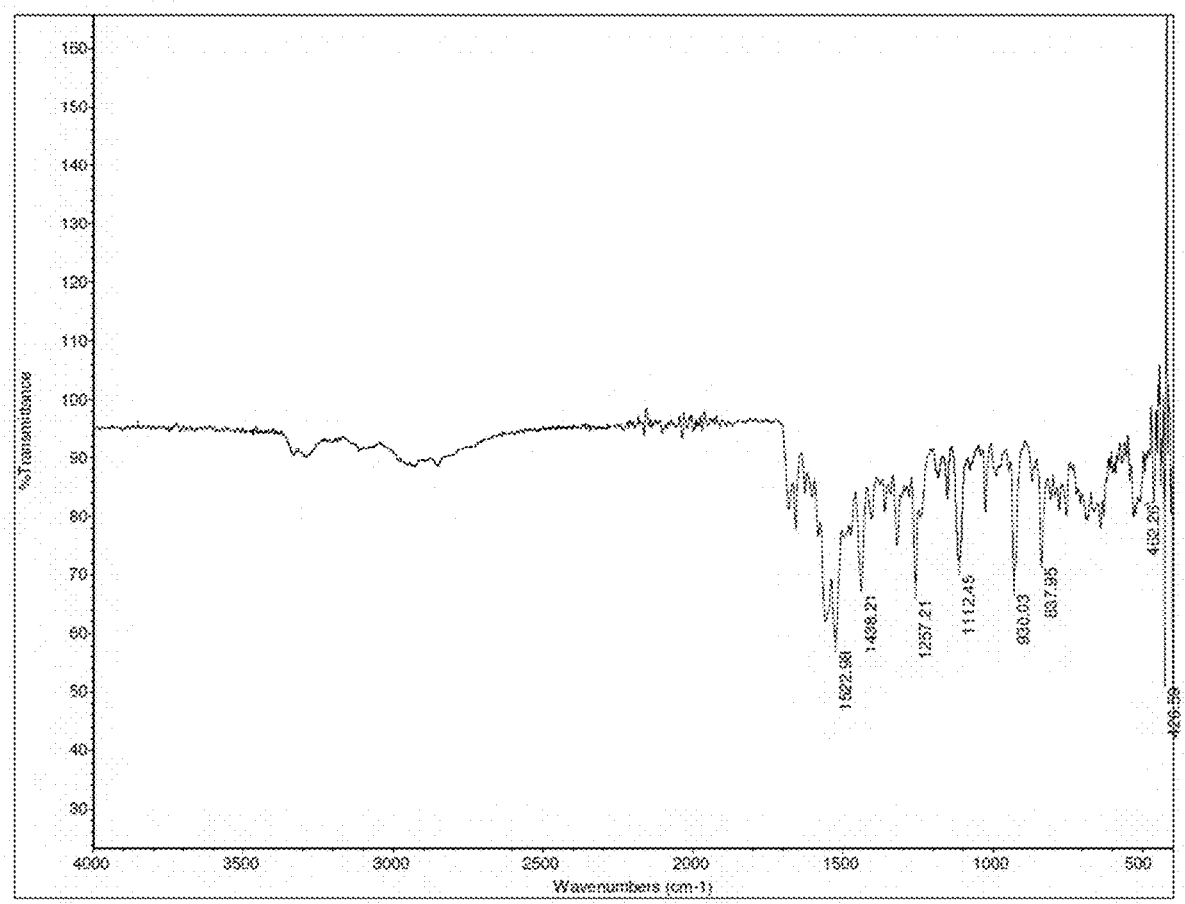
Figure 9A IR Spectra of Free Form Pattern D (Compound A, Form D)

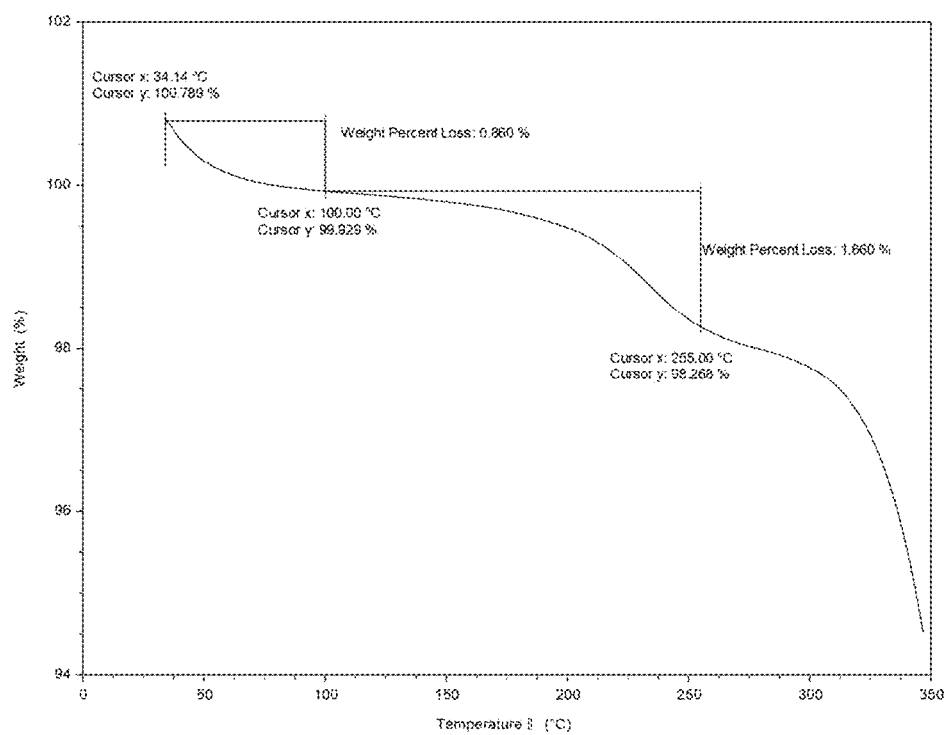
Fig. 10 TGA Thermogram of Free Form Pattern D

Fig. 11 DSC Thermogram of Free Form Pattern D
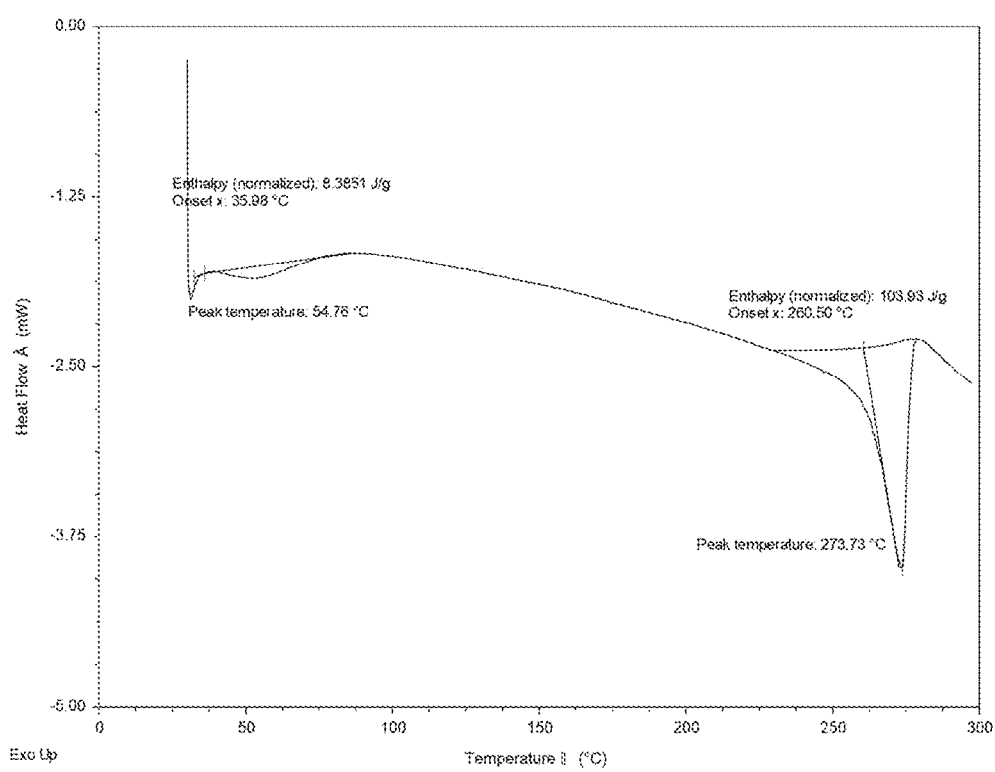

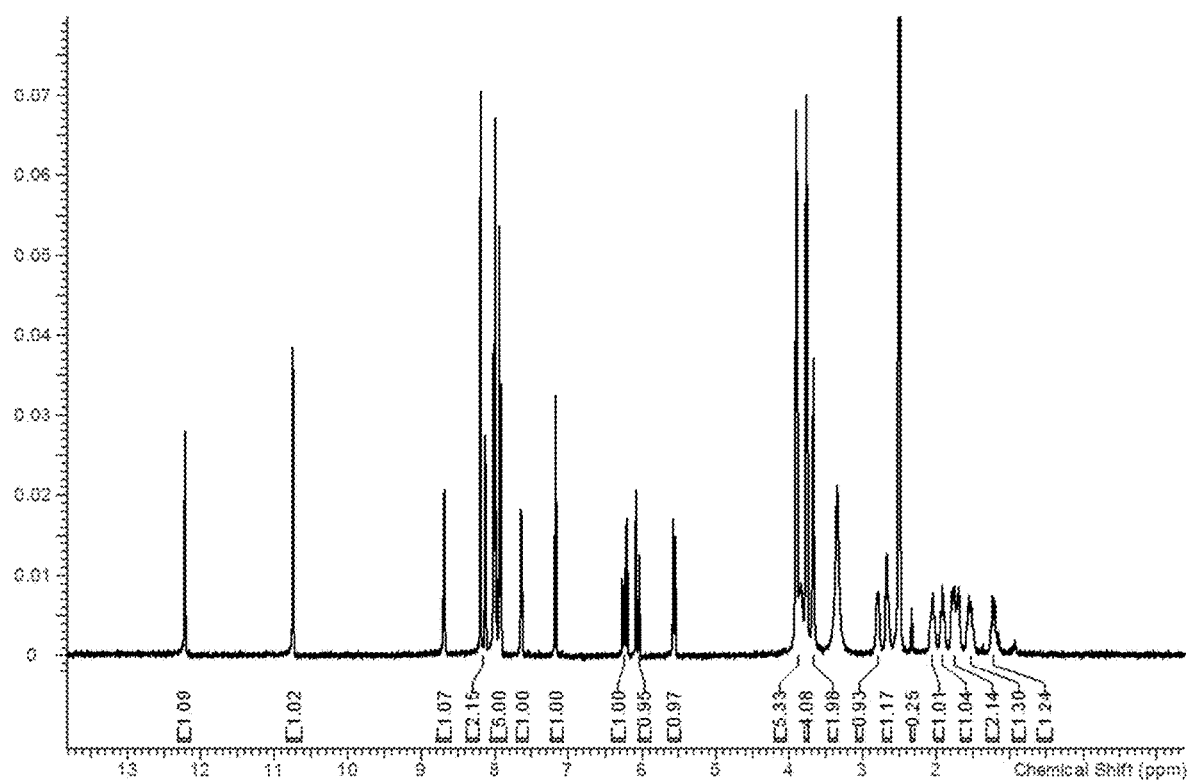
Fig. 12 $^1$H NMR Spectrum of Free Form Pattern D

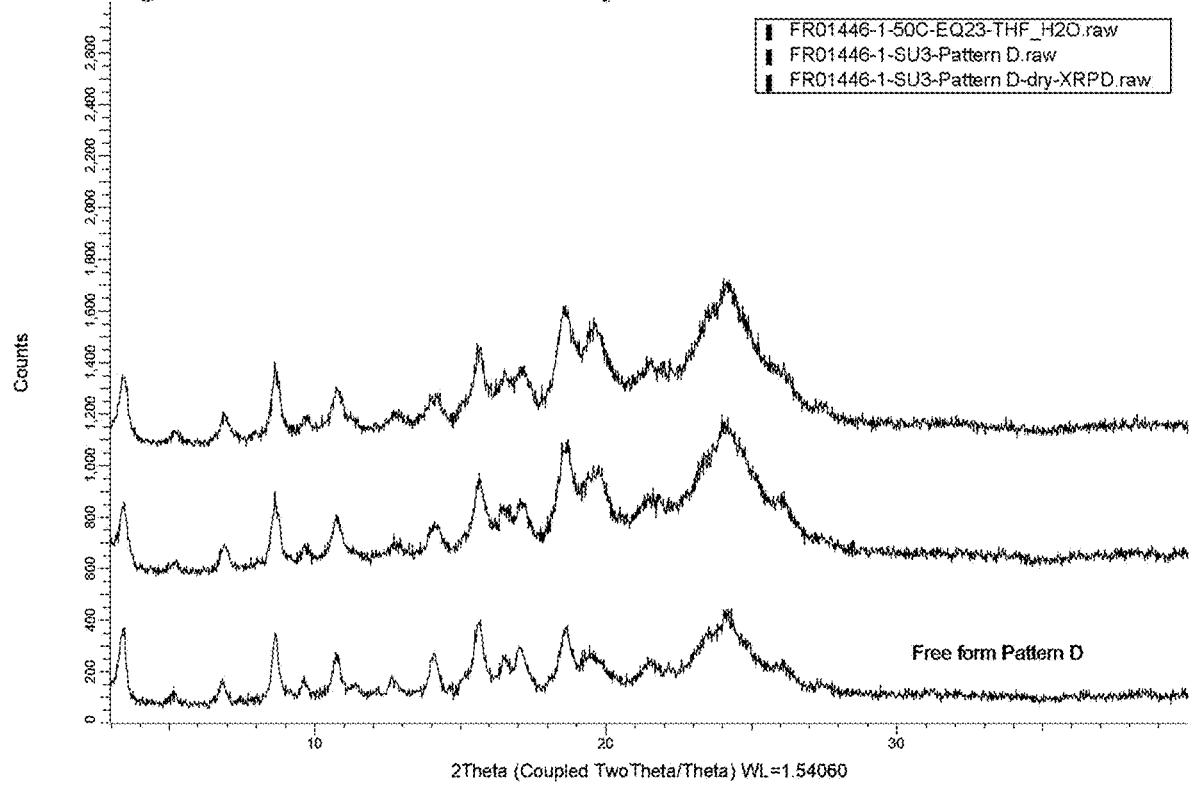
Fig. 13 XRPD Pattern of Pattern D, Sample ID FR01446-1-SU3-Pattern D

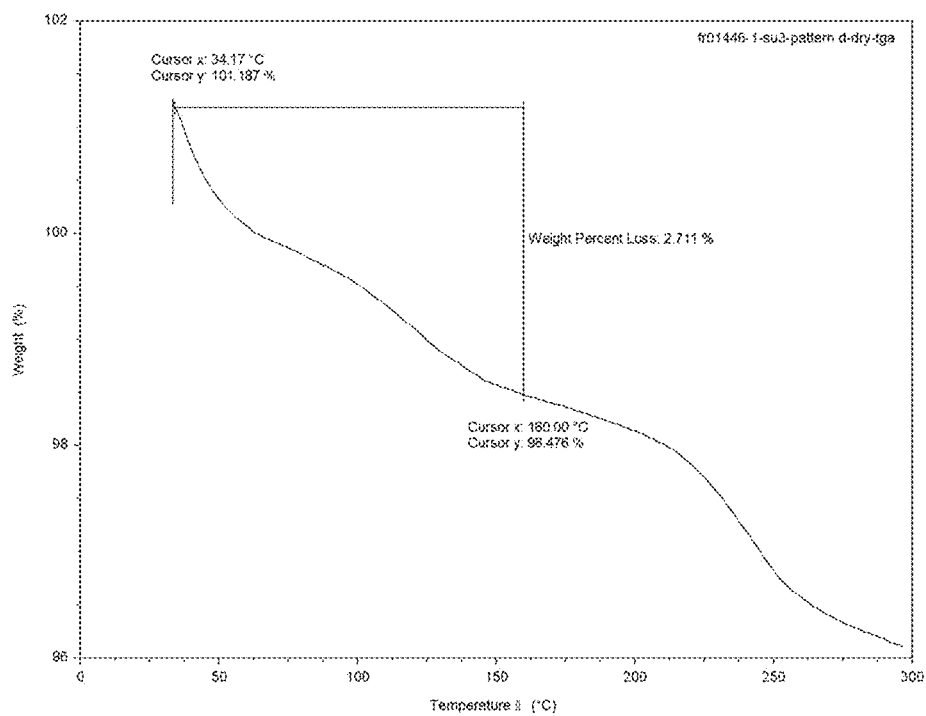
Figure 14 TGA Thermogram of Pattern D After Being Dried at 50°C for 3 h, Sample ID FR01446-1-SU3-Pattern D-dry Fig. 15 DSC Thermogram of Pattern D After Being Dried at 50°C for 3 h, Sample ID FR01446-1-SU3-Pattern D-dry
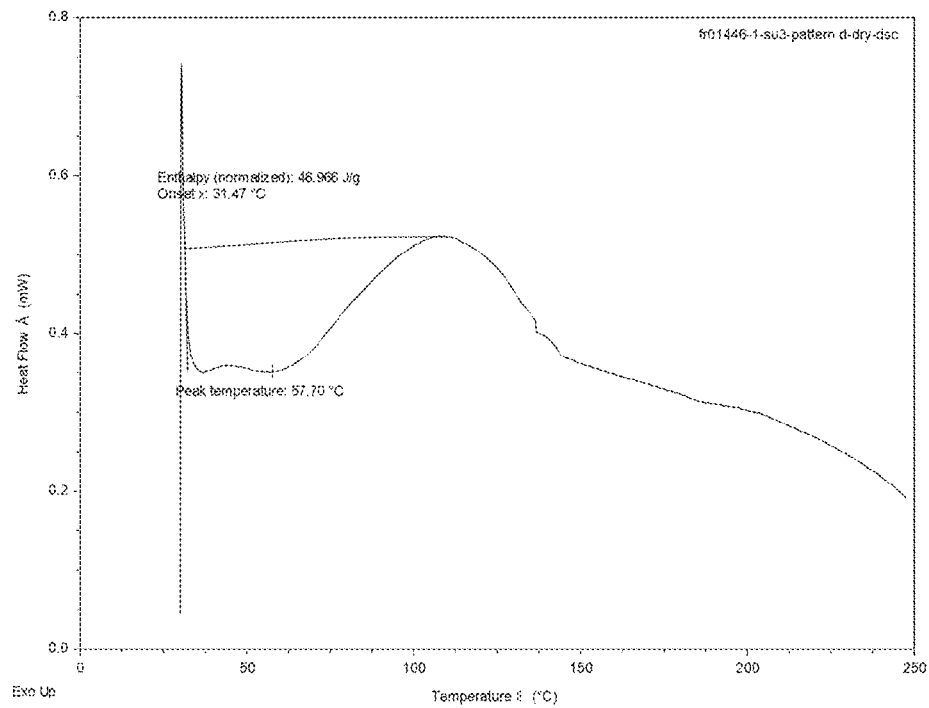

Fig. 16  ¹H NMR Spectrum of Pattern D After Being Dried at 50°C for 3 h, Sample ID FR01446-1-SU3-Pattern D-dry
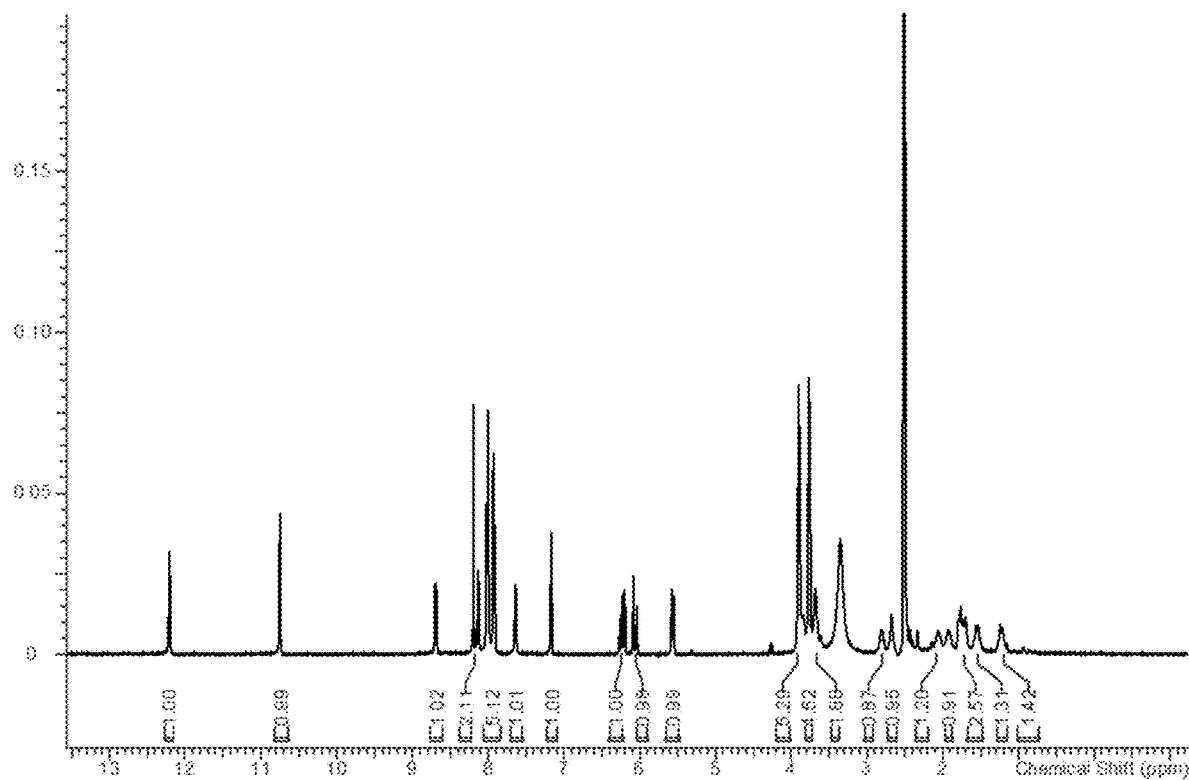

Fig. 17  PLM Photograph of Free Form Pattern D After Being Dried at 50°C for 3 h, Sample ID FR01446-1-SU3-Pattern D-dry
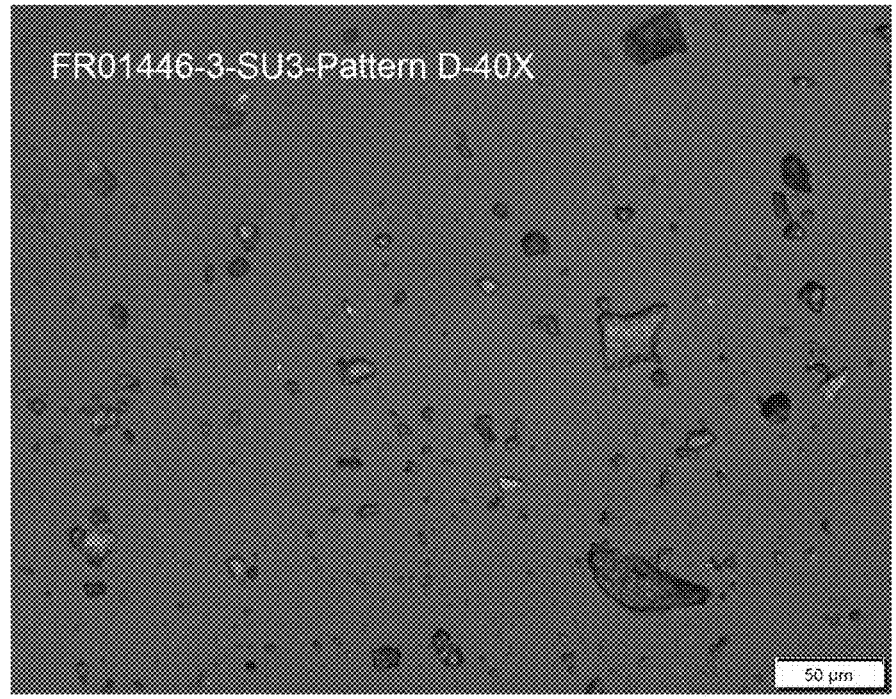

Fig. 18 XRPD Pattern of Pattern D, Sample ID FR01446-3-scale up-Pattern D-THF-water-dry
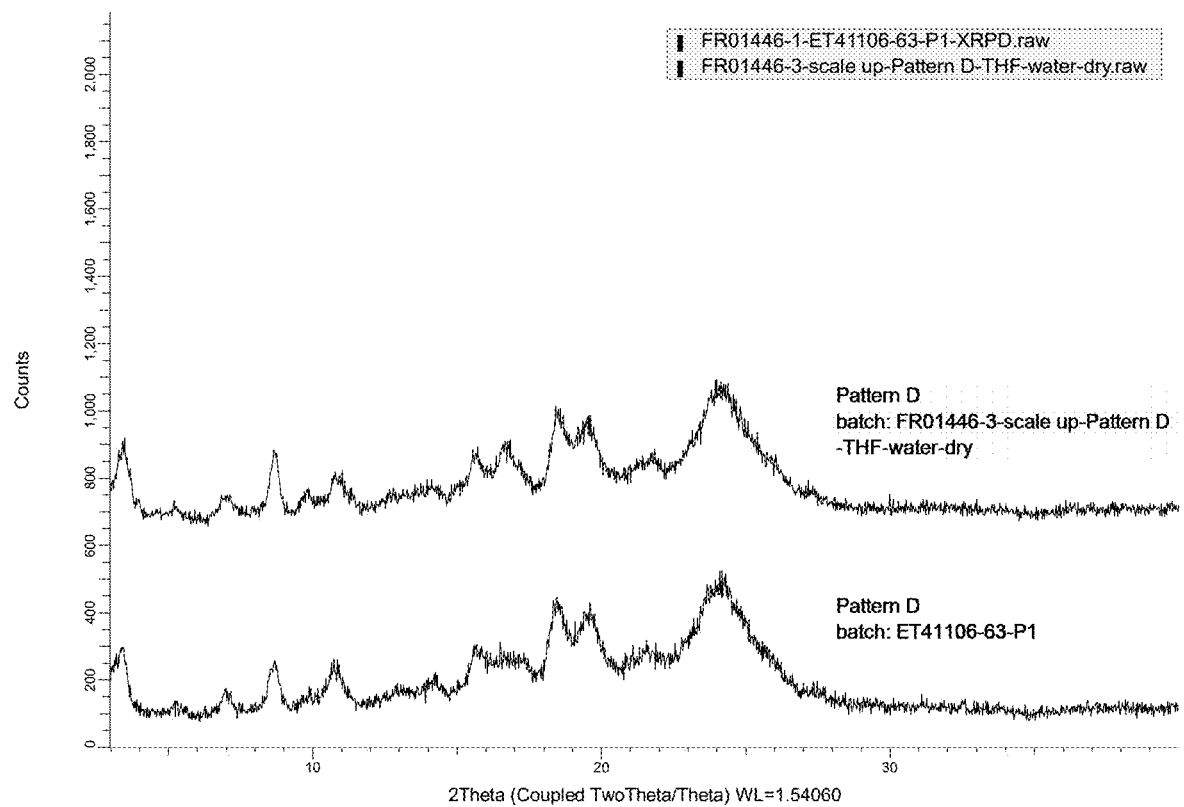

Fig. 19 TGA Thermogram of Pattern D, Sample ID FR01446-3-scale up-Pattern D-THF-water-dry
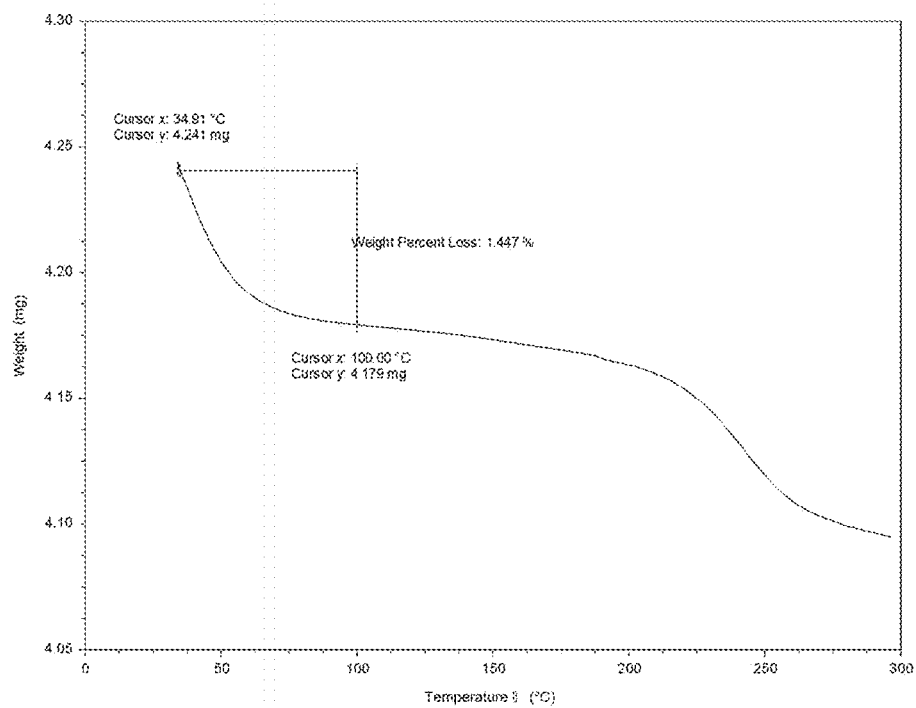

Fig. 20  DSC Thermogram of Pattern D, Sample ID FR01446-3-scale up-Pattern D-THF-water-dry
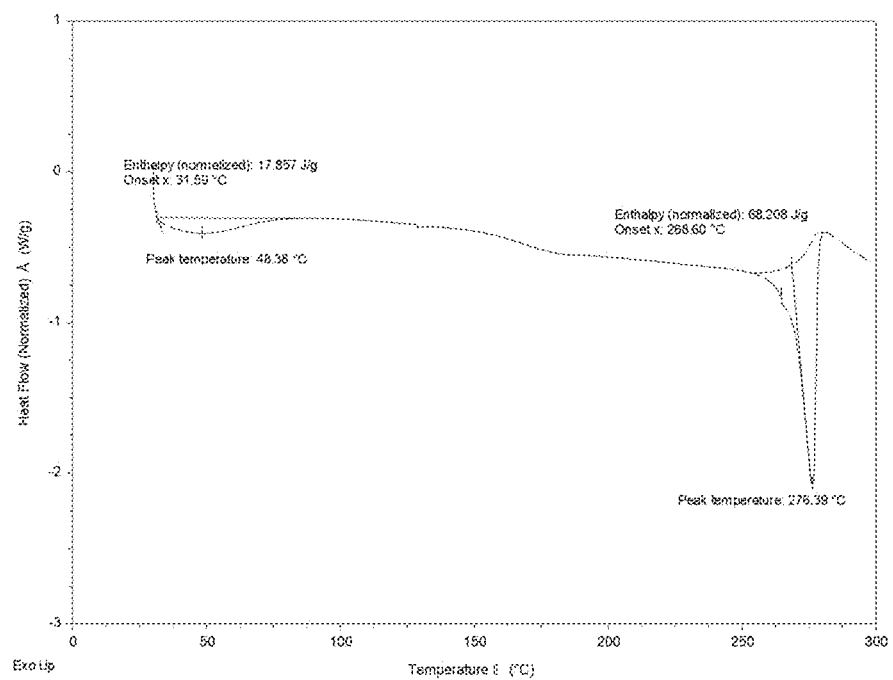

Fig. 21  $^1$H NMR Spectrum of Pattern D, Sample ID FR01446-3-scale up-Pattern D-THF-water-dry
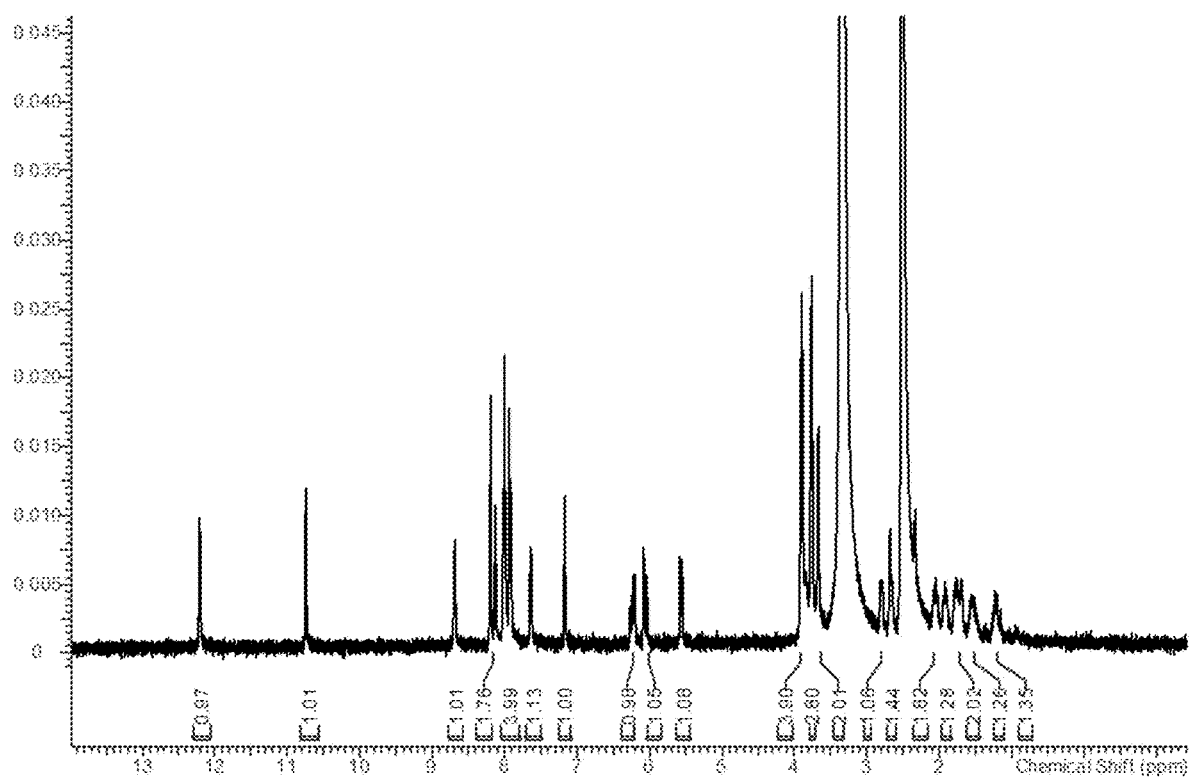

Fig. 22    XRPD Overlay of Pattern D (50 mg) After Grinding Simulation Experiment for 10 min
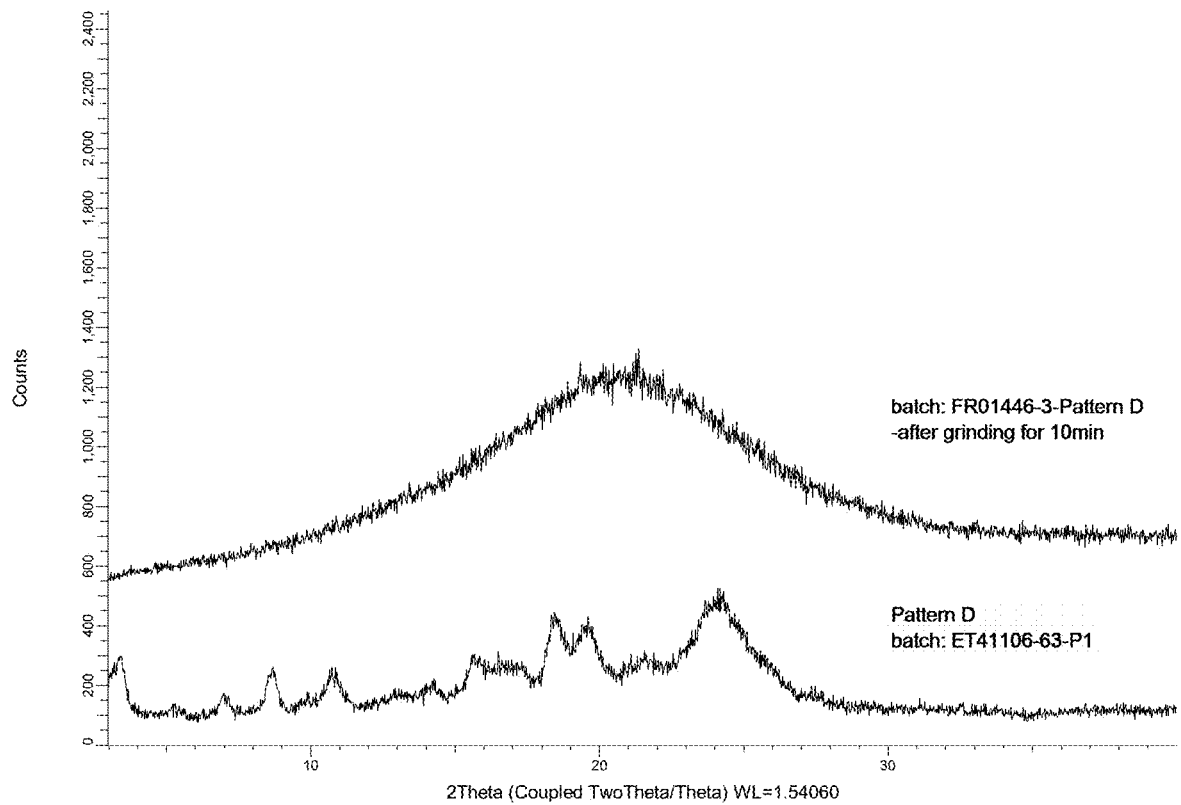

Fig. 23    mDSC Thermogram of Pattern D (50 mg) After Grinding Simulation Experiment for 10 min
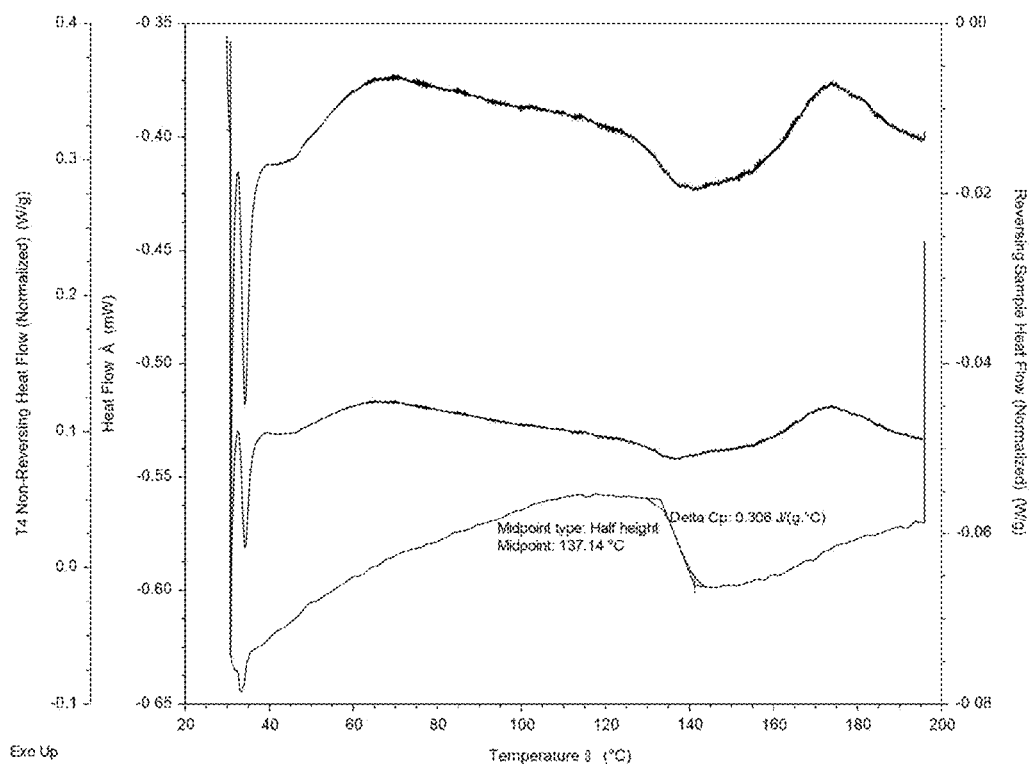

Fig. 24    XRPD Overlay of Pattern D (600 mg) After Grinding Simulation Experiment for 10 min
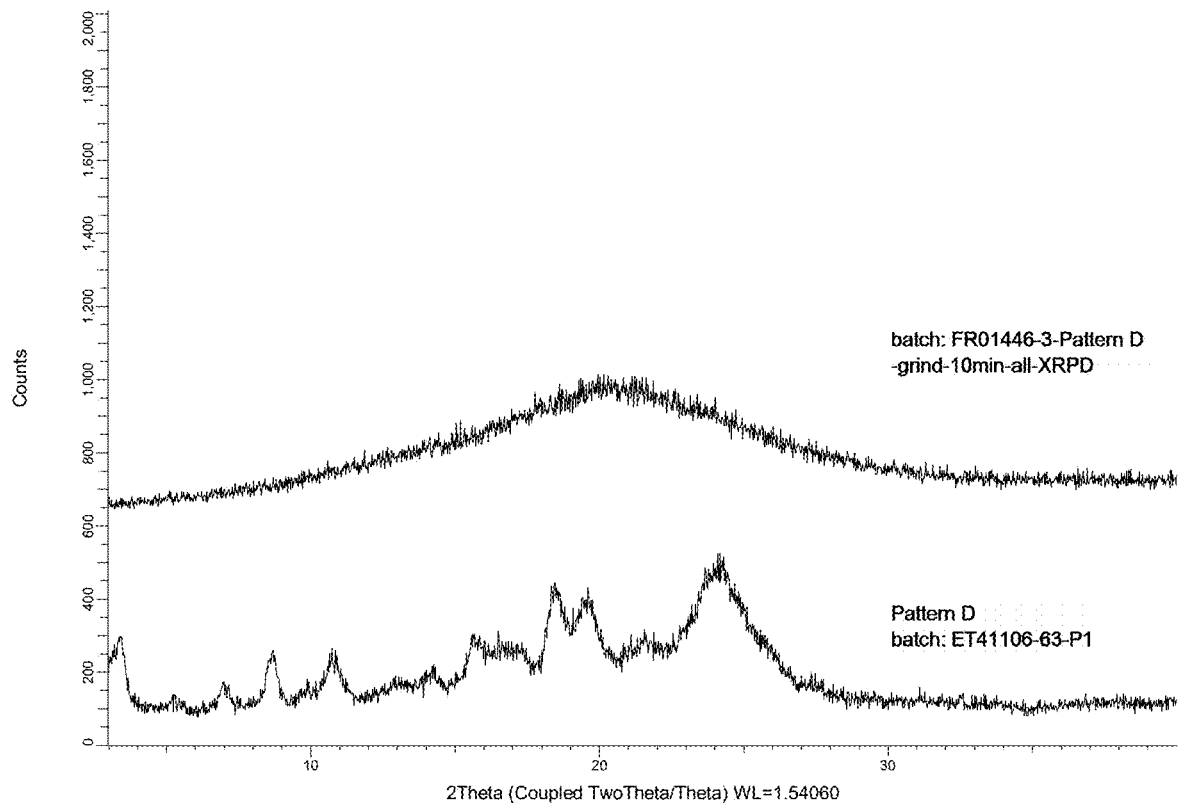

Fig. 25 mDSC Thermogram of Pattern D (600 mg) After Grinding Simulation Experiment for 10 min
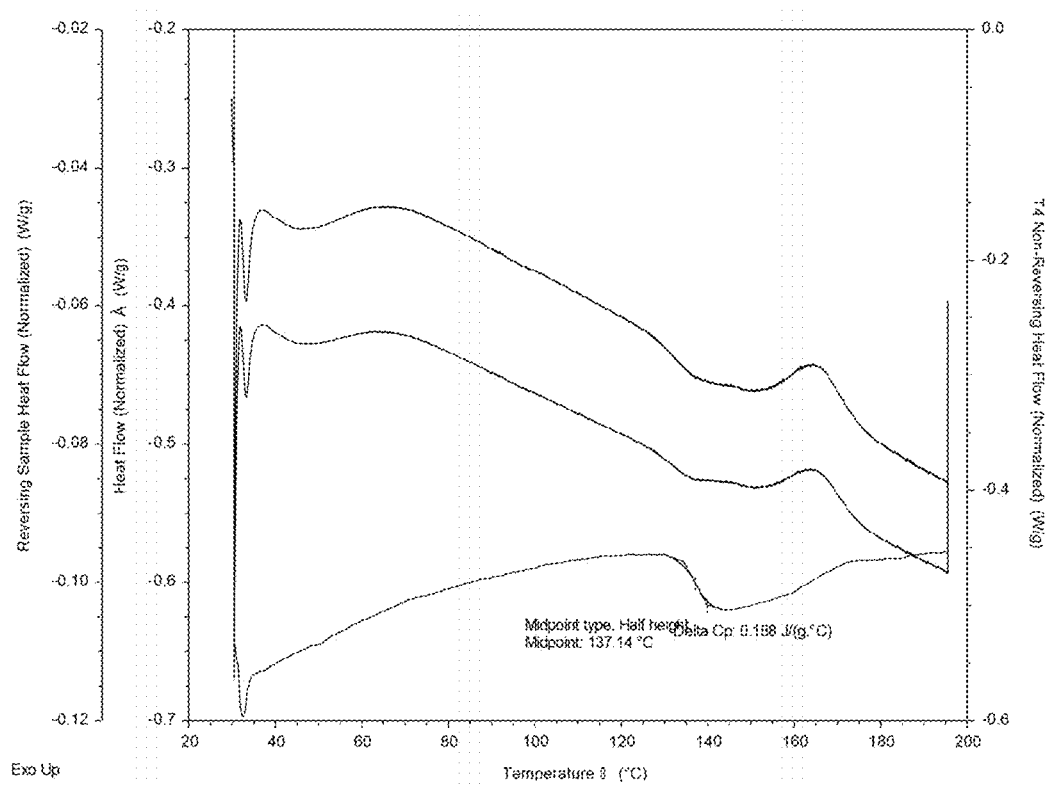

Fig. 26 XRPD Overlay of Pattern D (2 g) After Grinding Simulation Experiment for 10 min
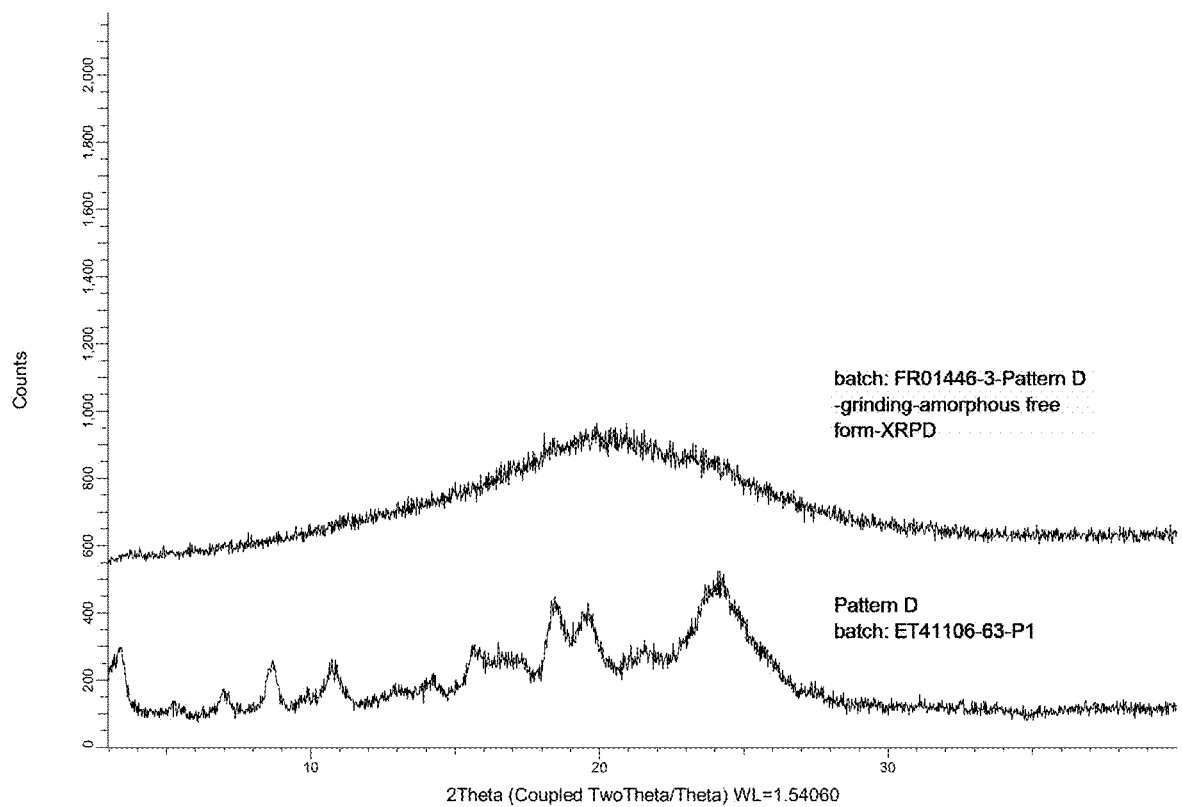

Fig. 27 mDSC Thermogram of Pattern D (2 g) After Grinding Simulation Experiment for 10 min
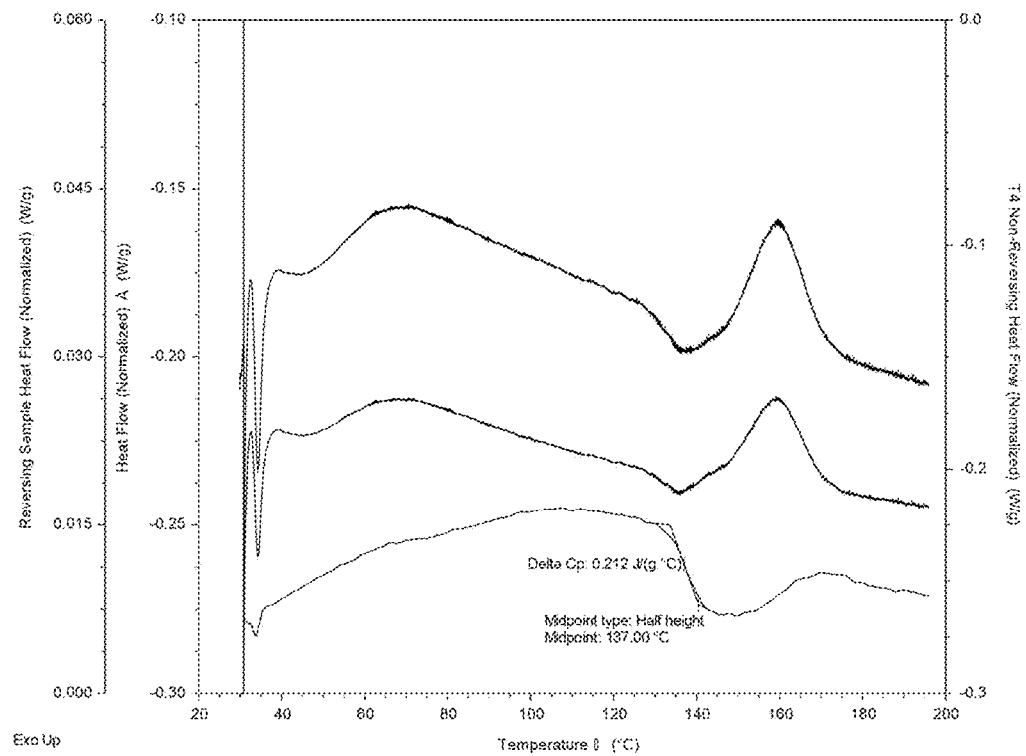

Fig. 28E
Newly Diagnosed
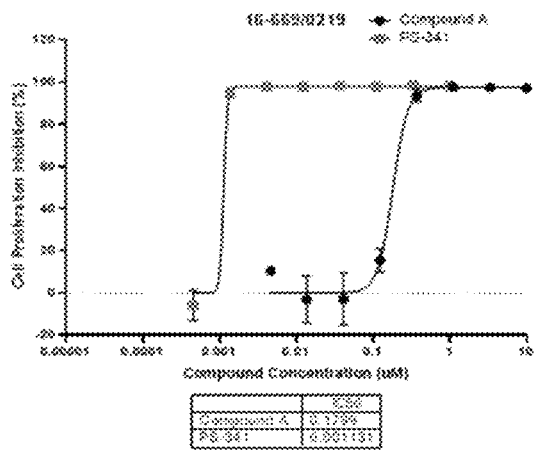
(A)
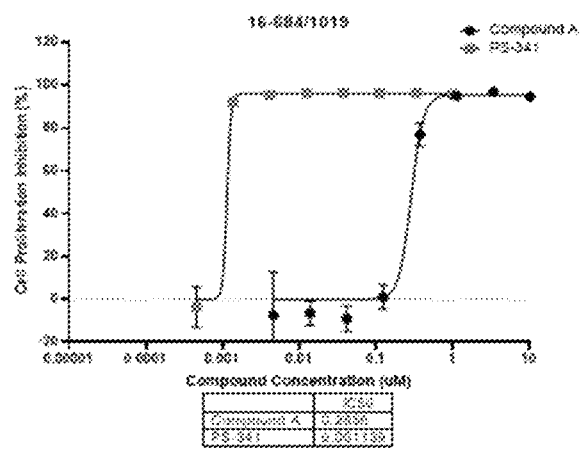
(B)
Relapased/Refractory
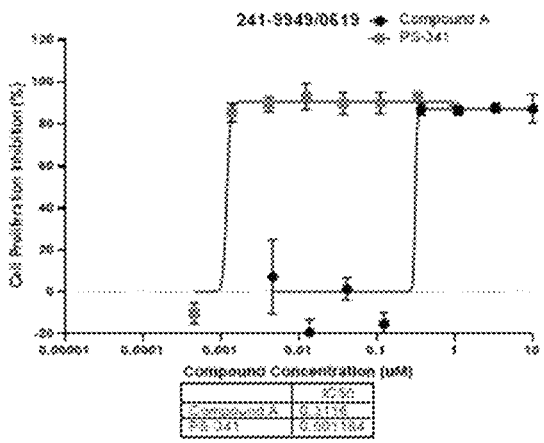
(C)
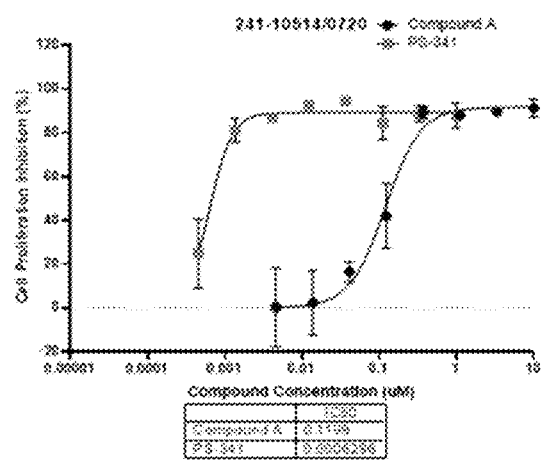
(D)

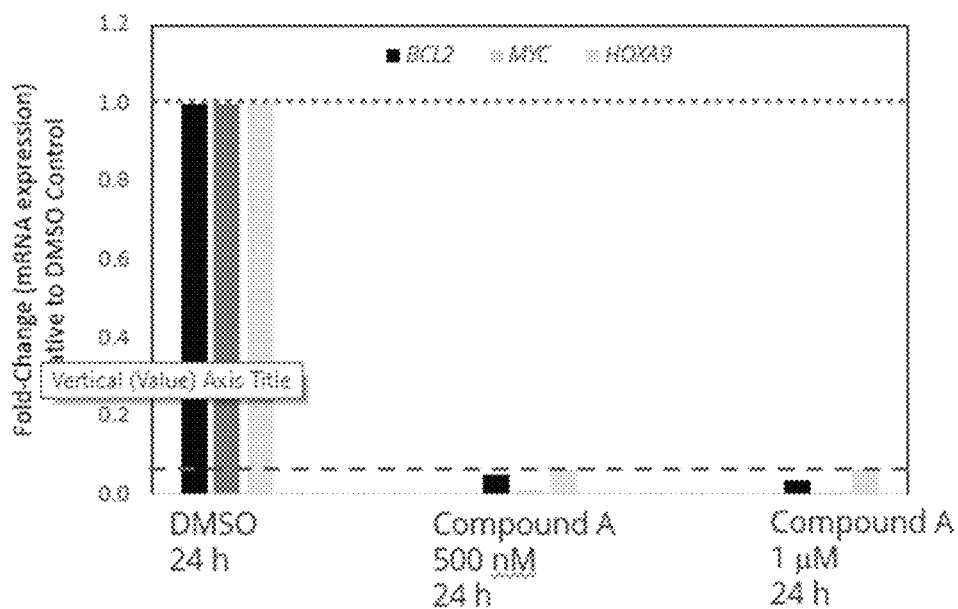
Fig. 31: Relative Gene Expression – Compound A (A)  (B)

Fig. 32C, 32D, and 32E (C)  (D)  (E)

Compound P

CRYSTALLINE FORMS OF N-[4-[4-(4-MORPHOLINYL)-7H-PYRROLO[2,3-D]PYRIMIDIN-6-YL]PHENYL]-4-[[3(R)-[(1-OXO-2-PROPEN-1-YL)AMINO]-1-PIPERIDINYL]METHYL]-2-PYRIDINE-CARBOXAMIDE AS AN IRREVERSIBLE INHIBITOR OF MENIN-MLL INTERACTION

CROSS REFERENCE

The present application claims the benefit of U.S. provisional patent application nos. 63/235,662, filed Aug. 20, 2021, 63/279,053, filed Nov. 12, 2021, and 63/310,076, filed Feb. 14, 2022, the contents of each of which are hereby incorporated by reference in their entireties.

FIELD

Described herein is a covalent inhibitor of menin-MLL N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide, including stereoisomers, crystalline forms, solvates, and pharmaceutically acceptable salts thereof, as well as pharmaceutical compositions that include the above covalent inhibitor of menin-MLL interaction and methods of using the above covalent inhibitor of menin-MLL interaction in the treatment of diseases or conditions that would benefit from inhibition of menin-MLL activity.

BACKGROUND

The Histone-lysine N-methyltransferase 2 (KMT2) family of proteins, which currently consists of at least five members, methylate lysine 4 on the histone H3 tails at important regulatory regions in the genome and thereby impart crucial functions through the modulation of chromatin structures and DNA accessibility (Morera, Lübbert, and Jung., *Clin. Epigenetics* 8, 57—(2016)). These enzymes are known to play an important role in the regulation of gene expression during early development and hematopoiesis (Rao & Dou., *Nat. Rev. Cancer* 15, 334-346 (2015)).

The human KMT2 family was initially named the mixed-lineage leukemia (MLL) family, owing to the role of the first-found member in this disease, KMT2A, which is still commonly referred to as MLL1 or MLL in routine clinical practice.

KMT2A (MLL1) is frequently found to be cytogenetically targeted in several types of leukemia (e.g., ALL and AML), and in those cases where balanced chromosomal translocations are found, these typically target KMT2A (MLL1) and one of over eighty translocation partner genes that have been described to date (Winters and Bernt, *Front. Pediatr.* 5, 4 (2017)). These chromosomal anomalies often result in the formation of fusion genes that encode fusion proteins which are believed to be causally related to the onset and/or progression of the disease. Inhibition of menin may be a promising strategy for treating MLL related diseases, including leukemia.

SUMMARY

Described herein is a covalent inhibitor of menin-HLL interaction N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide, including stereoisomers, pharmaceutically acceptable solvates (including hydrates), polymorphs, and amorphous phases, and methods of uses thereof. Also described are pharmaceutically acceptable salts of the inhibitor of menin-HLL interaction, including stereoisomers, pharmaceutically acceptable solvates (including hydrates), polymorphs, and amorphous phases, and methods of uses thereof. N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide, as well as stereoisomers and pharmaceutically acceptable salts thereof, are used in the manufacture of medicaments for the treatment of diseases or conditions that are associated with menin-MLL activity. N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide is a covalent inhibitor of menin-MLL interaction.

Also described herein are methods for preparing crystalline forms of N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide. Further described are pharmaceutical compositions that include the crystalline forms and methods of using the covalent inhibitor of menin-MLL interaction in the treatment of diseases or conditions (including diseases or conditions wherein covalent inhibition of menin-MLL interaction provides therapeutic benefit to a mammal having the disease or condition).

In one embodiment, the covalent inhibitor of menin-MLL interaction N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide is an (R)-isomer. In another embodiment, the covalent inhibitor of menin-HLL interaction is an (S)-isomer.

In a particular embodiment, the covalent inhibitor of menin-HLL interaction is N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide.

In one embodiment, the covalent inhibitor of menin-MLL interaction is anhydrous N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide.

In another embodiment, the covalent inhibitor of menin-MLL interaction is a crystalline anhydrous N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide.

In a further embodiment, the covalent inhibitor of menin-MLL interaction is an amorphous anhydrous N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide.

In another embodiment, the covalent inhibitor of menin-MLL interaction is a crystalline hydrate of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide.

In a further embodiment, the covalent inhibitor of menin-MLL interaction is an amorphous hydrate of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide.

In one embodiment, the covalent inhibitor of menin-MLL interaction N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide is an (R)-isomer, which is designated as Compound A. In certain embodiments, Compound A is substantially free from another enantiomer. In certain embodiments, Compound A is isolated. In certain embodiments, Compound A is in enantiomeric excess.

In one embodiment, the covalent inhibitor of menin-MLL interaction N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide is an (S)-isomer, which is designated as Compound B. In certain embodiments, Compound B is substantially free of another enantiomer. In certain embodiments, Compound B is isolated. In certain embodiments, Compound B is in enantiomeric excess.

Form A

In one particular aspect, described herein is a Form A of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A) that has at least one of the following properties:

(a) an X-ray powder diffraction (XRPD) pattern substantially the same as shown in FIG. 1A;
(b) an X-ray powder diffraction (XRPD) pattern with characteristic peaks at 3.5±0.1° 2-Theta, 10.4±0.1° 2-Theta, 14.7±0.1° 2-Theta, 17.1±0.1° 2-Theta, 21±0.1° 2-Theta, 24.9±0.1° 2-Theta, 29.5±0.1° 2-Theta, and 34.1±0.1° 2-Theta;
(c) an X-ray powder diffraction (XRPD) pattern with characteristic peaks at 3.5±0.1° 2-Theta, 17.1±0.1° 2-Theta, 21.0±0.1° 2-Theta, 24.9±0.1° 2-Theta, and 29.5±0.1° 2-Theta;
(d) a differential scanning calorimetry (DSC) thermogram with an endotherm having an onset at about 234.6° C. and a peak at about 245° C.;

or (e) combinations thereof.

In some embodiments, Form A is a crystalline form. In some embodiments, Form A is a hydrate.

In some embodiments, Form A has an X-ray powder diffraction (XRPD) pattern substantially the same as shown in FIG. 1A. In some embodiments, Form A has an X-ray powder diffraction (XRPD) pattern substantially the same as shown below:

XRPD TABLE A

XRPD Pattern of Free Form Pattern A
(Compound A, Form A)

| Index | Angle* | dValue | Net Intensity | Gross Intensity | Rel. Intensity |
|---|---|---|---|---|---|
| 1 | 3.472° | 25.42665 A | 817.224 | 988.968 | 100.0% |
| 2 | 10.395° | 8.50313 A | 59.0212 | 198.748 | 7.2% |
| 3 | 14.717° | 6.01444 A | 65.3863 | 347.962 | 8.0% |
| 4 | 17.137° | 5.17011 A | 546.417 | 915.709 | 66.9% |
| 5 | 21.029° | 4.22120 A | 309.975 | 720.606 | 37.9% |
| 6 | 24.866° | 3.57780 A | 405.254 | 738.189 | 49.6% |
| 7 | 29.485° | 3.02703 A | 125.412 | 381.519 | 15.3% |
| 8 | 34.050° | 2.63088 A | 49.0499 | 244.102 | 6.0% |

*±0.1°

In some embodiments, Form A has an X-ray powder diffraction (XRPD) pattern with characteristic peaks at one, two, three, four, five, six, seven, or eight of 3.5±0.1° 2-Theta, 10.4±0.1° 2-Theta, 14.7±0.1° 2-Theta, 17.1±0.1° 2-Theta, 21±0.1° 2-Theta, 24.9±0.1° 2-Theta, 29.5±0.1° 2-Theta, and 34.1±0.1° 2-Theta.

In some embodiments, Form A has an X-ray powder diffraction (XRPD) pattern with characteristic peaks at 3.5±0.1° 2-Theta, 17.1±0.1° 2-Theta, 21.0±0.1° 2-Theta, 24.9±0.1° 2-Theta, and 29.5±0.1° 2-Theta.

In some embodiments, Form A has a melting temperature of about 245° C.

In some embodiments, Form A has a thermogravimetric analysis (TGA) thermogram that shows 1.80% weight loss up to around 200° C.

In some embodiments, Form A has a DSC thermogram with an endotherm having an onset at about 234.6° C. and a peak at about 245.0° C.

In some embodiments, Form A is hygroscopic.

Form B

In one particular aspect, described herein is a Form B of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A) that has at least one of the following properties:

(a) an X-ray powder diffraction (XRPD) pattern substantially the same as shown in FIG. 2A;
(b) an X-ray powder diffraction (XRPD) pattern with characteristic peaks at one, two, three, four, five, six, seven, or eight of 5.9±0.1° 2-Theta, 8.6±0.1° 2-Theta, 10.5±0.1° 2-Theta, 12.6±0.1° 2-Theta, 16.9±0.1° 2-Theta, 19±0.1° 2-Theta, 20.5±0.1° 2-Theta, and 24.6±0.1° 2-Theta;
(c) an X-ray powder diffraction (XRPD) pattern with characteristic peaks at 8.6±0.1° 2-Theta, 10.5±0.1° 2-Theta, 12.6±0.1° 2-Theta, 16.9±0.1° 2-Theta, 19.1±0.1° 2-Theta, 20.5±0.1° 2-Theta, and 24.6±0.1° 2-Theta;

or (d) combinations thereof.

In some embodiments, Form B is a crystalline form. In some embodiments, Form B is a hydrate.

In some embodiments, Form B has an X-ray powder diffraction (XRPD) pattern substantially the same as shown in FIG. 2A. In some embodiments, Form B has an X-ray powder diffraction (XRPD) pattern substantially the same as shown below:

TABLE B

XRPD Pattern of Free Form Pattern B (Compound A, Form B)

| Index | Angle* | dValue | Net Intensity | Gross Intensity | Rel. Intensity |
|---|---|---|---|---|---|
| 1 | 5.925° | 14.90443 A | 40.3324 | 148.819 | 7.6% |
| 2 | 8.587° | 10.28913 A | 58.2126 | 208."167 | 11.0% |
| 3 | 10.522° | 8.40127 A | 58.0415 | 236.296 | 10.9% |
| 4 | 12.611° | 7.01369 A | 188.498 | 390.785 | 35.5% |
| 5 | 16.854° | 5.25634 A | 132.691 | 407.283 | 25.0% |
| 6 | 19.039° | 4.65756 A | 198.523 | 520.924 | 37.4% |
| 7 | 20.454° | 4.33858 A | 334.602 | 672.713 | 63.1% |
| 8 | 24.632° | 3.61124 A | 530.528 | 845.184 | 100.0% |

*±0.1°

In some embodiments, Form B has an X-ray powder diffraction (XRPD) pattern with characteristic peaks at 5.9±0.1° 2-Theta, 8.6±0.1° 2-Theta, 10.5±0.1° 2-Theta, 12.6±0.1° 2-Theta, 16.9±0.1° 2-Theta, 19±0.1° 2-Theta, 20.5±0.1° 2-Theta, and 24.6±0.1° 2-Theta.

In some embodiments, Form B has an X-ray powder diffraction (XRPD) pattern with characteristic peaks at 8.6±0.1° 2-Theta, 10.5±0.1° 2-Theta, 12.6±0.1° 2-Theta, 16.9±0.1° 2-Theta, 19.1±0.1° 2-Theta, 20.5±0.1° 2-Theta, and 24.6±0.1° 2-Theta.

In some embodiments, Form B has a thermogravimetric analysis (TGA) thermogram that shows 1.350% weight loss up to around 100° C.

In some embodiments, Form B is hygroscopic.

Form C

In one particular aspect, described herein is a Form C of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A) that has at least one of the following properties:

(a) an X-ray powder diffraction (XRPD) pattern substantially the same as shown in FIG. 3A;
(b) an X-ray powder diffraction (XRPD) pattern with characteristic peaks at one, two, three, four, five, six, seven, eight, nine, ten, eleven, or twelve of 5.2±0.1° 2-Theta, 5.9±0.1° 2-Theta, 7.2±0.1° 2-Theta, 8.7±0.1° 2-Theta, 10.6±0.1° 2-Theta, 12.2±0.1° 2-Theta, 14.3±0.1° 2-Theta, 15.1±0.1° 2-Theta, 15.9±0.1° 2-Theta, 17.5±0.1° 2-Theta, 18.1±0.1° 2-Theta, and 20.1±0.1° 2-Theta;
(c) an X-ray powder diffraction (XRPD) pattern with characteristic peaks at 5.2±0.1° 2-Theta, 5.9±0.1° 2-Theta, 8.7±0.1° 2-Theta, 12.2±0.1° 2-Theta, 14.3±0.1° 2-Theta, 15.9±0.1° 2-Theta, and 17.5±0.1° 2-Theta;
(d) a DSC thermogram with an endotherm having an onset at about 150.23° C. and a peak at about 156.86° C.;
or
(e) combinations thereof.

In some embodiments, Form C is a crystalline form. In some embodiments, Form C is a solvate. In some embodiments, Form C is a 2,2,2-trifluoroethanol (TFE) solvate.

In some embodiments, Form C has an X-ray powder diffraction (XRPD) pattern substantially the same as shown in FIG. 3A.

In some embodiments, Form C has an X-ray powder diffraction (XRPD) pattern substantially the same as shown below:

TABLE C

XRPD Pattern of Free Form Pattern C (Compound A, Form C)

| Index | Angle* | dValue | Net Intensity | Gross Intensity | Rel. Intensity |
|---|---|---|---|---|---|
| 1 | 5.186° | 17.02747 A | 133.727 | 225.336 | 58.9% |
| 2 | 5.861° | 15.06777 A | 130.303 | 222.034 | 57.4% |
| 3 | 7.211° | 12.24949 A | 55.5581 | 144.593 | 24..5% |
| 4 | 8.657° | 10.20582 A | 139.726 | 224.000 | 61.6% |
| 5 | 10.554° | 8.37575 A | 54.3884 | 141.714 | 24.0% |
| 6 | 12.161° | 7.27219 A | 226.948 | 332.463 | 100.0% |
| 7 | 14.347° | 6.16879 A | 117.349 | 238.66"1 | 51.7% |
| 8 | 15.054° | 5.88057 A | 115.107 | 239.909 | 50.7% |
| 9 | 15.857° | 5.58433 A | 155.055 | 281.563 | 68.3% |
| 10 | 17.464° | 5.07388 A | 125.43·1 | 248.'146 | 55.3% |
| 11 | 18.107° | 4.89517 A | 110.474 | 228.981 | 48.7% |
| 12 | 20.068° | 4.42109 A | 105.704 | 209.415 | 46.6% |

*±0.1°

In some embodiments, Form C has an X-ray powder diffraction (XRPD) pattern with characteristic peaks at 5.2±0.1° 2-Theta, 5.9±0.1° 2-Theta, 7.2±0.1° 2-Theta, 8.7±0.1° 2-Theta, 10.6±0.1° 2-Theta, 12.2±0.1° 2-Theta, 14.3±0.1° 2-Theta, 15.1±0.1° 2-Theta, 15.9±0.1° 2-Theta, 17.5±0.1° 2-Theta, 18.1±0.1° 2-Theta, and 20.1±0.1° 2-Theta.

In some embodiments, Form C has an X-ray powder diffraction (XRPD) pattern with characteristic peaks at 5.2±0.1° 2-Theta, 5.9±0.1° 2-Theta, 8.7±0.1° 2-Theta, 12.2±0.1° 2-Theta, 14.3±0.1° 2-Theta, 15.9±0.1° 2-Theta, and 17.5±0.1° 2-Theta.

In some embodiments, Form C has a DSC thermogram with an endotherm having an onset at about 150.23° C. and a peak at about 156.86° C.

In some embodiments, Form C is hygroscopic.

Form D

In one particular aspect, described herein is a Form D of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A) that has at least one of the following properties:

(a) an X-ray powder diffraction (XRPD) pattern substantially the same as shown in FIG. 4A;
(b) an X-ray powder diffraction (XRPD) pattern with characteristic peaks at one, two, three, four, five, six, seven, eight, nine, ten, eleven, twelve, or thirteen of 3.4±0.1° 2-Theta, 5.3±0.1° 2-Theta, 7±0.1° 2-Theta, 8.7±0.1° 2-Theta, 10.8±0.1° 2-Theta, 12.9±0.1° 2-Theta, 14.3±0.1° 2-Theta, 15.6±0.1° 2-Theta, 17±0.1° 2-Theta, 18.5±0.1° 2-Theta, 19.6±0.1° 2-Theta, 21.5±0.1° 2-Theta, and 24.2±0.1° 2-Theta;
(c) an X-ray powder diffraction (XRPD) pattern with characteristic peaks at 3.4±0.1° 2-Theta, 8.7±0.1° 2-Theta, 10.7±0.1° 2-Theta, 15.6±0.1° 2-Theta, 18.5±0.1° 2-Theta, 19.6±0.1° 2-Theta, and 24.2±0.1° 2-Theta;
(d) substantially the same X-ray powder diffraction (XRPD) pattern post storage in an open container at 40° C. and 75% relative humidity (RH) for at least a week;
(e) substantially the same X-ray powder diffraction (XRPD) pattern post storage in an open container at 25° C. and 92% RH for at least a week;
(f) substantially the same X-ray powder diffraction (XRPD) pattern post storage in a closed container at 60° C. and 75% RH for at least a week;
(g) Infrared (IR) spectrum substantially similar to the one set forth in FIG. 9A;
(h) Infrared (IR) spectrum (FIG. 9A) peaks at about 3332 cm$^{-1}$, about 2853 cm$^{-1}$, about 1561 cm$^{-1}$, about 1524 cm$^{-1}$, about 1319 cm$^{-1}$, about 1258 cm$^{-1}$, and about 1067 cm$^{-1}$;
(i) a thermogravimetric analysis (TGA) thermogram substantially similar to the one set forth in FIG. 10;
(j) a DSC thermogram substantially similar to the one set forth in FIG. 11;
(k) a DSC thermogram with an endotherm having an onset at about 260.5° C. and a peak at about 273° C.;
(l) $^1$H NMR (NMR) spectrum substantially similar to the one set forth in FIG. 12; (m) an observed hygroscopicity and absorption of about 2.1% water from 40% RH to 70% RH at 25° C.;
(n) an observed aqueous solubility of about 0.004 mg/mL at about pH 4.5;
or
(o) combinations thereof.

In some embodiments, Form D is a crystalline form.

In some embodiments, Form D is a hydrate.

In some embodiments, Form D has an X-ray powder diffraction (XRPD) pattern substantially the same as shown in FIG. 4A.

In some embodiments, Form D has an X-ray powder diffraction (XRPD) pattern substantially the same as shown below:

TABLE D

XRPD Pattern of Free Form Pattern D (Compound A, Form D)

| Index | Angle* | dValue | Net Intensity | Gross Intensity | Rel. Intensity |
|---|---|---|---|---|---|
| 1 | 3.354° | 26.32488 A | 123.441 | 290.6 | 42.8% |
| 2 | 5.314° | 16.61580 A | 32.3960 | 129.144 | 11.2% |
| 3 | 6.986° | 12.64352 A | 59.6702 | 163.276 | 20.7% |
| 4 | 8.689° | 10.16814 A | 145.824 | 261.449 | 50.6% |
| 5 | 10.747° | 8.22587 A | 139.539 | 268.016 | 48.4% |
| 6 | 12.900° | 6.85704 A | 27.2461 | 166.544 | 9.4% |
| 7 | 14.250° | 6.21032 A | 54.4465 | 202.156 | 18.9% |
| 8 | 15.632° | 566419 | 130.038 | 299.722 | 45.1% |
| 9 | 16.982° | 5.21684 A | 81.8461 | 276.600 | 28.4% |
| 10 | 18.461° | 4.80220 A | 228.372 | 444.437 | 79.2% |
| 11 | 19.618° | 4.52148 A | 193.879 | 421.715 | 67.2% |
| 12 | 21.514° | 4.12702 A | 55.4205 | 289.294 | 19.2% |
| 13 | 24.150° | 3..68223 A | 288.350 | 503.268 | 100.0% |

*±0.1°

In some embodiments, Form D has an X-ray powder diffraction (XRPD) pattern with characteristic peaks at 3.4±0.1° 2-Theta, 5.3±0.1° 2-Theta, 7±0.1° 2-Theta, 8.7±0.1° 2-Theta, 10.8±0.1° 2-Theta, 12.9±0.1° 2-Theta, 14.3±0.1° 2-Theta, 15.6±0.1° 2-Theta, 17±0.1° 2-Theta, 18.5±0.1° 2-Theta, 19.6±0.1° 2-Theta, 21.5±0.1° 2-Theta, and 24.2±0.1° 2-Theta.

In some embodiments, Form D has an X-ray powder diffraction (XRPD) pattern with characteristic peaks at 3.4±0.1° 2-Theta, 8.7±0.1° 2-Theta, 10.7±0.1° 2-Theta, 15.6±0.1° 2-Theta, 18.5±0.1° 2-Theta, 19.6±0.1° 2-Theta, and 24.2±0.1° 2-Theta.

In some embodiments, Form D has substantially the same X-ray powder diffraction (XRPD) pattern post storage in an open container at 40° C. and 75% RH for at least a week.

In some embodiments, Form D has substantially the same X-ray powder diffraction (XRPD) pattern post storage in an open container at 25° C. and 92% RH for at least a week.

In some embodiments, Form D has substantially the same X-ray powder diffraction (XRPD) pattern post storage in a closed container at 60° C. and 75% RH for at least a week.

In some embodiments, Form D has an Infrared (IR) spectrum substantially similar to the one set forth in FIG. 9A.

In some embodiments, Form D has an Infrared (IR) spectrum weak peaks at about 3332 cm$^{-1}$, about 2853 cm$^{-1}$, about 1561 cm$^{-1}$, about 1524 cm$^{-1}$, about 1319 cm$^{-1}$, about 1258 cm$^{-1}$, and about 1067 cm$^{-1}$.

In some embodiments, Form D has a melting temperature of about 272-274° C.

In some embodiments, Form D has a thermogravimetric analysis (TGA) thermogram substantially similar to the one set forth in FIG. 10.

In some embodiments, Form D has a DSC thermogram substantially similar to the one set forth in FIG. 11.

In some embodiments, Form D has a DSC thermogram with an endotherm having an onset at about 260.5° C. and a peak at about 273° C.

In some embodiments, Form D has an $^1$H NMR (NMR) spectrum substantially similar to the one set forth in FIG. 12.

In some embodiments, Form D is hygroscopic.

In some embodiments, Form D has an observed aqueous solubility of about 0.004 mg/mL at about pH 4.5.

Form E

In one particular aspect, described herein is a Form E of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A) that has at least one of the following properties:

(a) an X-ray powder diffraction (XRPD) pattern substantially the same as shown in FIG. 5A;

(b) an X-ray powder diffraction (XRPD) pattern with characteristic peaks at one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, or thirty-four of 3.4±0.1° 2-Theta, 4.7±0.1° 2-Theta, 6.3±0.1° 2-Theta, 6.9±0.1° 2-Theta, 7.1±0.1° 2-Theta, 7.6±0.1° 2-Theta, 8.6±0.1° 2-Theta, 9.3±0.1° 2-Theta, 10.8±0.1° 2-Theta, 12±0.1° 2-Theta, 12.5±0.1° 2-Theta, 13±0.1° 2-Theta, 13.8±0.1° 2-Theta, 15.7±0.1° 2-Theta, 16.2±0.1° 2-Theta, 16.7±0.1° 2-Theta, 17±0.1° 2-Theta, 17.5±0.1° 2-Theta, 18.4±0.1° 2-Theta, 18.6±0.1° 2-Theta, 19.6±0.1° 2-Theta, 20.7±0.1° 2-Theta, 21.4±0.1° 2-Theta, 22.2±0.1° 2-Theta, 23±0.1° 2-Theta, 24.2±0.1° 2-Theta, 25.3±0.1° 2-Theta, 26±0.1° 2-Theta, 28±0.1° 2-Theta, 29.2±0.1° 2-Theta, 30.5±0.1° 2-Theta, 31.6±0.1° 2-Theta, 33.6±0.1° 2-Theta, and 34.5±0.1° 2-Theta;

(c) an X-ray powder diffraction (XRPD) pattern with characteristic peaks at 4.7±0.1° 2-Theta, 7.7±0.1° 2-Theta, 10.8±0.1° 2-Theta, 13.8±0.1° 2-Theta, 17.0±0.1° 2-Theta, 18.4±0.1° 2-Theta, and 18.6±0.1° 2-Theta;

(d) a DSC thermogram with an endotherm having an onset at about 112.34° C. and a peak at about 137.26° C.;

or (e) combinations thereof.

In some embodiments, Form E is a crystalline form. In some embodiments, Form E is a DMSO solvate.

In some embodiments, Form E has an X-ray powder diffraction (XRPD) pattern substantially the same as shown in FIG. 5A.

In some embodiments, Form E has an X-ray powder diffraction (XRPD) pattern substantially the same as shown below:

TABLE E

XRPD Pattern of Free Form Pattern E (Compound A, Form E)

| Index | Angle* | dValue | Net Intensity | Gross Intensity | Rel. Intensity |
|---|---|---|---|---|---|
| 1 | 3.354° | 26.32488 A | 123.441 | 290.6 | 42.8% |
| 1 | 3.406° | 25.91845 A | 30.3536 | 129.000 | 4.1% |
| 2 | 4.663° | 18.93379 A | 498.089 | 574.667 | 67.8% |
| 3 | 6259° | 14.10883 A | 57.5069 | 137.733 | 7.8% |
| 4 | 6.'902° | 12.79648 A | 113.808 | 202.012 | 15.5% |
| 5 | 7.138° | 12.37390 A | 102.194 | 192.583 | 13.9% |
| 6 | 7.574° | 11.66253 A | 638.030 | 731.400 | 86.8% |
| 7 | 8.627° | 10.24171 A | 69.9785 | 170.785 | 9.5% |
| 8 | 9.299° | 9.50315 A | 72.5036 | 180.093 | 9.9% |
| 9 | 10.790° | 8.19307 A | 436.276 | 549.567 | 59.4% |
| 10 | 11.968° | 7.38895 A | 22.2062 | 138.035 | 3.0% |
| 11 | 12.480° | 7.08703 A | 112.097 | 234.424 | 15.3% |
| 12 | 12.947° | 6.83238 A | 280.661 | 406.890 | 38.2% |
| 13 | 13.779° | 6.42140 A | 596.813 | 725.831 | 81.1% |
| 14 | 15.690° | 5.64346 A | 56.4454 | 209.584 | 7.7% |
| 15 | 16.188° | 5.47110 A | 122.791 | 286.384 | 16.7% |
| 16 | 16.663° | 5.31622 A | 85.8718 | 257.783 | 11.7% |
| 17 | 16.982° | 5.21684 A | 103.238 | 279.836 | 14.0% |
| 18 | 17.512° | 5.06020 A | 175.880 | 358.624 | 23.9% |

TABLE E-continued

XRPD Pattern of Free Form Pattern E
(Compound A, Form E)

| Index | Angle* | dValue | Net Intensity | Gross Intensity | Rel. Intensity |
|---|---|---|---|---|---|
| 19 | 18.397° | 4.81884 A | 586.508 | 775.013 | 79.8% |
| 20 | 18.616° | 4.76266 A | 735.061 | 924.123 | 100.0% |
| 21 | 19.616° | 4.52185 A | 208.661 | 395.877 | 28.4% |
| 33 | 20.11° | 4.28409 A | 69.4470 | 252.011 | 9.4% |
| 23 | 21.435° | 4.14210 A | 155.825 | 336.360 | 21.2% |
| 24 | 22.175° | 4.00564 A | 76.9573 | 251.528 | 10.5% |
| 25 | 22.956° | 3.87107 A | 61.4421 | 232.682 | 8.4% |
| 26 | 24.226° | 3.67091 A | 77.6650 | 242.971 | 10.6% |
| 27 | 25.300° | 3.51748 A | 53.0406 | 204.275 | 7.2% |
| 28 | 25.964° | 3.42896 A | 67.3128 | 205.687 | 9.2% |
| 29 | 27.961° | 3.18845 A | 65.3500 | 178.917 | 8.9% |
| 30 | 29.229° | 3.05295 A | 30.9502 | 139.437 | 4.2% |
| 31 | 30.52° | 2.92615 A | 26.0676 | 128.990 | 3.5% |
| 32 | 31.640° | 2.82562 A | 17.2880 | 121.439 | 2.4% |
| 33 | 33.632° | 2.66261 A | 43.3283 | 145.288 | 5.9% |
| 34 | 34.500° | 2.59759 A | 30.0408 | 129.000 | 4.1% |

*±0.1°

In some embodiments, Form E has an X-ray powder diffraction (XRPD) pattern with characteristic peaks at 4±0.1° 2-Theta, 4.7±0.1° 2-Theta, 6.3±0.1° 2-Theta, 6.9±0.1° 2-Theta, 7.1±0.1° 2-Theta, 7.6±0.1° 2-Theta, 8.6±0.1° 2-Theta, 9.3±0.1° 2-Theta, 10.8±0.1° 2-Theta, 12±0.1° 2-Theta, 12.5±0.1° 2-Theta, 13±0.1° 2-Theta, 13.8±0.1° 2-Theta, 15.7±0.1° 2-Theta, 16.2±0.10° 2-Theta, 16.7±0.10° 2-Theta, 17±0.10° 2-Theta, 17.5±0.10° 2-Theta, 18.4±0.10° 2-Theta, 18.6±0.10° 2-Theta, 19.6±0.10° 2-Theta, 20.7±0.10° 2-Theta, 21.4±0.10° 2-Theta, 22.2±0.10° 2-Theta, 23±0.1° 2-Theta, 24.2±0.1° 2-Theta, 25.3±0.1° 2-Theta, 26±0.1° 2-Theta, 28±0.1° 2-Theta, 29.2±0.1° 2-Theta, 30.5±0.1° 2-Theta, 31.6±0.1° 2-Theta, 33.6±0.1° 2-Theta, and 34.5±0.1° 2-Theta.

In some embodiments, Form E has an X-ray powder diffraction (XRPD) pattern with characteristic peaks at 4.7±0.1° 2-Theta, 7.7±0.1° 2-Theta, 10.8±0.1° 2-Theta, 13.8±0.1° 2-Theta, 17.0±0.1° 2-Theta, 18.4±0.1° 2-Theta, and 18.6±0.1° 2-Theta.

In some embodiments, Form E has a DSC thermogram with an endotherm having an onset at about 112.34° C. and a peak at about 137.26° C.

In some embodiments, Form E is hygroscopic.

Form F

In one particular aspect, described herein is a Form F of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A) that has at least one of the following properties:

(a) an X-ray powder diffraction (XRPD) pattern substantially the same as shown in FIG. 6A;

(b) an X-ray powder diffraction (XRPD) pattern with characteristic peaks at, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, or thirty-two of 4.2±0.1° 2-Theta, 6.3±0.1° 2-Theta, 8.6±0.1° 2-Theta, 8.8±0.1° 2-Theta, 12±0.1° 2-Theta, 12.2±0.1° 2-Theta, 12.5±0.1° 2-Theta, 14.4±0.1° 2-Theta, 15±0.1° 2-Theta, 16±0.1° 2-Theta, 16.8±0.1° 2-Theta, 17.2±0.1° 2-Theta, 17.5±0.1° 2-Theta, 17.8±0.1° 2-Theta, 18.8±0.1° 2-Theta, 19.2±0.1° 2-Theta, 20.1±0.1° 2-Theta, 20.5±0.1° 2-Theta, 21.7±0.1° 2-Theta, 22.1±0.1° 2-Theta, 23.4±0.1° 2-Theta, 24.2±0.1° 2-Theta, 25.3±0.1° 2-Theta, 25.5±0.1° 2-Theta, 26.3±0.1° 2-Theta, 27.1±0.1° 2-Theta, 29±0.1° 2-Theta, 30.3±0.1° 2-Theta, 31.6±0.1° 2-Theta, 33.1±0.1° 2-Theta, 34.3±0.1° 2-Theta, and 35.6±0.1° 2-Theta;

(c) an X-ray powder diffraction (XRPD) pattern with characteristic peaks at 6.3±0.1° 2-Theta, 8.6±0.1° 2-Theta, 8.8±0.1° 2-Theta, 11.9±0.1° 2-Theta, 12.2±0.1° 2-Theta, 14.4±0.1° 2-Theta, 15.0±0.1° 2-Theta, and 20.5±0.1° 2-Theta;

or (d) combinations thereof.

In some embodiments, Form F is a crystalline form.

In some embodiments, Form F is a solvate. In some embodiments, Form F is a heteo solvate. In some embodiments, Form F is a disolvate. In some embodiments, Form F is a MeGH and DCM (1:1) hetero-solvate or disolvate.

In some embodiments, Form F has an X-ray powder diffraction (XRPD) pattern substantially the same as shown in FIG. 6A.

In some embodiments, Form F has an X-ray powder diffraction (XRPD) pattern substantially the same as shown below:

TABLE F

XRPD Pattern of Free Form Pattern F
(Compound A, Form F)

| Index | Angle* | dValue | Net Intensity | Gross Intensity | Rel. Intensity |
|---|---|---|---|---|---|
| 1 | 4.421° | 20.91462 A | 116.3237 | 87.3639 | 1.8% |
| 2 | 6.281° | 14.05959 A | 405.346 | 477.688 | 43.7% |
| 3 | 8.561° | 10.32057 A | 372.008 | 460.190 | 40.1% |
| 4 | 8.786° | 10.05676 A | 368.812 | 457.922 | 39.7% |
| 5 | 11.904° | 7.42871 A | 927.836 | 1043.85 | 100.0% |
| 6 | 12.161° | 7.27219 A | 623.900 | 741.888 | 67.2% |
| 7 | 12.482° | 7.08564 A | 350.836 | 470.673 | 37.8% |
| 8 | 14.411° | 6.1442 A | 530.623 | 668.184 | 57.2% |
| 9 | 15.022° | 5.89308 A | 510.988 | 653.688 | 55.1% |
| 10 | 15.954° | 5.55079 A | 180.999 | 326.786 | 19.5% |
| 11 | 16.774° | 5.28110 A | 40.0577 | 183.806 | 4.3% |
| 12 | 17.171° | 5.15999 A | 57.5230 | 201.798 | 6.2% |
| 13 | 17.529° | 5.05542 A | 1169.685 | 317.535 | 18.3% |
| 14 | 17.786° | 4.98290 A | 1143.213 | 293.107 | 15.4% |
| 15 | 18.792° | 4.71841 A | 1153.791 | 307.481 | 16.61% |
| 16 | 19.1168° | 4.62660 A | 91.9137 | 245.305 | 9.9% |
| 17 | 20.068° | 4.42109 A | 199.462 | 355.009 | 21.5% |
| 18 | 20.486° | 4.331185 A | 393.366 | 549.624 | 42.41% |
| 19 | 21.692° | 4.09361 A | 186.510 | 338.341 | 20.1% |
| 20 | 22.061° | 4.02601 A | 80.6176 | 229.174 | 8.7% |
| 21 | 23.411° | 3.79681 A | 240.104 | 394.409 | 25.9% |
| 22 | 24.182° | 3.67741 A | 228.495 | 390.682 | 24.6% |
| 23 | 25.275° | 3.52082 A | 220.009 | 386.624 | 23.7% |
| 24 | 25.532° | 3.48594 A | 1182.510 | 349.021 | 19.7% |
| 25 | 26.334° | 3.38157 A | 53.8584 | 217.224 | 5.8% |
| 26 | 27.107° | 3 28687 A | 68.0545 | 224.365 | 7.3% |
| 27 | 27.429° | 3.24908 A | 95.1971 | 247.410 | 10.3% |
| 28 | 27.686° | 3.21948 A | 122.467 | 270.911 | 13.2% |
| 29 | 28.972° | 3.07946 A | 84.0006 | 209.058 | 9.1% |
| 30 | 30.322° | 2.94536 A | 41.0037 | 156.840 | 4.4% |
| 31 | 31.64° | 2.82562 A | 18.3329 | 126.702 | 2.0% |
| 32 | 33.067° | 2.70680 A | 37.5462 | 150.489 | 4.0% |
| 33 | 34.275° | 2.61412 A | 25.5112 | 140.543 | 2.7% |
| 34 | 35.761° | 2.52250 A | 112.6371 | 120.689 | 1.4% |

*±0.1°

In some embodiments, Form F has an X-ray powder diffraction (XRPD) pattern with characteristic peaks at 4.2±0.1° 2-Theta, 6.3±0.1° 2-Theta, 8.6±0.1° 2-Theta, 8.8±0.1° 2-Theta, 12±0.1° 2-Theta, 12.2±0.1° 2-Theta, 12.5±0.1° 2-Theta, 14.4±0.1° 2-Theta, 15±0.1° 2-Theta, 16±0.1° 2-Theta, 16.8±0.1° 2-Theta, 17.2±0.1° 2-Theta, 17.5±0.1° 2-Theta, 17.8±0.1° 2-Theta, 18.8±0.1° 2-Theta, 19.2±0.1° 2-Theta, 20.1±0.1° 2-Theta, 20.5±0.1° 2-Theta, 21.7±0.1° 2-Theta, 22.1±0.1° 2-Theta, 23.4±0.1° 2-Theta, 24.2±0.1° 2-Theta, 25.3±0.1° 2-Theta, 25.5±0.1° 2-Theta, 26.3±0.1° 2-Theta, 27.1±0.1° 2-Theta, 29±0.1° 2-Theta, 30.3±0.1° 2-Theta, 31.6±0.1° 2-Theta, 33.1±0.1° 2-Theta, 34.3±0.1° 2-Theta, and 35.6±0.1° 2-Theta.

In some embodiments, Form F has an X-ray powder diffraction (XRPD) pattern with characteristic peaks at 6.3±0.1° 2-Theta, 8.6±0.1° 2-Theta, 8.8±0.1° 2-Theta, 11.9±0.1° 2-Theta, 12.2±0.1° 2-Theta, 14.4±0.1° 2-Theta, 15.0±0.1° 2-Theta, and 20.5±0.1° 2-Theta.

In some embodiments, Form F is hygroscopic.

Form G

In one particular aspect, described herein is a Form G of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A) that has at least one of the following properties:
(a) an X-ray powder diffraction (XRPD) pattern substantially the same as shown in FIG. 7A;
(b) an X-ray powder diffraction (XRPD) pattern with characteristic peaks at one, two, three, four, five, or six of 8±0.1° 2-Theta, 10.2±0.1° 2-Theta, 12.1±0.1° 2-Theta, 16.8±0.1° 2-Theta, 19.2±0.1° 2-Theta, and 24.6±0.1° 2-Theta;
(c) an X-ray powder diffraction (XRPD) pattern with characteristic peaks at 8.1±0.1° 2-Theta, 10.2±0.1° 2-Theta, 12.1±0.1° 2-Theta, 16.8±0.1° 2-Theta, 19.2±0.1° 2-Theta, and 24.6±0.1° 2-Theta;
or
(d) combinations thereof.

In some embodiments, Form G is a crystalline form. In some embodiments, Form G is a TFE solvate.

In some embodiments, Form G has an X-ray powder diffraction (XRPD) pattern substantially the same as shown in FIG. 7A.

In some embodiments, Form G has an X-ray powder diffraction (XRPD) pattern substantially the same as shown below:

TABLE G

XRPD Pattern of Free Form Pattern G (Compound A, Form G)

| Index | Angle* | dValue | Net Intensity | Gross Intensity | Rel. Intensity |
|---|---|---|---|---|---|
| 1 | 8.046° | 10.97902 A | 76.8302 | 160.625 | 39.9% |
| 2 | 10.200° | 8.66528 A | 36.4001 | 137.004 | 18.9% |
| 3 | 12.097° | 7.31070 A | 40.5158 | 152.039 | 21.0% |
| 4 | 16.789° | 5.27632 A | 58.8715 | 208.042 | 30.6% |
| 5 | 19.168° | 4.62660 A | 94.3343 | 269.130 | 49.0% |
| 6 | 24.568° | 3.62054 A | 192.545 | 347.027 | 100.0% |

*±0.1°

In some embodiments, Form G has an X-ray powder diffraction (XRPD) pattern with characteristic peaks at 8.1±0.1° 2-Theta, 10.2±0.1° 2-Theta, 12.1±0.1° 2-Theta, 16.8±0.1° 2-Theta, 19.2±0.1° 2-Theta, and 24.6±0.1° 2-Theta.

In some embodiments, Form G is hygroscopic.

Form J

In one particular aspect, described herein is a Form J of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A) that has at least one of the following properties:
(a) an X-ray powder diffraction (XRPD) pattern substantially the same as shown in FIG. 8A;
(b) an X-ray powder diffraction (XRPD) pattern with characteristic peaks at one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, or forty-four of 3.5±0.1° 2-Theta, 4.5±0.1° 2-Theta, 6.4±0.1° 2-Theta, 8.7±0.1° 2-Theta, 10.2±0.1° 2-Theta, 11.3±0.1° 2-Theta, 11.8±0.1° 2-Theta, 13.2±0.1° 2-Theta, 13.6±0.1° 2-Theta, 14±0.1° 2-Theta, 14.6±0.1° 2-Theta, 15.4±0.1° 2-Theta, 16.1±0.1° 2-Theta, 16.6±0.1° 2-Theta, 16.9±0.1° 2-Theta, 17.2±0.1° 2-Theta, 18.3±0.1° 2-Theta, 19.1±0.1° 2-Theta, 20.5±0.1° 2-Theta, 20.8±0.1° 2-Theta, 21.6±0.1° 2-Theta, 23.5±0.1° 2-Theta, 23.8±0.1° 2-Theta, 24.6±0.1° 2-Theta, 24.9±0.1° 2-Theta, 25.2±0.1° 2-Theta, 25.8±0.1° 2-Theta, 26.2±0.1° 2-Theta, 26.7±0.1° 2-Theta, 26.8±0.1° 2-Theta, 27.4±0.1° 2-Theta, 27.7±0.1° 2-Theta, 28.7±0.1° 2-Theta, 29.3±0.1° 2-Theta, 30.1±0.1° 2-Theta, 31.2±0.1° 2-Theta, 31.8±0.1° 2-Theta, 34.1±0.1° 2-Theta, 34.9±0.1° 2-Theta, 35.6±0.1° 2-Theta, 36.4±0.1° 2-Theta, 36.7±0.1° 2-Theta, 38.5±0.1° 2-Theta, and 38.8±0.1° 2-Theta;
(c) an X-ray powder diffraction (XRPD) pattern with characteristic peaks at 3.5±0.1° 2-Theta, 4.5±0.1° 2-Theta, 19.1±0.1° 2-Theta, 21.6±0.1° 2-Theta, 22.5±0.1° 2-Theta, and 27.4±0.1° 2-Theta;
(d) an observed hygroscopicity and absorption of about 2.1% water from 40% RH to 70% RH at 25° C.
(e) an observed aqueous solubility of about 0.004 mg/mL at about pH 4.5;
or
(f) combinations thereof.

In some embodiments, Form J is a crystalline form. In some embodiments, Form J is an anhydrate.

In some embodiments, Form J has an X-ray powder diffraction (XRPD) pattern substantially the same as shown in FIG. 8A.

In some embodiments, Form J has an X-ray powder diffraction (XRPD) pattern with characteristic peaks at 3.5±0.1° 2-Theta, 4.5±0.1° 2-Theta, 6.4±0.1° 2-Theta, 8.7±0.1° 2-Theta, 10.2±0.1° 2-Theta, 11.3±0.1° 2-Theta, 11.8±0.1° 2-Theta, 13.2±0.1° 2-Theta, 13.6±0.1° 2-Theta, 14±0.1° 2-Theta, 14.6±0.1° 2-Theta, 15.4±0.1° 2-Theta, 16.1±0.1° 2-Theta, 16.6±0.1° 2-Theta, 16.9±0.1° 2-Theta, 17.2±0.1° 2-Theta, 18.3±0.1° 2-Theta, 19.1±0.1° 2-Theta, 20.5±0.1° 2-Theta, 20.8±0.1° 2-Theta, 21.6±0.1° 2-Theta, 23.5±0.1° 2-Theta, 23.8±0.1° 2-Theta, 24.6±0.1° 2-Theta, 24.9±0.1° 2-Theta, 25.2±0.1° 2-Theta, 25.8±0.1° 2-Theta, 26.2±0.1° 2-Theta, 26.7±0.1° 2-Theta, 26.8±0.1° 2-Theta, 27.4±0.1° 2-Theta, 27.7±0.1° 2-Theta, 28.7±0.1° 2-Theta, 29.3±0.1° 2-Theta, 30.1±0.1° 2-Theta, 31.2±0.1° 2-Theta, 31.8±0.1° 2-Theta, 34.1±0.1° 2-Theta, 34.9±0.1° 2-Theta, 35.6±0.1° 2-Theta, 36.4±0.1° 2-Theta, 36.7±0.1° 2-Theta, 38.5±0.1° 2-Theta, and 38.8±0.1° 2-Theta.

In some embodiments, Form J has an X-ray powder diffraction (XRPD) pattern with characteristic peaks at 3.5±0.1° 2-Theta, 4.5±0.1° 2-Theta, 19.1±0.1° 2-Theta, 21.6±0.1° 2-Theta, 22.5±0.1° 2-Theta, and 27.4±0.1° 2-Theta.

In some embodiments, Form J is hygroscopic.

Formulation

In another aspect, provided herein is a pharmaceutical formulation for oral administration comprising:
(a) about 10 mg to about 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 50 wt % to about 80 wt % of one or more diluents;
(c) about 1 wt % to about 10 wt % of one or more disintegrating agents;
(d) about 0.2 wt % to about 3 wt % of one or more glidants; and
(e) about 0.2 wt % to about 1.0 wt % of one or more lubricants.

In some embodiments, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments, the diluent is pregelatinized maize starch and lactose. In some embodiments, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments, the disintegrating agent is crospovidone. In some embodiments, the glidant is selected from the group consisting of ascorbyl palmitate, calcium palmitate, magnesium stearate, fumed silica, starch, and talc. In some embodiments, the glidant is fumed silica. In some embodiments, the lubricant is selected from the group consisting of stearic acid, calcium hydroxide, talc, corn starch, sodium stearyl fumarate, stearic acid, sodium stearates, magnesium stearate, zinc stearate, and waxes. In some embodiments, the lubricant is magnesium stearate.

In some embodiments, provided herein is a pharmaceutical formulation for oral administration comprising:
(a) about 10 mg to about 500 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 20 wt % to about 80 wt % total of pregelatinized maize starch and lactose;
(c) about 3 wt % to about 10 wt % of crospovidone;
(d) about 0.1 wt % to about 1.0 wt % of fumed silica; and
(e) about 0.1 wt % to about 1.0 wt % of magnesium stearate.

In some embodiments, provided herein is a pharmaceutical formulation for oral administration comprising:
(a) about 10 mg to about 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 70 wt % to about 80 wt % total of pregelatinized maize starch and lactose;
(c) about 3 wt % to about 10 wt % of crospovidone;
(d) about 0.1 wt % to about 1.0 wt % of fumed silica; and
(e) about 0.1 wt % to about 1.0 wt % of magnesium stearate.

In some embodiments, provided herein is a pharmaceutical formulation for oral administration comprising:
(a) about 10 wt % to about 30 wt % of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 25 wt % to about 65 wt % of pregelatinized maize starch and about 25 wt % to about 40 wt % of lactose;
(c) about 1 wt % to about 10 wt % of crospovidone;
(d) about 0.1 wt % to about 1.0 wt % of fumed silica; and
(e) about 0.1 wt % to about 1.0 wt % of magnesium stearate.

In some embodiments, provided herein is a pharmaceutical formulation for oral administration comprising:
(a) about 10 wt % to about 25 wt % of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 25 wt % to about 60 wt % of pregelatinized maize starch and about 25 wt % to about 40 wt % of lactose;
(c) about 1 wt % to about 10 wt % of crospovidone;
(d) about 0.1 wt % to about 1.0 wt % of fumed silica; and
(e) about 0.1 wt % to about 1.0 wt % of magnesium stearate.

In some embodiments, provided herein is a pharmaceutical formulation for oral administration comprising:
(a) about 25, 50, 100, 150, 200, or 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 37 wt % of pregelatinized maize starch (Starch 1500);
(c) about 36% of lactose (FastFlo Lactose 316);
(d) about 5 wt % of crospovidone;
(e) about 1 wt % of fumed silica; and
(f) about 0.5 wt % of magnesium stearate.

In some embodiments, provided herein is a pharmaceutical formulation for oral administration comprising:
(a) about 25, 50, 100, 150, 200, or 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 52 wt % of pregelatinized maize starch (Starch 1500);
(c) about 27% of lactose (FastFlo Lactose 316);
(d) about 4 wt % of crospovidone;
(e) about 0.8 wt % of fumed silica; and
(f) about 0.4 wt % of magnesium stearate.

In some embodiments, provided herein is a pharmaceutical formulation for oral administration comprising:
(a) about 25, 50, 100, 150, 200, or 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 21 wt % of pregelatinized maize starch (Starch 1500);
(c) about 37% of lactose (FastFlo Lactose 316);
(d) about 5 wt % of crospovidone;
(e) about 1 wt % of fumed silica; and
(f) about 0.5 wt % of magnesium stearate.

In some embodiments, provided herein is a pharmaceutical formulation for oral administration comprising:
(a) about 25, 50, 100, 150, 200, or 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;

(b) about 28 wt % of pregelatinized maize starch (Starch 1500);
(c) about 27% of lactose (FastFlo Lactose 316);
(d) about 4 wt % of crospovidone;
(e) about 0.8 wt % of fumed silica; and
(f) about 0.4 wt % of magnesium stearate.

In certain embodiments, the pharmaceutical formulations are substantially homogenous. In certain embodiments, the pharmaceutical formulations are granular. In certain embodiments, the intragranular composition is according to one of the embodiments above. In certain embodiments, the extragranular composition comprises pregelatinized maize starch, e.g. Starch 1500.

In some embodiments, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments the diluent is pregelatinized maize starch and lactose. In some embodiments, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments, the disintegrating agent is crospovidone. In some embodiments, the glidant is selected from the group consisting of ascorbyl palmitate, calcium palmitate, magnesium stearate, fumed silica, starch, and talc. In some embodiments, the surfactant is sodium lauryl sulfate. In some embodiments, the lubricant is selected from the group consisting of stearic acid, calcium hydroxide, talc, corn starch, sodium stearyl fumarate, stearic acid, sodium stearates, magnesium stearate, zinc stearate, and waxes. In some embodiments, the lubricant is magnesium stearate.

In some embodiments, provided herein is a pharmaceutical formulation for oral administration comprising:
(a) about 10 mg to about 250 mg of crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 70 wt % to about 80 wt % of pregelatinized maize starch and lactose;
(c) about 5 wt % of crospovidone;
(d) about 0.5 wt % to 1 wt % of fumed silica; and
(e) about 0.2 wt % to 0.5 wt % of magnesium stearate.

In some embodiments, provided herein is a pharmaceutical formulation for oral administration comprising:
(a) about 10 wt % to about 25 wt % of crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 70 wt % to about 80 wt % of pregelatinized maize starch and lactose;
(c) about 5 wt % of crospovidone;
(d) about 0.5 wt % to 1 wt % of fumed silica; and
(e) about 0.2 wt % to 0.5 wt % of magnesium stearate.

In some embodiments, provided herein is a pharmaceutical formulation for oral administration comprising:
(a) about 25 mg of crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 70 wt % to about 80 wt % of pregelatinized maize starch and lactose;
(c) about 5 wt % of crospovidone;
(d) about 0.5 wt % to 1 wt % of fumed silica; and
(e) about 0.2 wt % to 0.5 wt % of magnesium stearate.

In some embodiments, provided herein is a pharmaceutical formulation for oral administration comprising:
(a) about 100 mg of crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
(b) about 70 wt % to about 80 wt % of pregelatinized maize starch and lactose;
(c) about 5 wt % of crospovidone;
(d) about 0.5 wt % to 1 wt % of fumed silica; and
(e) about 0.2 wt % to 0.5 wt % of magnesium stearate.

In some embodiments of the aforementioned pharmaceutical formulation embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]-2-pyridinecarboxamide is crystalline Form A. In some embodiments of the aforementioned pharmaceutical formulation embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is crystalline Form B. In some embodiments of the aforementioned pharmaceutical formulation embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is crystalline Form C. In some embodiments of the aforementioned pharmaceutical formulation embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is crystalline Form D. In some embodiments of the aforementioned pharmaceutical formulation embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is crystalline Form E. In some embodiments of the aforementioned pharmaceutical formulation embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is crystalline Form F. In some embodiments of the aforementioned pharmaceutical formulation embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is crystalline Form G. In some embodiments of the aforementioned pharmaceutical formulation embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is crystalline Form J. In some embodiments of the aforementioned pharmaceutical formulation embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is a mixture of two or more crystalline forms selected from the group consisting of Form A, Form B, Form C, Form D, Form E, Form F, Form G, and Form J.

In another embodiment of the aforementioned pharmaceutical formulation embodiments provided herein, is a pharmaceutical formulation wherein the dosage form is a hard gelatin capsule.

In another aspect, provided herein is a pharmaceutical formulation for oral administration comprising:
  (a) about 10 mg to about 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide as a crystalline Form A;
  (b) about 50 wt % to about 80 wt % of one or more diluents;
  (c) about 1 wt % to about 10 wt % of one or more disintegrating agents;
  (d) about 0.2 wt % to about 3 wt % of one or more glidants; and
  (e) about 0.2 wt % to about 1.0 wt % of one or more lubricants.

In some embodiments, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments the diluent is microcrystalline cellulose. In some embodiments, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments, the disintegrating agent is croscarmellose sodium. In some embodiments, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments, the surfactant is sodium lauryl sulfate. In some embodiments, the lubricant is selected from the group consisting of stearic acid, calcium hydroxide, talc, corn starch, sodium stearyl fumarate, stearic acid, sodium stearates, magnesium stearate, zinc stearate, and waxes. In some embodiments, the lubricant is magnesium stearate.

In some embodiments, provided herein is a pharmaceutical formulation for oral administration comprising:
  (a) about 10 mg to about 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide as a crystalline Form D;
  (b) about 70 wt % to about 80% wt % of pregelatinized maize starch and lactose;
  (c) about 5 wt % of crospovidone;
  (d) about 0.5 wt % to 1 wt % of fumed silica; and
  (e) about 0.2 wt % to 0.5 wt % of magnesium stearate.

In some embodiments, provided herein is a pharmaceutical formulation for oral administration comprising:
  (a) about 10 wt % to about 25 wt % of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide as a crystalline Form D;
  (b) about 37.2 wt % of pregelatinized maize starch and about 35.6% lactose;
  (c) about 5 wt % of crospovidone;
  (d) about 1 wt % of fumed silica; and
  (e) about 0.5 wt % of magnesium stearate.

In some embodiments, provided herein is a pharmaceutical formulation for oral administration comprising:
  (a) about 10 wt % to about 25 wt % of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide as a crystalline Form D;
  (b) about 52 wt % of pregelatinized maize starch and about 27.3% lactose;
  (c) about 3.8 wt % of crospovidone;
  (d) about 0.8 wt % of fumed silica; and
  (e) about 0.4 wt % of magnesium stearate.

In some embodiments, provided herein is a pharmaceutical formulation for oral administration comprising:
  (a) 25 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide as a crystalline Form D;
  (b) about 45.2 mg pregelatinized maize starch and about 43.44 mg lactose;
  (c) about 6.1 mg of crospovidone;
  (d) about 1.2 mg of fumed silica; and
  (e) about 0.61 mg of magnesium stearate.

In some embodiments, provided herein is a pharmaceutical formulation for oral administration comprising:
  (a) 100 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide as a crystalline Form D;
  (b) about 330.6 mg pregelatinized maize starch and about 173.8 mg lactose;
  (c) about 24.3 mg of crospovidone;
  (d) about 4.9 mg of fumed silica; and
  (e) about 2.4 mg of magnesium stearate.

In another aspect provided herein, is a pharmaceutical formulation comprising: a) about 10 mg to about 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide; b) about 50 wt % to about 80 wt % of one or more diluents; c) about 1 wt % to about 10 wt % of a disintegrating agent; d) about 0.2 wt % to about 3 wt % of a glidant; and e) about 0.2 wt % to about 1.0 wt % of a lubricant; wherein the formulation is in a unit dosage form in a bottle or a blister pack. In certain embodiments, the dosage form is in a blister pack, and said blister pack comprises metal or plastic foil. In some embodiments, provided is a pharmaceutical formulation comprising:
  (a) 25 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
  (b) about 37.2 wt % of pregelatinized maize starch and about 35.6% lactose;
  (c) about 5 wt % of crospovidone;
  (d) about 1 wt % of fumed silica; and
  (e) about 0.5 wt % of magnesium stearate. wherein the formulation is in a unit dosage form in a bottle or a blister pack. In certain embodiments, the dosage form is in a blister pack, and said blister pack comprises metal or plastic foil. In some embodiments, provided is a pharmaceutical formulation comprising: a) 100 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide; (b) about 330.6 mg pregelatinized maize starch and about 173.8 mg lactose;

(c) about 24.3 mg of crospovidone;
(d) about 4.9 mg of fumed silica; and
(e) about 2.4 mg of magnesium stearate.
wherein the formulation is in a unit dosage form in a bottle or a blister pack. In certain embodiments, the dosage form is in a blister pack, and said blister pack comprises metal or plastic foil.

In another embodiment is a package comprising one or more discrete blister pockets, wherein each blister pocket comprises a unit dosage form comprising:
  a) about 10 mg to about 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
  (b) about 50 wt % to about 80 wt % of one or more diluents;
  (c) about 1 wt % to about 10 wt % of one or more disintegrating agents;
  (d) about 0.2 wt % to about 3 wt % of one or more glidants; and
  (e) about 0.2 wt % to about 1.0 wt % of one or more lubricants.
wherein each blister pocket comprises metal or plastic foil.

In another aspect provided herein, is a pharmaceutical formulation comprising:
  a) about 10 mg to about 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide as a crystalline Form A;
  (b) about 50 wt % to about 80 wt % of one or more diluents;
  (c) about 1 wt % to about 10 wt % of one or more disintegrating agents;
  (d) about 0.2 wt % to about 3 wt % of one or more glidants; and
  (e) about 0.2 wt % to about 1.0 wt % of one or more lubricants.
wherein the formulation is in a unit dosage form in a bottle or a blister pack In certain embodiments, the dosage form is in a blister pack, and said blister pack comprises metal or plastic foil. In some embodiments, provided is a pharmaceutical formulation comprising:
  a) 25 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide;
  (b) about 37.2 wt % of pregelatinized maize starch and about 35.6% lactose;
  (c) about 5 wt % of crospovidone;
  (d) about 1 wt % of fumed silica; and
  (e) about 0.5 wt % of magnesium stearate;
    wherein the formulation is in a unit dosage form in a bottle or a blister pack. In certain embodiments, the dosage form is in a blister pack, and said blister pack comprises metal or plastic foil. In some embodiments, provided is a pharmaceutical formulation comprising:
  a) 100 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide; (b) about 52 wt % of pregelatinized maize starch and about 27.3% lactose;
  (c) about 3.8 wt % of crospovidone;
  (d) about 0.8 wt % of fumed silica; and
  (e) about 0.4 wt % of magnesium stearate.
wherein the formulation is in a unit dosage form in a bottle or a blister pack. In certain embodiments, the dosage form is in a blister pack, and said blister pack comprises metal or plastic foil.

In another embodiment is a package comprising one or more discrete blister pockets, wherein each blister pocket comprises a unit dosage form comprising:
  a) about 10 mg to about 250 mg of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide as a crystalline Form A;
  (b) about 50 wt % to about 80 wt % of one or more diluents;
  (c) about 1 wt % to about 10 wt % of one or more disintegrating agents;
  (d) about 0.2 wt % to about 3 wt % of one or more glidants; and
  (e) about 0.2 wt % to about 1.0 wt % of one or more lubricants.
wherein each blister pocket comprises metal or plastic foil.

In one embodiment, a kit is provided which contains a multiplicity of oral dosage forms, such as tablets or capsules; packaging such as a jar containing the oral dosage forms; and instructions for use to administer the oral dosage forms in accordance with the method(s) described herein. Unit dose packaging such as blister packs provide a useful way of packaging the oral dosage form of the formulations described herein, and in other embodiments embody a kit when combined with instructions for use. In other embodiments, detailed product information is included with the instructions for use in the kit. Blister packaging is particularly useful with solid oral dosage forms and in further embodiments is, for example, useful for alternate day dosing schedules. In one embodiment, solid unit dosage forms of the formulations described herein are included in a blister pack with instructions to administer one or more tablets or capsules on a daily basis so that the dosage of the formulations described herein are sufficiently administered. In another embodiment, solid unit dosage forms are included in a blister pack with instructions to administer one or more tablets or capsules on an alternating daily basis so that the dosage per day is sufficiently administered.

In one aspect, provided herein are methods for treating a patient by administering Compound A. In some embodiments, provided herein is a method of inhibiting the menin-MLL interaction or a method of treating a disease, disorder, or condition, which would benefit from inhibition of menin-MLL interaction, in a mammal, which includes administering to the mammal a therapeutically effective amount of Compound A, or pharmaceutically acceptable salt, pharmaceutically active metabolite, pharmaceutically acceptable prodrug, or pharmaceutically acceptable solvate.

In another aspect, provided herein is the use of Compound A for inhibiting menin-HLL interaction or for the treatment of a disease, disorder, or condition, which would benefit from inhibition of the menin-MLL interaction.

In another aspect, provided herein is the use of Compound A for treating a KRAS mutation cancer in a mammal. In certain embodiments, the cancer is a solid tumor. In certain embodiments, the KRAS mutation is a KRAS G12 mutation. In certain embodiments, the KRAS mutation is a KRAS G12C, G12V, G13D, or G12D mutation. In certain embodiments, the KRAS mutation is G12C mutation. In certain embodiments, the KRAS mutation is G12V mutation. In certain embodiments, the KRAS mutation is G13D mutation. In certain embodiments, the KRAS mutation is G12D mutation. In certain embodiments, Compound A is in a form or pharmaceutical formulation as described elsewhere herein.

In another aspect, provided herein is the use of Compound A for treating a cancer in a mammal (e.g., human patient) who does not exhibit a KRAS mutation.

In another aspect, provided herein is the use of Compound A for treating diffuse large B-cell lymphoma in a mammal (e.g., human patient). In certain embodiments, the mammal has triple-hit lymphoma. In certain embodiments, the mammal has double expresser lymphoma. In certain embodiments, the mammal has multiple myeloma. In certain embodiments, Compound A is in a form or pharmaceutical formulation as described elsewhere herein.

In certain embodiments, Compound A is in a crystalline Form D.

In certain embodiments, the mammal (e.g., patient) has Double Hit Lymphoma (DHL).

In certain embodiments, the mammal (e.g., patient) has Triple Hit Lymphoma (THL).

In certain embodiments, the mammal (e.g., patient) has Double Expressor Lymphoma (DEL).

In another aspect, provided herein is the use of Compound A for treating diffuse multiple myeloma in a mammal (e.g., human patient). In certain embodiments, Compound A is in a form or pharmaceutical formulation as described elsewhere herein.

In some embodiments, crystalline Compound A is administered to a human.

In some embodiments, crystalline Compound A is orally administered.

In other embodiments, crystalline Compound A is used for the formulation of a medicament for the inhibition of menin-MLL interaction. In some other embodiments, crystalline Compound A is used for the formulation of a medicament for the inhibition of menin-MLL interaction.

In one aspect, provided herein is a method of treating cancer in a mammal comprising administering to the mammal a pharmaceutical composition described herein further comprising Compound A. In some embodiments, the cancer is a B cell malignancy. In some embodiments, the cancer is a B cell malignancy selected from chronic lymphocytic leukemia (CLL)/small lymphocytic lymphoma (SLL), mantle cell lymphoma (MCL), diffuse large B cell lymphoma (DLBCL), and multiple myeloma. In some embodiments, the cancer is acute myeloid leukemia (AML). In some embodiments, the cancer is acute lymphoblastic leukemia (ALL). In some embodiments, the mammal or subject has an MLL/KMT2A gene rearrangement. In some embodiments, the mammal or subject has an ATM mutation. In some embodiments, the mammal or subject has an NPM1 mutation. In some embodiments, the mammal or subject has a TP53 mutation. In some embodiments, the mammal or subject has a NOTCH1 mutation. In some embodiments, the mammal or subject has a WT1 mutation. In some embodiments, the mammal or subject has a RAS mutation. In some embodiments, the mammal or subject has a KRAS mutation. In some embodiments, the mammal or subject has a KRAS G12C mutation. In some embodiments, the mammal or subject has a KRAS G12D mutation. In some embodiments, the mammal or subject has a KRAS G12V mutation. In some embodiments, the mammal or subject has a KRAS G13D mutation. In some embodiments, the mammal or subject has a TET2 mutation. In some embodiments, the mammal or subject has a MYC amplification. In some embodiments, the mammal or subject has a del(13q) karyotype. In some embodiments, the mammal or subject has a trisomy 12 karyotype. In some embodiments, the cancer is a lymphoma, leukemia, or a solid tumor. In some embodiments, the cancer is diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the mammal or subject is suffering from a cancer, an anti-cancer agent is administered to the mammal or subject in addition to one of the above-mentioned compounds or embodiments. In one embodiment, the anti-cancer agent is an inhibitor of mitogen-activated protein kinase signaling.

In one aspect, provided herein is a method of treating an inflammatory or an autoimmune disease in a mammal comprising administering to the mammal a pharmaceutical composition described herein comprising Compound A. In some embodiments, the inflammatory disease is asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis. In some embodiments, the autoimmune disease is inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjögren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behget's disease, chronic fatigue, dysautonomia, endometriosis, interstitial cystitis, neuromyotonia, scleroderma, or vulvodynia Articles of manufacture including packaging material, Compound A within the packaging material, and a label that indicates that Compound A is used for inhibiting the activity of menin-MLL, are provided.

In a further aspect, provided herein is a method of treating an autoimmune disease in a mammal, comprising administering Compound A to the mammal.

In a further aspect, provided herein is a method of treating a heteroimmune disease or condition in a mammal, comprising administering Compound A to the mammal.

In a further aspect, provided herein is a method of treating an inflammatory disease in a mammal, comprising administering Compound A to the mammal.

In a further aspect, provided herein is a method of treating cancer in a mammal, comprising administering Compound A to the mammal.

In a further aspect, provided herein is a method of treating a thromboembolic disorder in a mammal, comprising administering Compound A to the mammal. Thromboembolic disorders include, but are not limited to, myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In another aspect are methods for treating inflammation comprising administering to the mammal at least once an effective amount of Compound A.

A further aspect provided herein are methods for the treatment of cancer comprising administering to the mammal at least once an effective amount of Compound A. The type of cancer may include, but is not limited to, pancreatic cancer, colorectal cancer, non-small cell lung cancer, and other solid or hematological tumors.

In another aspect, provided are methods for treating respiratory diseases comprising administering to the mammal at least once an effective amount of Compound A. In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, and seasonal asthma.

In another aspect, provided are methods for preventing rheumatoid arthritis and/or osteoarthritis comprising administering to the mammal at least once an effective amount of Compound A.

In another aspect, provided are methods for treating inflammatory responses of the skin comprising administering to the mammal at least once an effective amount of Compound A. Such inflammatory responses of the skin include, by way of example, dermatitis, contact dermatitis, eczema, urticaria, rosacea, and scarring. In another aspect, provided are methods for reducing psoriatic lesions in the skin, joints, or other tissues or organs, comprising administering to the mammal an effective amount of Compound A.

In any of the aforementioned aspects, provided are further embodiments in which Compound A is (a) systemically administered to the mammal; (b) administered orally to the mammal; (c) intravenously administered to the mammal; (d) administered by inhalation; (e) administered by nasal administration; (f) administered by injection to the mammal; (g) administered topically (i.e., dermal) to the mammal; (h) administered by ophthalmic administration; or (i) administered rectally to the mammal.

In any of the aforementioned aspects, provided are further embodiments comprising a single administration of Compound A, including further embodiments in which Compound A is administered (i) multiple times over the span of one day; (ii) continually; or (iii) continuously.

In any of the aforementioned aspects are further embodiments comprising multiple administrations of Compound A, including further embodiments in which (i) Compound A is administered in a single dose; (ii) the time between multiple administrations is every 6 hours; and (iii) Compound A is administered to the mammal every 8 hours. In further or alternative embodiments, the method(s) comprise a drug holiday, wherein the administration of Compound A is temporarily suspended or the dose of Compound A being administered is temporarily reduced. In certain embodiments, at the end of the drug holiday, dosing of Compound A is resumed. The length of the drug holiday can vary from 2 days to 1 year.

In some embodiments related to any of the embodiments disclosed herein (including methods, uses, formulations, combination therapy, etc.), Compound A, or a pharmaceutically acceptable salt or solvate thereof, is optically pure (i.e., greater than 99% chiral purity by HPLC). In some embodiments related to any of the embodiments disclosed herein (including methods, uses, formulations, combination therapy, etc.), Compound A, or a pharmaceutically acceptable salt or solvate thereof, is replaced with: a) Compound A, or a pharmaceutically acceptable salt or solvate thereof of lower chiral purity; b) N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide or a pharmaceutically acceptable salt or solvate thereof of any optical purity; or c) racemic N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide, or a pharmaceutically acceptable salt or solvate thereof.

In any of the embodiments disclosed herein (including methods, uses, formulations, combination therapy, etc.), amorphous Compound A is used. In any of the embodiments disclosed herein (including methods, uses, formulations, combination therapy, etc.), crystalline Compound A is used. In any of the embodiments disclosed herein (including methods, uses, formulations, combination therapy, etc.), crystalline Compound A (Form A) is used. In any of the embodiments disclosed herein (including methods, uses, formulations, combination therapy, etc.), crystalline Compound A (Form B) is used. In any of the embodiments disclosed herein (including methods, uses, formulations, combination therapy, etc.), crystalline Compound A (Form C) is used. In any of the embodiments disclosed herein (including methods, uses, formulations, combination therapy, etc.), crystalline Compound A (Form D) is used. In any of the embodiments disclosed herein (including methods, uses, formulations, combination therapy, etc.), crystalline Compound A (Form E) is used. In any of the embodiments disclosed herein (including methods, uses, formulations, combination therapy, etc.), crystalline Compound A (Form F) is used. In any of the embodiments disclosed herein (including methods, uses, formulations, combination therapy, etc.), crystalline Compound A (Form G) is used. In any of the embodiments disclosed herein (including methods, uses, formulations, combination therapy, etc.), crystalline Compound A (Form J) is used.

In any particular embodiments disclosed herein (including methods, uses, formulations, combination therapy, etc.), crystalline Compound A (Form D) is used.

In some embodiments related to any of the embodiments disclosed herein (including methods, uses, formulations, combination therapy, etc.), Compound A, or a pharmaceutically acceptable salt thereof, is replaced with an active metabolite of Compound A. In some embodiments, the active metabolite is in a crystalline form. In some embodiments, the active metabolite is in an amorphous phase. In further embodiments, the metabolite is isolated. In some embodiments related to any of the embodiments disclosed herein (including methods, uses, formulations, combination therapy, etc.), Compound A, or a pharmaceutically acceptable salt thereof, is replaced with a prodrug of Compound A, or a deuterated analog of Compound A, or a pharmaceutically acceptable salt thereof. In particular embodiments, Compound A is in a crystalline Form D.

Other objects, features, and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

INCORPORATION BY REFERENCE

All publications and patent application publications mentioned in this specification are herein incorporated by reference to the extent applicable and relevant.

BRIEF DESCRIPTION OF THE FIGURES

FIG. 1A illustrates an X-ray powder diffraction (XRPD) pattern of Form A.

FIG. 2A illustrates an X-ray powder diffraction (XRPD) pattern of Form B.

FIG. 3A illustrates an X-ray powder diffraction (XRPD) pattern of Form C.

FIG. 4A illustrates an X-ray powder diffraction (XRPD) pattern of Form D.

FIG. 5A illustrates an X-ray powder diffraction (XRPD) pattern of Form E.

FIG. 6A illustrates an X-ray powder diffraction (XRPD) pattern of Form F.

FIG. 7A illustrates an X-ray powder diffraction (XRPD) pattern of Form G.

FIG. 8A illustrates an X-ray powder diffraction (XRPD) pattern of Form J.

FIG. 9A provides Infrared (IR) spectra of free form Pattern D.

FIG. 10 illustrates a thermogravimetric analysis (TGA) thermogram of Form D.

FIG. 11 illustrates DSC thermograms of Form D.

FIG. 12 illustrates NMR spectra of Form D.

FIG. 13 illustrates an XRPD pattern of Pattern D.

FIG. 14 illustrates a TGA thermogram of Pattern D after being dried at 50° C. for 3 h (i.e., Pattern D-dry).

FIG. 15 illustrates a DSC thermogram of Pattern D after being dried at 50° C. for 3 h (i.e., Pattern D-dry).

FIG. 16 illustrates a $^1$H NMR spectrum of Pattern D after being dried at 50° C. for 3 h (i.e., Pattern D-dry).

FIG. 17 illustrates a PLM photograph of free form Pattern D after being dried at 50° C. for 3 h (i.e., Pattern D-dry).

FIG. 18 illustrates an XRPD pattern of Pattern D (i.e., Pattern D-THF-water-dry).

FIG. 19 illustrates a TGA thermogram of Pattern D (i.e., Pattern D-THF-water-dry).

FIG. 20 illustrates a DSC thermogram of Pattern D (i.e., Pattern D-TIF-water-dry).

FIG. 21 illustrates a $^1$H NMR spectrum of Pattern D (i.e., Pattern D-TIF-water-dry).

FIG. 22 illustrates an XRPD overlay of Pattern D (50 mg) after a grinding simulation experiment for 10 min.

FIG. 23 illustrates an mDSC thermogram of Pattern D (50 mg) after a grinding simulation experiment for 10 min.

FIG. 24 illustrates an XRPD overlay of Pattern D (600 mg) after a grinding simulation experiment for 10 min.

FIG. 25 illustrates an mD SC thermogram of Pattern D (600 mg) after a grinding simulation experiment for 10 min.

FIG. 26 illustrates an XRPD overlay of Pattern D (2 g) after a grinding simulation experiment for 10 min.

FIG. 27 illustrates an mDSC thermogram of Pattern D (2 g) after a grinding simulation experiment for 10 min.

FIG. 28E shows cell proliferation inhibition of newly diagnosed (A, B) and relapsed/refractory (R/R) (C, D) MM patient-derived bone marrow mononuclear cells (BMMCs) after six days of treatment with Compound A or PS-341.

FIG. 31 shows Compound A elicits >90% reduction of BCL2 transcript at twenty-four hours post-treatment in MOLM-13 AML cells.

FIG. 32C shows a dose response curve of CLL PDX samples treated with Compound A or clinical reversible menin inhibitor displaying clinical profiles of progression after prior therapy with bendamustine and exhibits high sensitivity to Compound A with >98.5% cell lethality.

FIG. 32D shows a dose response curve of CLL PDX samples treated with Compound A or clinical reversible menin inhibitor displaying clinical profiles of progression after prior therapy with ibrutinib and exhibits high sensitivity to Compound A with >98.5% cell lethality.

FIG. 32E shows a dose response curve of CLL PDX samples treated with Compound A or clinical reversible menin inhibitor displaying clinical profiles of progression after prior therapy with ibrutinib and venetoclax and exhibits high sensitivity to Compound A with >98.5% cell lethality.

DETAILED DESCRIPTION

Figure 28A:
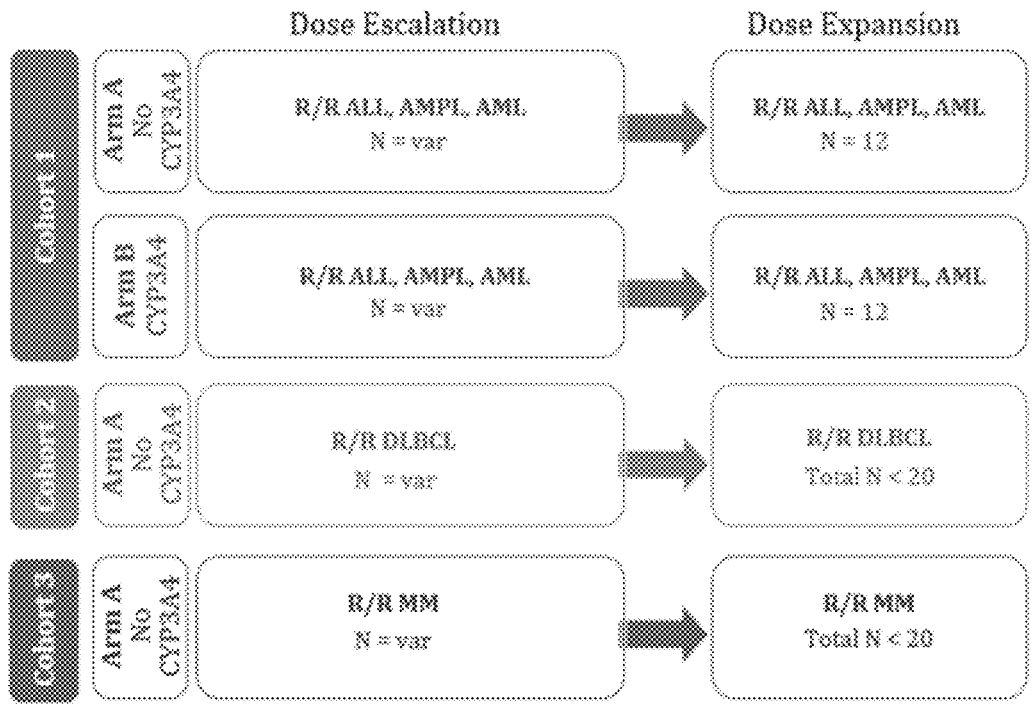
FIG. 28A shows cohorts, arms, dose escalation, and dose expansion strategy for a PhaseI clinical trial.

The diverse roles played by menin-MLL interaction in various hematopoietic cell functions suggests that small molecule inhibitors of menin-MLL interaction, such as Compound A, are useful for reducing the risk of, or treating a variety of, diseases affected by or affecting many cell types of the hematopoetic lineage including, for example, autoimmune diseases, heteroimmune conditions or diseases, inflammatory diseases, cancer (e.g., B-cell proliferative disorders), and thromboembolic disorders.

In some embodiments, Compound A can be used in the treatment of an autoimmune disease in a mammal, which includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease, Sjögren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behget's disease, chronic fatigue, dysautonomia, endometriosis, interstitial cystitis, neuromyotonia, scleroderma, and vulvodynia.

In some embodiments, Compound A can be used in the treatment of a heteroimmune disease or condition in a mammal, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, Compound A can be used in the treatment of an inflammatory disease in a mammal, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In yet other embodiments, the methods described herein can be used to treat a cancer, for example, B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In further embodiments, the methods described herein can be used to treat thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Hematological Malignancies

Disclosed herein, in certain embodiments, is a method for treating a hematological malignancy in an individual in need thereof, comprising administering to the individual an amount of Compound A.

In some embodiments, the hematological malignancy is a non-Hodgkin's lymphoma (NHL). In some embodiments, the hematological malignancy is a chronic lymphocytic leukemia (CLL), small lymphocytic lymphoma (SLL), high risk CLL, or a non-CLL/SLL lymphoma. In some embodiments, the hematological malignancy is follicular lymphoma (FL), diffuse large B-cell lymphoma (DLBCL), mantle cell lymphoma (MCL), Waldenstrom's macroglobulinemia, multiple myeloma (MM), marginal zone lymphoma, Burkitt's lymphoma, non-Burkitt high grade B cell lymphoma, or extranodal marginal zone B cell lymphoma. In some embodiments, the hematological malignancy is acute or chronic myelogenous (or myeloid) leukemia, myelodysplastic syndrome, acute lymphoblastic leukemia, or precursor B-cell acute lymphoblastic leukemia. In some embodiments, the hematological malignancy is acute myelogenous leukemia (AML). In some embodiments, the hematological malignancy is acute prolymyelocytic leukemia (AMPL). In some embodiments, the hematological malignancy is acute lymphoblastic leukemia (ALL). In some embodiments, the hematological malignancy is chronic lymphocytic leukemia (CLL). In some embodiments, the hematological malignancy is mantle cell lymphoma (MCL). In some embodiments, the hematological malignancy is diffuse large B-cell lymphoma (DLBCL). In some embodiments, the hematological malignancy is diffuse large B-cell lymphoma (DLBCL), ABC subtype. In some embodiments, the hematological malignancy is diffuse large B-cell lymphoma (DLBCL), GCB subtype. In some embodiments, the hematological malignancy is double hit lymphoma (DHL). In some embodiments, the hematological malignancy is triple hit lymphoma (THL). In some embodiments, the hematological malignancy is double/triple hit lymphoma (DHL/THL). In some embodiments, the hematological malignancy is double expresser lymphoma (DEL). In some embodiments, the hematological malignancy is Waldenstrom's macroglobulinemia (WM). In some embodiments, the hematological malignancy is multiple myeloma (MM). In some embodiments, the hematological malignancy is Burkitt's lymphoma. In some embodiments, the hematological malignancy is follicular lymphoma (FL). In some embodiments, the hematological malignancy is transformed follicular lymphoma. In some embodiments, the hematological malignancy is marginal zone lymphoma.

In some embodiments, the hematological malignancy is relapsed or refractory non-Hodgkin's lymphoma (NHL). In some embodiments, the hematological malignancy is relapsed or refractory diffuse large B-cell lymphoma (DLBCL), relapsed or refractory mantle cell lymphoma (MCL), relapsed or refractory follicular lymphoma (FL), relapsed or refractory CLL, relapsed or refractory SLL, relapsed or refractory multiple myeloma, relapsed or refractory Waldenstrom's macroglobulinemia, relapsed or refractory multiple myeloma (MM), relapsed or refractory marginal zone lymphoma, relapsed or refractory Burkitt's lymphoma, relapsed or refractory non-Burkitt high grade B cell lymphoma, relapsed or refractory extranodal marginal zone B cell lymphoma. In some embodiments, the hematological malignancy is a relapsed or refractory acute or chronic myelogenous (or myeloid) leukemia, relapsed or refractory myelodysplastic syndrome, relapsed or refractory acute lymphoblastic leukemia, or relapsed or refractory precursor B-cell acute lymphoblastic leukemia. In some embodiments, the hematological malignancy is relapsed or refractory acute myelogenous leukemia (AML). In some embodiments, the hematological malignancy is relapsed or refractory acute promyelocytic leukemia (AMPL). In some embodiments, the hematological malignancy is relapsed or refractory acute lymphoblastic leukemia (ALL). In some embodiments, the hematological malignancy is relapsed or refractory chronic lymphocytic leukemia (CLL). In some embodiments, the hematological malignancy is relapsed or refractory mantle cell lymphoma (MCL). In some embodiments, the hematological malignancy is relapsed or refractory diffuse large B-cell lymphoma (DLBCL). In some embodiments, the hematological malignancy is relapsed or refractory diffuse large B-cell lymphoma (DLBCL), ABC subtype. In some embodiments, the hematological malignancy is relapsed or refractory diffuse large B-cell lymphoma (DLBCL), GCB subtype. In some embodiments, the hematological malignancy is relapsed or refractory double hit lymphoma (DHL). In some embodiments, the hematological malignancy is relapsed or refractory triple hit lymphoma (THL). In some embodiments, the hematological malignancy is relapsed or refractory double/triple hit lymphoma (DHL/THL). In some embodiments, the hematological malignancy is relapsed or refactory double expresser lymphoma (DEL). In some embodiments, the hematological malignancy is relapsed or refractory Waldenstrom's macroglobulinemia (WM). In some embodiments, the hematological malignancy is relapsed or refractory multiple myeloma (MM). In some embodiments, the hematological malignancy is relapsed or refractory Burkitt's lymphoma. In some embodiments, the hematological malignancy is relapsed or refractory follicular lymphoma (FL).

In some embodiments, the hematological malignancy is a hematological malignancy that is classified as high-risk. In some embodiments, the hematological malignancy is high risk CLL or high-risk SLL.

B-cell lymphoproliferative disorders (BCLDs) are neoplasms of the blood and encompass, inter alia, non-Hodgkin lymphoma, multiple myeloma, and leukemia. BCLDs can originate either in the lymphatic tissues (as in the case of lymphoma) or in the bone marrow (as in the case of leukemia and myeloma), and they all are involved with the uncontrolled growth of lymphocytes or white blood cells. There are many subtypes of BCLD, for example, chronic lymphocytic leukemia (CLL) and non-Hodgkin lymphoma (NHL). The disease course and treatment of BCLD is dependent on the BCLD subtype; however, even within each subtype the clinical presentation, morphologic appearance, and response to therapy is heterogeneous.

Malignant lymphomas are neoplastic transformations of cells that reside predominantly within lymphoid tissues. Two groups of malignant lymphomas are Hodgkin's lymphoma and non-Hodgkin's lymphoma (NHL). Both types of lymphomas infiltrate reticuloendothelial tissues. However, they differ in the neoplastic cell of origin, site of disease, presence of systemic symptoms, and response to treatment (Freedman et al., "Non-Hodgkin's Lymphomas" Chapter 134, Cancer Medicine, (an approved publication of the American Cancer Society, B. C. Decker Inc., Hamilton, Ontario, 2003)).

Non-Hodgkin's Lymphomas

Disclosed herein, in certain embodiments, is a method for treating a non-Hodgkin's lymphoma in an individual in need thereof, comprising administering to the individual an amount of Compound A.

Further disclosed herein, in certain embodiments, is a method for treating relapsed or refractory non-Hodgkin's lymphoma in an individual in need thereof, comprising administering to the individual a therapeutically-effective amount of Compound A. In some embodiments, the non-Hodgkin's lymphoma is relapsed or refractory diffuse large B-cell lymphoma (DLBCL), relapsed or refractory mantle cell lymphoma, relapsed or refractory follicular lymphoma, or relapsed or refractory CLL.

Non-Hodgkin lymphomas (NHL) are a diverse group of malignancies that are predominately of B-cell origin. NHL may develop in any organs associated with lymphatic system such as the spleen, lymph nodes, or tonsils and can occur at any age. NHL is often marked by enlarged lymph nodes, fever, and weight loss. NHL is classified as either B-cell or T-cell NHL.

Lymphomas related to lymphoproliferative disorders following bone marrow or stem cell transplantation are usually B-cell NHL. In the Working Formulation classification scheme, NHL has been divided into low-, intermediate-, and high-grade categories by virtue of their natural histories (see, "The Non-Hodgkin's Lymphoma Pathologic Classification Project," Cancer 49(1982):2112-2135). The low-grade lymphomas are indolent, with a median survival of five to ten years (Horning and Rosenberg (1984) N. Engl. J. Med. 311:1471-1475). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

A non-limiting list of the B-cell NHL includes Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lymphoma, Diffuse Small Cleaved Cell, Diffuse Small Lymphocytic Lymphoma, Extranodal Marginal Zone B-cell Lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma, mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma. Additional non- Hodgkin's lymphomas are contemplated within the scope of this disclosure and should be apparent to those of ordinary skill in the art.

DLBCL

Disclosed herein, in certain embodiments, is a method for treating a DLCBL in an individual in need thereof, comprising administering to the individual an amount of Compound A. Further disclosed herein, in certain embodiments, is a method for treating relapsed or refractory DLCBL in an individual in need thereof, comprising administering to the individual a therapeutically-effective amount of Compound A.

As used herein, the term "Diffuse large B-cell lymphoma (DLBCL)" refers to a neoplasm of the germinal center B lymphocytes with a diffuse growth pattern and a high-intermediate proliferation index. DLBCLs represent approximately 30% of all lymphomas and may present with several morphological variants including the centroblastic, immunoblastic, T-cell/histiocyte rich, anaplastic and plasmoblastic subtypes. Genetic tests have shown that there are different subtypes of DLBCL. These subtypes seem to have different outlooks (i.e., prognoses) and responses to treatment. DLBCL can affect any age group but occurs mostly in older people (e.g., the average age is mid-60s).

Disclosed herein, in certain embodiments, is a method for treating diffuse large B-cell lymphoma, activated B cell-like subtype (ABC-DLBCL), in an individual in need thereof, comprising administering to the individual a covalent inhibitor of menin-MLL interaction in an amount from 300 mg/day up to, and including, 1000 mg/day. The ABC subtype of diffuse large B-cell lymphoma (ABC-DLBCL) is thought to arise from post germinal center B cells that are arrested during plasmatic differentiation. The ABC subtype of DLBCL (ABC-DLBCL) accounts for approximately 30% of total DLBCL diagnoses. It is considered the least curable of the DLBCL molecular subtypes and, as such, patients diagnosed with the ABC-DLBCL typically display significantly reduced survival rates compared with individuals with other types of DLCBL. ABC-DLBCL is most commonly associated with chromosomal translocations deregulating the germinal center master regulator BCL6 and with mutations inactivating the PRDM1 gene, which encodes a transcriptional repressor required for plasma cell differentiation.

A particularly relevant signaling pathway in the pathogenesis of ABC-DLBCL is the one mediated by the nuclear factor (NF)-κB transcription complex. The NF-κB family comprises five members (p50, p52, p65, c-rel, and RelB) that form homo- and hetero-dimers and function as transcriptional factors to mediate a variety of proliferation, apoptosis, inflammatory, and immune responses and are critical for normal B-cell development and survival. NF-κB is widely used by eukaryotic cells as a regulator of genes that control cell proliferation and cell survival. As such, many different types of human tumors have misregulated NF-κB, that is, NF-κB is constitutively active. Active NF-κB turns on the expression of genes that keep the cell proliferating and protect the cell from conditions that would otherwise cause the cell to die via apoptosis.

The dependence of ABC DLBCLs on NF-kB depends on a signaling pathway upstream of IkB kinase comprised of CARD11, BCL10, and MALT (viz., the CBM complex). Interference with the CBM pathway extinguishes NF-kB signaling in ABC DLBCL cells and induces apoptosis. The molecular basis for constitutive activity of the NF-kB pathway is a subject of current investigation, but some somatic alterations to the genome of ABC DLBCLs clearly invoke this pathway. For example, somatic mutations of the coiled-coil domain of CARD11 in DLBCL render this signaling scaffold protein able to spontaneously nucleate protein-protein interaction with MALT1 and BCL10, causing IKK activity and NF-kB activation. Constitutive activity of the B cell receptor signaling pathway has been implicated in the activation of NF-kB in ABC DLBCLs with wild type CARD11, and this is associated with mutations within the cytoplasmic tails of the B cell receptor subunits CD79A and CD79B. Oncogenic activating mutations in the signaling adapter MYD88 activate NF-kB and synergize with B cell receptor signaling in sustaining the survival of ABC DLBCL cells. In addition, inactivating mutations in a negative regulator of the NF-kB pathway, A20, occur almost exclusively in ABC DLBCL.

Indeed, genetic alterations affecting multiple components of the NF-κB signaling pathway have been recently identified in more than 50% of ABC-DLBCL patients, where these lesions promote constitutive NF-κB activation, thereby contributing to lymphoma growth. These include mutations of CARD11 (~10% of the cases), a lymphocyte-specific cytoplasmic scaffolding protein that-together with MALT1 and BCL10-forms the BCR signalosome, which relays signals from antigen receptors to the downstream mediators of NF-κB activation. An even larger fraction of cases (~30%) carry biallelic genetic lesions inactivating the negative NF-κB regulator A20. Further, high levels of expression of NF-κB target genes have been observed in ABC-DLBCL tumor samples. See, e.g., U. Klein et al., (2008), *Nature Reviews Immunology* 8:22-23; R. E. Davis et al., (2001), *Journal of Experimental Medicine* 194:1861-1874; G. Lentz et al., (2008), *Science* 319:1676-1679; M. Compagno et al., (2009), *Nature* 459:712-721; and L. Srinivasan et al., (2009), Cell 139:573-586).

DLBCL cells of the ABC subtype, such as OCI-Ly10, have chronic active BCR signaling and are very sensitive to the covalent inhibitor of menin-MLL interaction described herein. The covalent inhibitor of menin-MLL interaction described herein potently and irreversibly inhibits the growth of OCI-Ly10 ($EC_{50}$ continuous exposure=10 nM, $EC_{50}$ one hour pulse=50 nM). In addition, induction of apoptosis, as shown by caspase activation, Annexin-V flow cytometry, and increase in sub-G0 fraction is observed in OCILy10.

Follicular Lymphoma

Disclosed herein, in certain embodiments, is a method for treating a follicular lymphoma in an individual in need thereof, comprising administering to the individual an amount of Compound A. Further disclosed herein, in certain embodiments, is a method for treating relapsed or refractory follicular lymphoma in an individual in need thereof, comprising administering to the individual a therapeutically-effective amount of Compound A.

As used herein, the term "follicular lymphoma" refers to any of several types of non-Hodgkin's lymphoma in which the lymphomatous cells are clustered into nodules or follicles. The term "follicular" is used because the cells tend to grow in a circular, or nodular, pattern in lymph nodes. The average age for people with this lymphoma is about sixty.

CLL/SLL

Disclosed herein, in certain embodiments, is a method for treating a CLL or SLL in an individual in need thereof, comprising administering to the individual an amount of Compound A. Further disclosed herein, in certain embodiments, is a method for treating relapsed or refractory CLL or SLL in an individual in need thereof, comprising administering to the individual a therapeutically-effective amount of Compound A.

Chronic lymphocytic leukemia and small lymphocytic lymphoma (CLL/SLL) are commonly thought as the same disease with slightly different manifestations. Where the cancerous cells gather determines whether the disease is called CLL or SLL. When the cancer cells are primarily found in the lymph nodes, lima bean shaped structures of the lymphatic system (a system primarily of tiny vessels found in the body), the disease is called SLL. SLL accounts for about 5% to 10% of all lymphomas. When most of the cancer cells are in the bloodstream and the bone marrow, the disease is called CLL.

Both CLL and SLL are slow-growing diseases, although CLL, which is much more common, tends to grow slower. CLL and SLL are treated the same way. They are usually not considered curable with standard treatments, but depending on the stage and growth rate of the disease, most patients live longer than ten years. Occasionally over time, these slow-growing lymphomas may transform into a more aggressive type of lymphoma.

Chronic lymphoid leukemia (CLL) is the most common type of leukemia. It is estimated that 100,760 people in the United States are living with or are in remission from CLL. Most (>75%) people newly diagnosed with CLL are over the age of fifty. Currently CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of an enlarged spleen) or by radiation therapy ("de-bulking" swollen lymph nodes). Though CLL progresses slowly in most cases, CLL is considered generally incurable. Certain CLLs are classified as high-risk. As used herein, "high risk CLL" means CLL characterized by at least one of the following: 1) 17p13-; 2) 11q22-; 3) unmutated IgVH together with ZAP-70+ and/or CD38+; or 4) trisomy 12.

CLL treatment is typically administered when the patient's clinical symptoms or blood counts indicate that the disease has progressed to a point where the disease may affect the patient's quality of life.

Small lymphocytic leukemia (SLL) is very similar to CLL described above, and is also a cancer of B-cells. In SLL, the abnormal lymphocytes mainly affect the lymph nodes. However, in CLL the abnormal cells mainly affect the blood and the bone marrow. The spleen may be affected in both conditions. SLL accounts for about one in twenty-five of all cases of non-Hodgkin lymphoma. It can occur at any time from young adulthood to old age, but is rare under the age of fifty. SLL is considered an indolent lymphoma. This means that the disease progresses very slowly, and patients tend to live many years after diagnosis. However, most patients are diagnosed with advanced disease, and although SLL responds well to a variety of chemotherapy drugs, it is generally considered to be incurable. Although some cancers tend to occur more often in one gender or the other, cases and deaths due to SLL are evenly split between men and women. The average age at the time of diagnosis is sixty years.

Although SLL is indolent, SLL is persistently progressive. The usual pattern of this disease is one of high response rates to radiation therapy and/or chemotherapy, with a period of disease remission. This is followed months or years later by an inevitable relapse. Re-treatment leads to a response again, but again the disease will relapse. This means that although the short-term prognosis of SLL is quite good, over time, many patients develop fatal complications of recurrent disease. Considering the age of the individuals typically diagnosed with CLL and SLL, there is a need in the art for a simple and effective treatment of the disease with minimum side-effects that do not impede on the patient's quality of life. This disclosure fulfills this long standing need in the art.

Mantle Cell Lymphoma

Disclosed herein, in certain embodiments, is a method for treating a Mantle cell lymphoma (MCL) in an individual in need thereof, comprising administering to the individual an amount of Compound A. Further disclosed herein, in certain embodiments, is a method for treating relapsed or refractory Mantle cell lymphoma in an individual in need thereof, comprising administering to the individual a therapeutically-effective amount of Compound A.

As used herein, the term, "Mantle cell lymphoma" refers to a subtype of B-cell lymphoma, due to CD5 positive antigen-naive pregerminal center B-cell within the mantle zone that surrounds normal germinal center follicles. MCL cells generally over-express cyclin D1 due to a t(11:14) chromosomal translocation in the DNA. More specifically, the translocation is at t(11;14)(q13;q32). Only about 5% of lymphomas are of this type. The cells are small to medium in size. Men are affected most often. The average age of patients is in the early sixties. The lymphoma is usually widespread when it is diagnosed, involving lymph nodes, bone marrow, and very often the spleen. Mantle cell lymphoma is not a very fast growing lymphoma, but is difficult to treat.

Marginal Zone B-Cell Lymphoma

Disclosed herein, in certain embodiments, is a method for treating a marginal zone B-cell lymphoma in an individual in need thereof, comprising administering to the individual an amount of Compound A. Further disclosed herein, in certain embodiments, is a method for treating relapsed or refractory marginal zone B-cell lymphoma in an individual in need thereof, comprising administering to the individual a therapeutically-effective amount of Compound A.

As used herein, the term "marginal zone B-cell lymphoma" refers to a group of related B-cell neoplasms that involve the lymphoid tissues in the marginal zone, the patchy area outside the follicular mantle zone. Marginal zone lymphomas account for about 5% to 10% of lymphomas. The cells in these lymphomas look small under the microscope. There are three main types of marginal zone lymphomas including extranodal marginal zone B-cell lymphomas, nodal marginal zone B-cell lymphoma, and splenic marginal zone lymphoma.

MALT

Disclosed herein, in certain embodiments, is a method for treating a MALT in an individual in need thereof, comprising administering to the individual an amount of Compound A. Further disclosed herein, in certain embodiments, is a method for treating relapsed or refractory MALT in an individual in need thereof, comprising administering to the individual a therapeutically-effective amount of Compound A.

The term "mucosa-associated lymphoid tissue (MALT) lymphoma", as used herein, refers to extranodal manifestations of marginal-zone lymphomas. Most MALT lymphoma are a low grade, although a minority either manifest initially as intermediate-grade non-Hodgkin lymphoma (NHL) or evolve from the low-grade form. Most of the MALT lymphoma occur in the stomach, and roughly 70% of gastric MALT lymphoma are associated with *Helicobacter pylori* infection. Several cytogenetic abnormalities have been identified, the most common being trisomy 3 or t(11;18). Many of these other MALT lymphoma have also been linked to infections with bacteria or viruses. The average age of patients with MALT lymphoma is about sixty.

Nodal Marginal Zone B-Cell Lymphoma

Disclosed herein, in certain embodiments, is a method for treating a nodal marginal zone B-cell lymphoma in an individual in need thereof, comprising administering to the individual an amount of Compound A. Further disclosed herein, in certain embodiments, is a method for treating relapsed or refractory nodal marginal zone B-cell lymphoma in an individual in need thereof, comprising administering to the individual a therapeutically-effective amount of Compound A.

The term "nodal marginal zone B-cell lymphoma" refers to an indolent B-cell lymphoma that is found mostly in the lymph nodes. The disease is rare and only accounts for 1% of all Non-Hodgkin's Lymphomas (NHL). It is most commonly diagnosed in older patients, with women more susceptible than men. The disease is classified as a marginal zone lymphoma because the mutation occurs in the marginal zone of the B-cells. Due to disease confinement in the lymph nodes, this disease is also classified as nodal.

Splenic Marginal Zone B-Cell Lymphoma

Disclosed herein, in certain embodiments, is a method for treating a splenic marginal zone B-cell lymphoma in an individual in need thereof, comprising administering to the individual an amount of Compound A. Further disclosed herein, in certain embodiments, is a method for treating relapsed or refractory splenic marginal zone B-cell lymphoma in an individual in need thereof, comprising administering to the individual a therapeutically-effective amount of Compound A.

The term "splenic marginal zone B-cell lymphoma" refers to specific low-grade small B-cell lymphoma that is incorporated in the World Health Organization classification. Characteristic features are splenomegaly, moderate lymphocytosis with villous morphology, intrasinusoidal pattern of involvement of various organs, especially bone marrow, and relative indolent course. Tumor progression with increase of blastic forms and aggressive behavior are observed in a minority of patients. Molecular and cytogenetic studies have shown heterogeneous results probably because of the lack of standardized diagnostic criteria.

Burkitt Lymphoma

Disclosed herein, in certain embodiments, is a method for treating a Burkitt lymphoma in an individual in need thereof, comprising administering to the individual an amount of Compound A. Further disclosed herein, in certain embodiments, is a method for treating relapsed or refractory Burkitt lymphoma in an individual in need thereof, comprising administering to the individual a therapeutically-effective amount of Compound A.

The term "Burkitt lymphoma" refers to a type of Non-Hodgkin Lymphoma (NHL) that commonly affects children. It is a highly aggressive type of B-cell lymphoma that often starts and involves body parts other than lymph nodes. In spite of its fast-growing nature, Burkitt's lymphoma is often curable with modern intensive therapies. There are two broad types of Burkitt's lymphoma—the sporadic and the endemic varieties.

Endemic Burkitt's lymphoma. The disease involves children much more than adults, and is related to Epstein Barr Virus (EBV) infection in 95% cases. It occurs primarily near equatorial Africa, where about half of all childhood cancers are Burkitt's lymphoma. It characteristically has a high chance of involving the jawbone, a rather distinctive feature that is rare in sporadic Burkitt's. It also commonly involves the abdomen.

Sporadic Burkitt's lymphoma. The type of Burkitt's lymphoma that affects the rest of the world, including Europe and the Americas is the sporadic type. Here too, it's mainly a disease in children. The link between Epstein Barr Virus (EBV) is not as strong as with the endemic variety, though direct evidence of EBV infection is present in one out of five patients. More than the involvement of lymph nodes, it is the abdomen that is notably affected in more than 90% of the children. Bone marrow involvement is more common than in the sporadic variety.

Waldenstrom Macroglobulinemia

Disclosed herein, in certain embodiments, is a method for treating a Waldenstrom macroglobulinemia in an individual in need thereof, comprising administering to the individual an amount of Compound A. Further disclosed herein, in certain embodiments, is a method for treating relapsed or refractory Waldenstrom macroglobulinemia in an individual in need thereof, comprising administering to the individual a therapeutically-effective amount of Compound A.

The term "Waldenstrom macroglobulinemia", also known as lymphoplasmacytic lymphoma, is cancer involving a subtype of white blood cells called lymphocytes. It is characterized by an uncontrolled clonal proliferation of terminally differentiated B lymphocytes. It is also characterized by the lymphoma cells making an antibody called immunoglobulin M (IgM). The IgM antibodies circulate in the blood in large amounts, and cause the liquid part of the blood to thicken, like syrup. This can lead to decreased blood flow to many organs, which can cause problems with vision (because of poor circulation in blood vessels in the back of the eyes) and neurological problems (i.e., headache, dizziness, and confusion) caused by poor blood flow within the brain. Other symptoms can include feeling tired and weak, and a tendency to bleed easily. The underlying etiology is not fully understood but a number of risk factors have been identified, including the locus 6p21.3 on chromosome 6. There is a 2- to 3-fold risk increase of developing WM in people with a personal history of autoimmune diseases with autoantibodies and particularly elevated risks associated with hepatitis, human immunodeficiency virus, and rickettsiosis.

Multiple Myeloma

Disclosed herein, in certain embodiments, is a method for treating a myeloma in an individual in need thereof, comprising administering to the individual an amount of Compound A. Further disclosed herein, in certain embodiments, is a method for treating relapsed or refractory myeloma in an individual in need thereof, comprising administering to the individual a therapeutically-effective amount of Compound A.

Multiple myeloma, also known as MM, myeloma, plasma cell myeloma, or as Kahler's disease (i.e., after Otto Kahler) is a cancer of the white blood cells known as plasma cells. A type of B cell, plasma cells are a crucial part of the immune system responsible for the production of antibodies in humans and other vertebrates. They are produced in the bone marrow and are transported through the lymphatic system.

Leukemia

Disclosed herein, in certain embodiments, is a method for treating a leukemia in an individual in need thereof, comprising administering to the individual an amount of Compound A. Further disclosed herein, in certain embodiments, is a method for treating relapsed or refractory leukemia in an individual in need thereof, comprising administering to the individual a therapeutically-effective amount of Compound A.

Leukemia is a cancer of the blood or bone marrow characterized by an abnormal increase of blood cells, usually leukocytes (white blood cells). Leukemia is a broad term covering a spectrum of diseases. The first division is between its acute and chronic forms Acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children.

Chronic leukemia is distinguished by the excessive build up of relatively mature, but still abnormal, white blood cells. Typically taking months or years to progress, the cells are produced at a much higher rate than normal cells, resulting in many abnormal white blood cells in the blood. Chronic leukemia mostly occurs in older people, but can theoretically occur in any age group.

Additionally, the diseases are subdivided according to which kind of blood cell is affected. This split divides leukemias into lymphoblastic or lymphocytic leukemias and myeloid or myelogenous leukemias: (i) lymphoblastic or lymphocytic leukemias, the cancerous change takes place in a type of marrow cell that normally goes on to form lymphocytes, which are infection-fighting immune system cells; and (ii) myeloid or myelogenous leukemias, the cancerous change takes place in a type of marrow cell that normally goes on to form red blood cells, some other types of white cells, and platelets.

Within these main categories, there are several subcategories including, but not limited to, Acute lymphoblastic leukemia (ALL), precursor B-cell acute lymphoblastic leukemia (precursor B-ALL; also called precursor B-lymphoblastic leukemia), Acute myelogenous leukemia (AML), Chronic myelogenous leukemia (CML), and Hairy cell leukemia (HCL). Accordingly, disclosed herein, in certain embodiments, is a method for treating Acute lymphoblastic leukemia (ALL), precursor B-cell acute lymphoblastic leukemia (precursor B-ALL; also called precursor B-lymphoblastic leukemia), Acute myelogenous leukemia (AML), Chronic myelogenous leukemia (CML), or Hairy cell leukemia (HCL) in an individual in need thereof, comprising administering to the individual an amount of Compound A. In some embodiments, the leukemia is a relapsed or refractory leukemia. In some embodiments, the leukemia is a relapsed or refractory Acute lymphoblastic leukemia (ALL), relapsed or refractory precursor B-cell acute lymphoblastic leukemia (precursor B-ALL; also called precursor B-lymphoblastic leukemia), relapsed or refractory Acute myelogenous leukemia (AML), relapsed or refractory Chronic myelogenous leukemia (CML), or relapsed or refractory Hairy cell leukemia (HCL). In some embodiments, the mammal or subject has an MLL/KMT2A gene rearrangement. In some embodiments, the mammal or subject has an NPM1 mutation. In some embodiments, the mammal or subject has a TP53 mutation. In some embodiments, the mammal or subject has a NOTCH1 mutation. In some embodiments, the mammal or subject has a del(13q) karyotype. In some embodiments, the mammal or subject has a trisomy 12 karyotype.

Symptoms, diagnostic tests, and prognostic tests for each of the above-mentioned conditions are known. See, for example, *Harrison's Principles of Internal Medicine®*," 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of covalent inhibitor of menin-MLL interaction compounds, such as Compound A, for treating any of the foregoing diseases.

The therapeutic efficacy of Compound A for any one of the foregoing diseases can be optimized during a course of treatment. For example, a mammal or subject being treated can undergo a diagnostic evaluation to correlate the relief of disease symptoms or pathologies to inhibition of in vivo Menin-MLL activity achieved by administering a given dose of Compound A. Thus, the amount of the covalent inhibitor of menin-MLL interaction inhibitor compound that is administered to a mammal or subject can be increased or decreased as needed so as to maintain a level of inhibition optimal for treating the disease state in the mammal or subject.

Compound A can irreversibly inhibit menin-MLL and may be used to treat mammals suffering from menin-MLL or menin-MLL mediated conditions or diseases, including, but not limited to, cancer, autoimmune, and other inflammatory diseases. Compound A has shown efficacy in a wide variety of diseases and conditions that are described herein.

In some embodiments, Compound A is used for the manufacture of a medicament for treating any of the foregoing conditions (e.g., autoimmune diseases, inflammatory diseases, allergy disorders, B-cell proliferative disorders, or thromboembolic disorders). In some embodiments, the cancer is a B-cell proliferative disorder.

In some embodiments, the B-cell proliferative disorder is diffuse large B cell lymphoma, follicular lymphoma, chronic lymphocytic leukemia, lymphoid leukemia, ALL, soft tissue tumor, Glioblastoma, pancreatic tumor, or renal cell cancer.

In some embodiments, the cancer is cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, or bladder cancer.

In some embodiments, the cancer is bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, or cardiac tumors, craniopharyngioma, cutaneous T-cell lymphoma, extrahepatic ductal carcinoma in situ (DCIS), embryonal tumors, Ewing sarcoma, extracranial germ cell tumor, extragonadal germ cell tumor, gastrointestinal carcinoid tumor, gastrointestinal stromal tumors (GIST), germ cell tumor, gestational trophoblastic tumor, Hodgkin's lymphoma, islet cell tumors, pancreatic neuroendocrine tumors, midline tract carcinoma, and/or non-Hodgkin's lymphoma.

In some embodiments, the cancer is multiple endocrine neoplasia syndromes, multiple myeloma/plasma cell neoplasm, mycosis fungoides, myelodysplasia syndromes, myelodysplastic/myeloproliferative neoplasms, and/or multiple myeloma.

In some embodiments, the cancer is merkel cell carcinoma, malignant mesothelioma, malignant fibrous histiocytoma of bone and osteosarcoma, nasal cavity and paranasal sinus cancer, nasopharyngeal cancer, neuroblastoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, or primary central nervous system (CNS).

In some embodiments, the cancer is hairy cell leukemia, head and neck cancer, heart cancer, liver cancer, hypopharyngeal cancer, intraocular melanoma, kidney cancer, laryngeal cancer, lip and oral cavity cancer, liver cancer, lobular carcinoma in situ (LCIS), lung cancer, lymphoma, metastatic squamous neck cancer with occult primary, or mouth cancer.

In some embodiments, the cancer is multiple endocrine neoplasia syndromes, multiple myeloma/plasma cell neoplasm, mycosis fungoides, myelodysplasia syndromes, myelodysplastic/myeloproliferative neoplasms, multiple myeloma, lymphoma, prostate cancer, rectal cancer, or transitional cell cancer, In some embodiments, the cancer is retinoblastoma, rhabdomyosarcoma, salivary gland cancer, skin cancer, stomach (gastric) cancer, small cell lung cancer, small intestine cancer, soft tissue sarcoma, T-cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-induced cancer. In some embodiments, said method relates to the treatment of a non-cancerous hyperproliferative disorders such as benign hyperplasia of the skin (e.g., psoriasis), restenosis, or prostate disorders (e.g., benign prostatic hypertrophy (BPH)).

In some embodiments, the cancer is chronic lymphocytic leukemia (CLL), chronic myelogenous leukemia (CML), chronic myleoproliferative disorders, colon cancer, and/or colorectal cancer.

In some embodiments, the cancer is CNS cancer, endometrial cancer, ependymoma, esophageal cancer, esthesioneuroblastoma, eye cancer, fibrous histiocytoma of bone, gall bladder cancer, and/or gastric cancer In certain embodiments, provided herein are methods for treating the following diseases or conditions comprising administering to the mammal a compound provided herein. In some embodiments, the disease or condition is ALL (Acute Lymphoblastic Lymphoma), DLBCL (Diffuse Large B-Cell Lymphoma), FL (Follicular Lymphoma), RCC (Renal Cell Carcinoma), Childhood Medulloblastoma, Glioblastoma, Pancreatic tumor or cancer, Liver cancer (Hepatocellular Carcinoma), Prostate Cancer (Myc), Triple Negative Breast (Myc), AML (Acute Myeloid Leukemia), or MDS (Myelo Dyslplastic Syndrome). In some embodiments, the disease or condition is Early-onset Dystonia. In yet some embodiments, the disease or condition is Kabuki Syndrome.

In some embodiments, the disease or condition is p53 driven tumor.

In some embodiments, the disease or condition is a MYC driven tumor. MYC is documented to be involved broadly in many cancers, in which its expression is estimated to be elevated or deregulated in up to 70% of human cancers. High levels of MYC expression have been linked to aggressive human prostate cancer and triple negative breast cancer (Gurel et al., Mod Pathol. 2008 September; 21(9):1156-67; Palaskas et al., Cancer Res. 2011 Aug. 1; 71(15):5164-74).

Experimental models of Myc-mediated tumorigenesis suggest that established tumors are addicted to Myc and that deregulated expression of Myc result in an addiction not only to Myc but also to nutrients. These Myc-induced changes provide a unique opportunity for new therapeutic strategies. Notwithstanding the fact that normal proliferating cells (stem cell compartments and immune cells) also use MYC for renewal, many studies have focused on targeting Myc for cancer therapeutics. Strategies have emerged to inhibit MYC expression, to interrupt Myc-Max dimerization, to inhibit Myc-Max DNA binding, and to interfere with key Myc target genes (Dang et al. Cell. 2012, 149(1): 22-35).

In some embodiments, Compound A may be used to treat menin-dependent acute myeloid leukemia (AML), menin-dependent diffuse large B-cell lymphoma (DLBCL), menin-dependent Double/Triple Hit Lymphoma (DHL/THL), menin-dependent Double Expressor Lymphoma (DEL), and menin-dependent multiple myeloma (MM).

In some embodiments, Compound A may be used to treat menin-independent acute myeloid leukemia (AML), menin-independent diffuse large B-cell lymphoma (DLBCL), menin-independent Double/Triple Hit Lymphoma (DHL/THL), menin-independent Double Expressor Lymphoma (DEL), and menin-independent multiple myeloma (MM).

In some embodiments, Compound A may be used to treat menin-dependent cancer. In some embodiments, Compound A may be used to treat menin-independent cancer.

In some embodiments, Compound A may be used to treat menin-dependent hematological malignancey. In some embodiments, Compound A may be used to treat menin-independent hematological malignancey.

In some embodiments, Compound A may be used to treat hematological malignancy which involves mutation in the nucleophosmin (NMP1) gene. In some embodiments, Compound A may be used to treat hematological malignancey which does not involve mutation in the nucleophosmin (NMP1) gene.

In some embodiments, Compound A may be used to treat hematological malignancy which involves rearranged MLL. In some embodiments, Compound A may be used to treat hematological malignancy which does not rearranged MLL.

In some embodiments, Compound A may be used to treat MYC-dependent acute myeloid leukemia (AML), MYC-dependent diffuse large B-cell lymphoma (DLBCL), MYC-dependent Double/Triple Hit Lymphoma (DHL/THL), MYC-dependent Double Expressor Lymphoma (DEL), and MYC-dependent multiple myeloma (MM).

In some embodiments, Compound A may be used to treat MYC-independent acute myeloid leukemia (AML), MYC-independent diffuse large B-cell lymphoma (DLBCL), MYC-independent Double/Triple Hit Lymphoma (DHL/THL), MYC-independent Double Expressor Lymphoma (DEL), and MYC-independent multiple myeloma (MM).

In some embodiments, Compound A may be used to treat relapsed/refractory (R/R) acute leukemia (AL), DLBCL, and MM.

In some embodiments, Compound A may be used to treat cancer which involves mutation in p53 gene. In some embodiments, Compound A may be used to treat cancer which does not involve mutation in p53 gene.

In some embodiments, Compound A may be used to treat cancer which involves mutation in a RAS gene. In some embodiments, Compound A may be used to treat cancer which involves mutation in KRAS gene. In some embodiments, Compound A may be used to treat cancer which does not involve mutation in KRAS gene.

In some embodiments, Compound A may be used to treat CLL patients wherein the patients have overexpressed BCL2. In some embodiments, Compound A may be used to treat CLL patients wherein the patients do not overexpress BCL2.

In some embodiments, Compound A may be used to treat cancer which involves mutation in the ATM gene. In some embodiments, Compound A may be used to treat cancer which does not involve mutation in the ATM gene.

In some embodiments, Compound A may be used to treat cancer which involves mutation in Notch1 gene. In some embodiments, Compound A may be used to treat cancer which does not involve mutation in Notch1 gene.

In some embodiments, Compound A may be used to treat cancer which involves mutation in the TP53 gene. In some embodiments, Compound A may be used to treat cancer which does not involve mutation in the TP53 gene.

In some embodiments, Compound A may be used to treat cancer which involves mutation in the WT1 gene. In some embodiments, Compound A may be used to treat cancer which does not involve mutation in the WT1 gene.

In some embodiments, Compound A may be used to treat cancer which involves mutation in the KMT2A gene. In some embodiments, Compound A may be used to treat cancer which does not involve mutation in the KMT2A gene.

In some embodiments, Compound A may be used to treat cancer which involves mutation in the TET2 gene. In some embodiments, Compound A may be used to treat cancer which does not involve mutation in the TET2 gene.

In some embodiments, Compound A may be used to treat cancer which involves mutation in the Del(13q) gene. In some embodiments, Compound A may be used to treat cancer which does not involve mutation in the Del(13q) gene.

In some embodiments, Compound A may be used to treat cancer which involves mutation in the Trisomy 12 gene. In some embodiments, Compound A may be used to treat cancer which does not involve mutation in the Trisomy 12 gene.

Compound A, and Pharmaceutically Acceptable Salts Thereof

"Compound A" or "N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide" or any other suitable name refers to the compound with the following structure

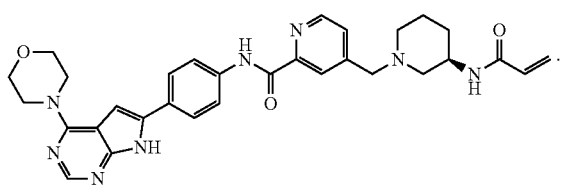

(I)

A wide variety of pharmaceutically acceptable salts are formed from Compound A and include acid addition salts formed by reacting Compound A with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc.; and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonica acid, p-toluenesulfonic acid, salicylic acid, and the like;

acid addition salts formed by reacting Compound A with an inorganic acid, which include hydrochloric acid, hydrobromic acid, sulfuric acid, nitric acid, phosphoric acid, hydroiodic acid, hydrofluoric acid, phosphorous acid, and the like.

The term "pharmaceutically acceptable salts" in reference to Compound A refers to a salt of Compound A, which does not cause significant irritation to a mammal to which it is administered and does not substantially abrogate the biological activity and properties of the neutral compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C (R3), (November 2005). Hydrates are formed when the solvent is water, or alcoholates are formed when the solvent is alcohol. In some embodiments, solvates of Compound A, or pharmaceutically acceptable salts thereof, are conveniently prepared or formed during the processes described herein. In some embodiments, solvates of Compound A are anhydrous. In some embodiments, Compound A, or pharmaceutically acceptable salts thereof, exist in unsolvated form. In some embodiments, Compound A, or pharmaceutically acceptable salts thereof, exist in unsolvated form and are anhydrous.

In yet other embodiments, Compound A, or a pharmaceutically acceptable salt thereof, is prepared in various forms, including but not limited to, amorphous phase, crystalline forms, milled forms, and nano-particulate forms. In some embodiments, Compound A, or a pharmaceutically acceptable salt thereof, is amorphous. In some embodiments, Compound A, or a pharmaceutically acceptable salt thereof, is amorphous and anhydrous. In some embodiments, Compound A, or a pharmaceutically acceptable salt thereof, is crystalline. In some embodiments, Compound A, or a pharmaceutically acceptable salt thereof, is crystalline and anhydrous.

The term "substantially free of" or "substantially in the absence of" with respect to a composition refers to a composition that includes at least 50%, 60%, 70%, 75%, 80%, 85%, or 90% by weight, in certain embodiments 95%, 98%, 99%, or 100% by weight; or in certain embodiments, 95%, 98%, 99%, or 100% of the designated enantiomer of a compound. In certain embodiments, in the methods and compounds provided herein, the compounds are substantially free of one of two enantiomers. In certain embodiments, in the methods and compounds provided herein, the compounds are substantially free from another enantiomer.

Similarly, the term "isolated" with respect to a composition refers to a composition that includes at least 50%, 60%, 70%, 75%, 85%, 90%, 95%, 98%, or 99% to 100% by weight, of the compound, the remainder comprising the other enantiomer.

As used herein, "enantiomeric excess (ee)" refers to a dimensionless mole ratio describing the purity of chiral substances that contain, for example, a single stereogenic center. For instance, an enantiomeric excess of zero would indicate a racemic (e.g., 50:50 mixture of enantiomers, or no excess of one enantiomer over the other). By way of further example, an enantiomeric excess of ninety-nine would indicate a nearly stereopure enantiomeric compound (i.e., large excess of one enantiomer over the other). The percentage enantiomeric excess, % ee=([(R)-compound]-[(S)-compound])/([(R)-compound]+[(S)-compound])×100, where the (R)-compound>(S)-compound; or % ee=([(S)-compound]-[(R)-compound])/([(S)-compound]+[(R)-compound])×100, where the (S)-compound>(R)-compound.

In some embodiments, Compound A is prepared as outlined in U.S. Pat. No. 11,084,825.

Amorphous Compound A

In some embodiments, Compound A is amorphous and anhydrous. In some embodiments, Compound A is amorphous. In some embodiments, amorphous Compound A has an X-ray Powder Diffraction (XRPD) pattern showing a lack of crystallinity.

Compound A, Form A

In some embodiments, Compound A is crystalline. In some embodiments, Compound A is crystalline Form A. Crystalline Form A of Compound A is characterized as having at least one of the following properties:
 (a) an X-ray powder diffraction (XRPD) pattern substantially the same as shown in FIG. 1A;
 (b) an X-ray powder diffraction (XRPD) pattern with characteristic peaks at 3.5±0.1° 2-Theta, 10.4±0.1° 2-Theta, 14.7±0.1° 2-Theta, 17.1±0.1° 2-Theta, 21±0.1° 2-Theta, 24.9±0.1° 2-Theta, 29.5±0.1° 2-Theta, and 34.1±0.1° 2-Theta;
 (c) an X-ray powder diffraction (XRPD) pattern with characteristic peaks at 3.5±0.1° 2-Theta, 17.1±0.1° 2-Theta, 21.0±0.1° 2-Theta, 24.9±0.1° 2-Theta, and 29.5±0.1° 2-Theta;
 (d) a DSC thermogram with an endotherm having an onset at about 234.6° C. and a peak at about 245° C.;
 or
 (e) combinations thereof.

In some embodiments, Form A of Compound A is characterized as having at least two of the properties selected from (a) to (e). In some embodiments, Form A of Compound A is characterized as having at least three of the properties selected from (a) to (e). In some embodiments, Form A of Compound A is characterized as having at least four of the properties selected from (a) to (e). In some embodiments, Form A of Compound A is characterized as having all five of the properties selected from (a) to (e).

In some embodiments, Form A has an X-ray powder diffraction (XRPD) pattern substantially the same as shown in FIG. 1A. In some embodiments, Form A has an X-ray powder diffraction (XRPD) pattern with characteristic peaks at 3.5±0.1° 2-Theta, 10.4±0.1° 2-Theta, 14.7±0.1° 2-Theta, 17.1±0.1° 2-Theta, 21.0±0.1° 2-Theta, 24.9±0.1° 2-Theta, 29.5±0.1° 2-Theta, and 30.0±0.1° 2-Theta.

In some embodiments, Form A has non-hygroscopicity. In some embodiments, Form A has hygroscopicity.

In some embodiments, Form A was obtained from ethyl acetate, isopropyl acetate, tetrahydrofuran, methyl isobutyl ketone (MIBK), methyl ethyl ketone (MEK), nitromethane, methanol, ethanol, acetonitrile, dioxane, methyl tert-butyl ether (MTBE), anisole, acetone, heptanes, a methanol:water mixture or an acetone:heptane mixture. In some embodiments, Form A was obtained from ethyl acetate, isopropyl acetate, tetrahydrofuran, methyl isobutyl ketone (MIBK), methyl ethyl ketone (MEK), nitromethane, methanol, ethanol, acetonitrile, dioxane, methyl tert-butyl ether (MTBE), anisole, acetone, heptanes, or an acetone:heptane mixture.

In some embodiments, Form A is unsolvated. In some embodiments, Form A is anhydrous. In some embodiments, Form A is solvated. In some embodiments, Form A is hydrous or is a hydrate.

Compound A, Form B

In some embodiments, Compound A is crystalline. In some embodiments, Compound A is crystalline Form B. Crystalline Form B of Compound A is characterized as having at least one of the following properties:
 (a) an X-ray powder diffraction (XRPD) pattern substantially the same as shown in FIG. 2A;
 (b) an X-ray powder diffraction (XRPD) pattern with characteristic peaks at 5.9±0.1° 2-Theta, 8.6±0.1° 2-Theta, 10.5±0.1° 2-Theta, 12.6±0.1° 2-Theta, 16.9±0.1° 2-Theta, 19±0.1° 2-Theta, 20.5±0.1° 2-Theta, and 24.6±0.1° 2-Theta;
 (c) an X-ray powder diffraction (XRPD) pattern with characteristic peaks at 8.6±0.1° 2-Theta, 10.5±0.1° 2-Theta, 12.6±0.1° 2-Theta, 16.9±0.1° 2-Theta, 19.1±0.1° 2-Theta, 20.5±0.1° 2-Theta, and 24.6±0.1° 2-Theta;
 or
 (d) combinations thereof.

In some embodiments, Form B of Compound A is characterized as having at least two of the properties selected from (a) to (d). In some embodiments, Form B of Compound A is characterized as having at least three of the properties selected from (a) to (d). In some embodiments, Form B of Compound A is characterized as having all four of the properties selected from (a) to (d).

In some embodiments, Form B has an X-ray powder diffraction (XRPD) pattern substantially the same as shown in FIG. 2A. In some embodiments, Form B has an X-ray powder diffraction (XRPD) pattern with characteristic peaks at 8.6±0.1° 2-Theta, 10.5±0.1° 2-Theta, 12.6±0.1° 2-Theta, 16.9±0.1° 2-Theta, 19.1±0.1° 2-Theta, 20.5±0.1° 2-Theta, and 24.6±0.1° 2-Theta.

In some embodiments, Form B was obtained from a mixture of methanol and water.

In some embodiments, Form B is unsolvated. In some embodiments, Form B is anhydrous. In some embodiments, Form B is solvated. In some embodiments, Form B is a hydrate.

Compound A, Form C

In some embodiments, Compound A is crystalline. In some embodiments, Compound A is crystalline Form C. Crystalline Form C of Compound A is characterized as having at least one of the following properties:
 (a) an X-ray powder diffraction (XRPD) pattern substantially the same as shown in FIG. 3A;
 (b) an X-ray powder diffraction (XRPD) pattern with characteristic peaks at 5.2±0.1° 2-Theta, 5.9±0.1° 2-Theta, 7.2±0.1° 2-Theta, 8.7±0.1° 2-Theta, 10.6±0.1° 2-Theta, 12.2±0.1° 2-Theta, 14.3±0.1° 2-Theta, 15.1±0.1° 2-Theta, 15.9±0.1° 2-Theta, 17.5±0.1° 2-Theta, 18.1±0.1° 2-Theta, and 20.1±0.1° 2-Theta;
 (c) an X-ray powder diffraction (XRPD) pattern with characteristic peaks at 5.2±0.1° 2-Theta, 5.9±0.1°

2-Theta, 8.7±0.1° 2-Theta, 12.2±0.1° 2-Theta, 14.3±0.1° 2-Theta, 15.9±0.1° 2-Theta, and 17.5±0.1° 2-Theta;
(d) a DSC thermogram with an endotherm having an onset at about 150.23° C. and a peak at about 156.86° C.;
or
(e) combinations thereof.

In some embodiments, Form C of Compound A is characterized as having at least two of the properties selected from (a) to (e). In some embodiments, Form C of Compound A is characterized as having at least three of the properties selected from (a) to (e). In some embodiments, Form C of Compound A is characterized as having at least four of the properties selected from (a) to (e). In some embodiments, Form C of Compound A is characterized as having all five of the properties selected from (a) to (e).

In some embodiments, Form C has an X-ray powder diffraction (XRPD) pattern substantially the same as shown in FIG. 3A. In some embodiments, Form C has an X-ray powder diffraction (XRPD) pattern with characteristic peaks at 5.2±0.1° 2-Theta, 5.9±0.1° 2-Theta, 7.2±0.1° 2-Theta, 8.7±0.1° 2-Theta, 10.6±0.1° 2-Theta, 12.2±0.1° 2-Theta, 14.3±0.1° 2-Theta, 15.1±0.1° 2-Theta, 15.9±0.1° 2-Theta, 17.5±0.1° 2-Theta, 18.1±0.1° 2-Theta, and 20.1±0.1° 2-Theta. In some embodiments, Form C has an X-ray powder diffraction (XRPD) pattern with characteristic peaks at 5.2±0.1° 2-Theta, 5.9±0.1° 2-Theta, 8.7±0.1° 2-Theta, 12.2±0.1° 2-Theta, 14.3±0.1° 2-Theta, 15.9±0.1° 2-Theta, and 17.5±0.1° 2-Theta.

Compound A, Form D

In some embodiments, Compound A is crystalline. In some embodiments, Compound A is crystalline Form D. Crystalline Form D of Compound A is characterized as having at least one of the following properties:
(a) an X-ray powder diffraction (XRPD) pattern substantially the same as shown in FIG. 4A;
(b) an X-ray powder diffraction (XRPD) pattern with characteristic peaks at 3.4±0.1° 2-Theta, 5.3±0.1° 2-Theta, 7±0.1° 2-Theta, 8.7±0.1° 2-Theta, 10.8±0.1° 2-Theta, 12.9±0.1° 2-Theta, 14.3±0.1° 2-Theta, 15.6±0.1° 2-Theta, 17±0.1° 2-Theta, 18.5±0.1° 2-Theta, 19.6±0.1° 2-Theta, 21.5±0.1° 2-Theta, and 24.2±0.1° 2-Theta;
(c) an X-ray powder diffraction (XRPD) pattern with characteristic peaks at 3.4±0.1° 2-Theta, 8.7±0.1° 2-Theta, 10.7±0.1° 2-Theta, 15.6±0.1° 2-Theta, 18.5±0.1° 2-Theta, 19.6±0.1° 2-Theta, and 24.2±0.1° 2-Theta;
(d) substantially the same X-ray powder diffraction (XRPD) pattern post storage in an open container at 40° C. and 75% RH for at least a week;
(e) substantially the same X-ray powder diffraction (XRPD) pattern post storage in an open container at 25° C. and 92% RH for at least a week;
(f) substantially the same X-ray powder diffraction (XRPD) pattern post storage in a closed container at 60° C. and 75% RH for at least a week;
(g) Infrared (IR) spectrum substantially similar to the one set forth in FIG. 9A;
(h) Infrared (IR) spectrum peaks (FIG. 9A) at about 3332 cm$^{-1}$ (not labeled), about 2853 cm$^{-1}$ (not labeled), about 1561 cm$^{-1}$ (not labeled), about 1523 cm$^{-1}$, about 1438 cm$^{-1}$, about 1257 cm$^{-1}$, 1112 cm$^{-1}$, and about 930 cm$^{-1}$;
(i) a thermo-gravimetric analysis (TGA) thermogram substantially similar to the one set forth in FIG. 10;
(j) a DSC thermogram substantially similar to the one set forth in FIG. 11;
(k) a DSC thermogram with an endotherm having an onset at about 260.5° C. and a peak at about 273° C. and an exotherm;
(l) $^1$H NMR (NMR) spectrum substantially similar to the one set forth in FIG. 12; (m) an observed hygroscopicity and absorption of about 2.1% water from 40% RH to 70% RH at 25° C.
(n) an observed aqueous solubility of about 0.004 mg/mL at about pH 4.5;
or
(o) combinations thereof.

In some embodiments, Form D of Compound A is characterized as having at least two of the properties selected from (a) to (n). In some embodiments, Form D of Compound A is characterized as having at least three of the properties selected from (a) to (n). In some embodiments, Form D of Compound A is characterized as having at least four of the properties selected from (a) to (n). In some embodiments, Form D of Compound A is characterized as having at least five of the properties selected from (a) to (n). In some embodiments, Form D of Compound A is characterized as having at least six of the properties selected from (a) to (n). In some embodiments, Form D of Compound A is characterized as having at least seven of the properties selected from (a) to (n). In some embodiments, Form D of Compound A is characterized as having at least eight of the properties selected from (a) to (n). In some embodiments, Form D of Compound A is characterized as having at least nine of the properties selected from (a) to (n). In some embodiments, Form D of Compound A is characterized as having at least ten of the properties selected from (a) to (n). In some embodiments, Form D of Compound A is characterized as having properties (a) to (n).

In some embodiments, Form D has an X-ray powder diffraction (XRPD) pattern substantially the same as shown in FIG. 4A. In some embodiments, Form D has an X-ray powder diffraction (XRPD) pattern with characteristic peaks at 3.4±0.1° 2-Theta, 5.3±0.1° 2-Theta, 7±0.1° 2-Theta, 8.7±0.1° 2-Theta, 10.8±0.1° 2-Theta, 12.9±0.1° 2-Theta, 14.3±0.1° 2-Theta, 15.6±0.1° 2-Theta, 17±0.1° 2-Theta, 18.5±0.1° 2-Theta, 19.6±0.1° 2-Theta, 21.5±0.1° 2-Theta, and 24.2±0.1° 2-Theta. In some embodiments, Form D has an X-ray powder diffraction (XRPD) pattern with characteristic peaks at 3.4±0.1° 2-Theta, 8.7±0.1° 2-Theta, 10.7±0.1° 2-Theta, 15.6±0.1° 2-Theta, 18.5±0.1° 2-Theta, 19.6±0.1° 2-Theta, and 24.2±0.1° 2-Theta.

In some embodiments, Form D has a thermo-gravimetric analysis (TGA) thermogram substantially similar to the one set forth in FIG. 10.

In some embodiments, Form D has a DSC thermogram substantially similar to the one set forth in FIG. 11.

In some embodiments, Form D has NMR spectra substantially similar to the one set forth in FIG. 12.

In some embodiments, Form D was obtained from methyl isobutyl ketone (MIBK). In some embodiments, Form D is solvated. In some embodiments, Form D is solvated with methyl isobutyl ketone (MIBK).

Compound A, Form E

In some embodiments, Compound A is crystalline. In some embodiments, Compound A is crystalline Form E. Crystalline Form E of Compound A is characterized as having at least one of the following properties:
(a) an X-ray powder diffraction (XRPD) pattern substantially the same as shown in FIG. 5A;

(b) an X-ray powder diffraction (XRPD) pattern with characteristic peaks at 3.4±0.1° 2-Theta, 4.7±0.1° 2-Theta, 6.3±0.1° 2-Theta, 6.9±0.1° 2-Theta, 7.1±0.1° 2-Theta, 7.6±0.1° 2-Theta, 8.6±0.1° 2-Theta, 9.3±0.1° 2-Theta, 10.8±0.1° 2-Theta, 12±0.1° 2-Theta, 12.5±0.1° 2-Theta, 13±0.1° 2-Theta, 13.8±0.1° 2-Theta, 15.7±0.1° 2-Theta, 16.2±0.1° 2-Theta, 16.7±0.1° 2-Theta, 17±0.1° 2-Theta, 17.5±0.1° 2-Theta, 18.4±0.1° 2-Theta, 18.6±0.1° 2-Theta, 19.6±0.1° 2-Theta, 20.7±0.1° 2-Theta, 21.4±0.1° 2-Theta, 22.2±0.1° 2-Theta, 23±0.1° 2-Theta, 24.2±0.1° 2-Theta, 25.3±0.1° 2-Theta, 26±0.1° 2-Theta, 28±0.1° 2-Theta, 29.2±0.1° 2-Theta, 30.5±0.1° 2-Theta, 31.6±0.1° 2-Theta, 33.6±0.1° 2-Theta, and 34.5±0.1° 2-Theta;

(c) an X-ray powder diffraction (XRPD) pattern with characteristic peaks at 4.7±0.1° 2-Theta, 7.7±0.1° 2-Theta, 10.8±0.1° 2-Theta, 13.8±0.1° 2-Theta, 17.0±0.1° 2-Theta, 18.4±0.1° 2-Theta, and 18.6±0.1° 2-Theta;

(d) a DSC thermogram with an endotherm having an onset at about 112.34° C. and a peak at about 137.26° C.;

or (e) combinations thereof.

In some embodiments, Form E of Compound A is characterized as having at least two of the properties selected from (a) to (d). In some embodiments, Form E of Compound A is characterized as having at least three of the properties selected from (a) to (d). In some embodiments, Form E of Compound A is characterized as having all four of the properties selected from (a) to (d).

In some embodiments, Form E has an X-ray powder diffraction (XRPD) pattern substantially the same as shown in FIG. 5A. In some embodiments, Form E has an X-ray powder diffraction (XRPD) pattern with characteristic peaks at 3.4±0.1° 2-Theta, 4.7±0.1° 2-Theta, 6.3±0.1° 2-Theta, 6.9±0.1° 2-Theta, 7.1±0.1° 2-Theta, 7.6±0.1° 2-Theta, 8.6±0.1° 2-Theta, 9.3±0.1° 2-Theta, 10.8±0.1° 2-Theta, 12±0.1° 2-Theta, 12.5±0.1° 2-Theta, 13±0.1° 2-Theta, 13.8±0.1° 2-Theta, 15.7±0.1° 2-Theta, 16.2±0.1° 2-Theta, 16.7±0.1° 2-Theta, 17±0.1° 2-Theta, 17.5±0.1° 2-Theta, 18.4±0.1° 2-Theta, 18.6±0.1° 2-Theta, 19.6±0.1° 2-Theta, 20.7±0.1° 2-Theta, 21.4±0.1° 2-Theta, 22.2±0.1° 2-Theta, 23±0.1° 2-Theta, 24.2±0.1° 2-Theta, 25.3±0.1° 2-Theta, 26±0.1° 2-Theta, 28±0.1° 2-Theta, 29.2±0.1° 2-Theta, 30.5±0.1° 2-Theta, 31.6±0.1° 2-Theta, 33.6±0.1° 2-Theta, and 34.5±0.1° 2-Theta. In some embodiments, Form E has an X-ray powder diffraction (XRPD) pattern with characteristic peaks at 4.7±0.1° 2-Theta, 7.7±0.1° 2-Theta, 10.8±0.1° 2-Theta, 13.8±0.1° 2-Theta, 17.0±0.1° 2-Theta, 18.4±0.1° 2-Theta, and 18.6±0.1° 2-Theta.

Compound A, Form F

In some embodiments, Compound A is crystalline. In some embodiments, Compound A is crystalline Form F. Crystalline Form F of Compound A is characterized as having at least one of the following properties:

(a) an X-ray powder diffraction (XRPD) pattern substantially the same as shown in FIG. 6A;

(b) an X-ray powder diffraction (XRPD) pattern with characteristic peaks at 4.2±0.1° 2-Theta, 6.3±0.1° 2-Theta, 8.6±0.1° 2-Theta, 8.8±0.1° 2-Theta, 12±0.1° 2-Theta, 12.2±0.1° 2-Theta, 12.5±0.1° 2-Theta, 14.4±0.1° 2-Theta, 15±0.1° 2-Theta, 16±0.1° 2-Theta, 16.8±0.1° 2-Theta, 17.2±0.1° 2-Theta, 17.5±0.1° 2-Theta, 17.8±0.1° 2-Theta, 18.8±0.1° 2-Theta, 19.2±0.1° 2-Theta, 20.1±0.1° 2-Theta, 20.5±0.1° 2-Theta, 21.7±0.1° 2-Theta, 22.1±0.1° 2-Theta, 23.4±0.1° 2-Theta, 24.2±0.1° 2-Theta, 25.3±0.1° 2-Theta, 25.5±0.1° 2-Theta, 26.3±0.1° 2-Theta, 27.1±0.1° 2-Theta, 29±0.1° 2-Theta, 30.3±0.1° 2-Theta, 31.6±0.1° 2-Theta, 33.1±0.1° 2-Theta, 34.3±0.1° 2-Theta, and 35.6±0.1° 2-Theta;

(c) an X-ray powder diffraction (XRPD) pattern with characteristic peaks at 6.3±0.1° 2-Theta, 8.6±0.1° 2-Theta, 8.8±0.1° 2-Theta, 11.9±0.1° 2-Theta, 12.2±0.1° 2-Theta, 14.4±0.1° 2-Theta, 15.0±0.1° 2-Theta, and 20.5±0.1° 2-Theta;

or (d) combinations thereof.

In some embodiments, Form F of Compound A is characterized as having at least two of the properties selected from (a) to (d). In some embodiments, Form F of Compound A is characterized as having at least three of the properties selected from (a) to (d). In some embodiments, Form F of Compound A is characterized as having all four of the properties selected from (a) to (d).

In some embodiments, Form F has an X-ray powder diffraction (XRPD) pattern substantially the same as shown in FIG. 6A. In some embodiments, Form F has an X-ray powder diffraction (XRPD) pattern with characteristic peaks at 4.2±0.1° 2-Theta, 6.3±0.1° 2-Theta, 8.6±0.1° 2-Theta, 8.8±0.1° 2-Theta, 12±0.1° 2-Theta, 12.2±0.1° 2-Theta, 12.5±0.1° 2-Theta, 14.4±0.1° 2-Theta, 15±0.1° 2-Theta, 16±0.1° 2-Theta, 16.8±0.1° 2-Theta, 17.2±0.1° 2-Theta, 17.5±0.1° 2-Theta, 17.8±0.1° 2-Theta, 18.8±0.1° 2-Theta, 19.2±0.1° 2-Theta, 20.1±0.1° 2-Theta, 20.5±0.1° 2-Theta, 21.7±0.1° 2-Theta, 22.1±0.1° 2-Theta, 23.4±0.1° 2-Theta, 24.2±0.1° 2-Theta, 25.3±0.1° 2-Theta, 25.5±0.1° 2-Theta, 26.3±0.1° 2-Theta, 27.1±0.1° 2-Theta, 29±0.1° 2-Theta, 30.3±0.1° 2-Theta, 31.6±0.1° 2-Theta, 33.1±0.1° 2-Theta, 34.3±0.1° 2-Theta, and 35.6±0.1° 2-Theta. In some embodiments, Form F has an X-ray powder diffraction (XRPD) pattern with characteristic peaks at 6.3±0.1° 2-Theta, 8.6±0.1° 2-Theta, 8.8±0.1° 2-Theta, 11.9±0.1° 2-Theta, 12.2±0.1° 2-Theta, 14.4±0.1° 2-Theta, 15.0±0.1° 2-Theta, and 20.5±0.1° 2-Theta.

Compound A, Form G

In some embodiments, Compound A is crystalline. In some embodiments, Compound A is crystalline Form G. Crystalline Form G of Compound A is characterized as having at least one of the following properties:

(a) an X-ray powder diffraction (XRPD) pattern substantially the same as shown in FIG. 7A;

(b) an X-ray powder diffraction (XRPD) pattern with characteristic peaks at 8±0.1° 2-Theta, 10.2±0.1° 2-Theta, 12.1±0.1° 2-Theta, 16.8±0.1° 2-Theta, 19.2±0.1° 2-Theta, and 24.6±0.1° 2-Theta;

(c) an X-ray powder diffraction (XRPD) pattern with characteristic peaks at 8.1±0.1° 2-Theta, 10.2±0.1° 2-Theta, 12.1±0.1° 2-Theta, 16.8±0.1° 2-Theta, 19.2±0.1° 2-Theta, and 24.6±0.1° 2-Theta;

or (d) combinations thereof.

In some embodiments, Form G of Compound A is characterized as having at least two of the properties selected from (a) to (d). In some embodiments, Form G of Compound A is characterized as having at least three of the properties selected from (a) to (d). In some embodiments, Form G of Compound A is characterized as having all four of the properties selected from (a) to (d).

In some embodiments, Form G has an X-ray powder diffraction (XRPD) pattern substantially the same as shown in FIG. 7A. In some embodiments, Form G has an X-ray powder diffraction (XRPD) pattern with characteristic peaks at 8±0.1° 2-Theta, 10.2±0.1° 2-Theta, 12.1±0.1° 2-Theta, 16.8±0.1° 2-Theta, 19.2±0.1° 2-Theta, and 24.6±0.1° 2-Theta. In some embodiments, Form G has an X-ray powder diffraction (XRPD) pattern with characteristic peaks at 8.1±0.1° 2-Theta, 10.2±0.1° 2-Theta, 12.1±0.1° 2-Theta, 16.8±0.1° 2-Theta, 19.2±0.1° 2-Theta, and 24.6±0.1° 2-Theta.

Compound A, Form J

In some embodiments, Compound A is crystalline. In some embodiments, Compound A is crystalline Form J. Crystalline Form J of Compound A is characterized as having at least one of the following properties:
  (a) an X-ray powder diffraction (XRPD) pattern substantially the same as shown in FIG. 8A;
  (b) an X-ray powder diffraction (XRPD) pattern with characteristic peaks at 3.5±0.1° 2-Theta, 4.5±0.1° 2-Theta, 6.4±0.1° 2-Theta, 8.7±0.1° 2-Theta, 10.2±0.1° 2-Theta, 11.3±0.1° 2-Theta, 11.8±0.1° 2-Theta, 13.2±0.1° 2-Theta, 13.6±0.1° 2-Theta, 14±0.1° 2-Theta, 14.6±0.1° 2-Theta, 15.4±0.1° 2-Theta, 16.1±0.1° 2-Theta, 16.6±0.1° 2-Theta, 16.9±0.1° 2-Theta, 17.2±0.1° 2-Theta, 18.3±0.1° 2-Theta, 19.1±0.1° 2-Theta, 20.5±0.1° 2-Theta, 20.8±0.1° 2-Theta, 21.6±0.1° 2-Theta, 23.5±0.1° 2-Theta, 23.8±0.1° 2-Theta, 24.6±0.1° 2-Theta, 24.9±0.1° 2-Theta, 25.2±0.1° 2-Theta, 25.8±0.1° 2-Theta, 26.2±0.1° 2-Theta, 26.7±0.1° 2-Theta, 26.8±0.1° 2-Theta, 27.4±0.1° 2-Theta, 27.7±0.1° 2-Theta, 28.7±0.1° 2-Theta, 29.3±0.1° 2-Theta, 30.1±0.1° 2-Theta, 31.2±0.1° 2-Theta, 31.8±0.1° 2-Theta, 34.1±0.1° 2-Theta, 34.9±0.1° 2-Theta, 35.6±0.1° 2-Theta, 36.4±0.1° 2-Theta, 36.7±0.1° 2-Theta, 38.5±0.1° 2-Theta, and 38.8±0.1° 2-Theta;
  (c) an X-ray powder diffraction (XRPD) pattern with characteristic peaks at 3.5±0.1° 2-Theta, 4.5±0.1° 2-Theta, 19.1±0.1° 2-Theta, 21.6±0.1° 2-Theta, 22.5±0.1° 2-Theta, and 27.4±0.1° 2-Theta;
  (d) an observed hygroscopicity and absorption of about 2.1% water from 40% RH to 70% RH at 25° C.
  or
  (e) combinations thereof.

In some embodiments, Form J of Compound A is characterized as having at least two of the properties selected from (a) to (e). In some embodiments, Form J of Compound A is characterized as having at least three of the properties selected from (a) to (e). In some embodiments, Form J of Compound A is characterized as having at least four of the properties selected from (a) to (e). In some embodiments, Form J of Compound A is characterized as having all five of the properties selected from (a) to (e).

In some embodiments, Form G has an X-ray powder diffraction (XRPD) pattern substantially the same as shown in FIG. 8A. In some embodiments, Form G has an X-ray powder diffraction (XRPD) pattern with characteristic peaks 0.5±0.1° 2-Theta, 4.5±0.1° 2-Theta, 6.4±0.1° 2-Theta, 8.7±0.1° 2-Theta, 10.2±0.1° 2-Theta, 11.3±0.1° 2-Theta, 11.8±0.1° 2-Theta, 13.2±0.1° 2-Theta, 13.6±0.1° 2-Theta, 14±0.1° 2-Theta, 14.6±0.1° 2-Theta, 15.4±0.1° 2-Theta, 16.1±0.1° 2-Theta, 16.6±0.1° 2-Theta, 16.9±0.1° 2-Theta, 17.2±0.1° 2-Theta, 18.3±0.1° 2-Theta, 19.1±0.1° 2-Theta, 20.5±0.1° 2-Theta, 20.8±0.1° 2-Theta, 21.6±0.1° 2-Theta, 23.5±0.1° 2-Theta, 23.8±0.1° 2-Theta, 24.6±0.1° 2-Theta, 24.9±0.1° 2-Theta, 25.2±0.1° 2-Theta, 25.8±0.1° 2-Theta, 26.2±0.1° 2-Theta, 26.7±0.1° 2-Theta, 26.8±0.1° 2-Theta, 27.4±0.1° 2-Theta, 27.7±0.1° 2-Theta, 28.7±0.1° 2-Theta, 29.3±0.1° 2-Theta, 30.1±0.1° 2-Theta, 31.2±0.1° 2-Theta, 31.8±0.1° 2-Theta, 34.1±0.1° 2-Theta, 34.9±0.1° 2-Theta, 35.6±0.1° 2-Theta, 36.4±0.1° 2-Theta, 36.7±0.1° 2-Theta, 38.5±0.1° 2-Theta, and 38.8±0.1° 2-Theta. In some embodiments, Form G has an X-ray powder diffraction (XRPD) pattern with characteristic peaks at 3.5±0.1° 2-Theta, 4.5±0.1° 2-Theta, 19.1±0.1° 2-Theta, 21.6±0.1° 2-Theta, 22.5±0.1° 2-Theta, and 27.4±0.1° 2-Theta.

Preparation of Crystalline Forms

In some embodiments, crystalline forms of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide are prepared as outlined in the Examples. It is noted that solvents, temperatures, and other reaction conditions presented herein may vary.

Suitable Solvents

Therapeutic agents that are administrable to mammals, such as humans, are prepared by following regulatory guidelines. Such government regulated guidelines are referred to as Good Manufacturing Practice (GMP). GMP guidelines outline acceptable contamination levels of active therapeutic agents, for example, the amount of residual solvent in the final product. Acceptable solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include benzene; carbon tetrachloride; 1,2-dichloroethane; 1,1-dichloroethene; and 1,1,1-trichloroethane.

Examples of Class 2 solvents are acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent can be a critical parameter in the synthetic process.

In some embodiments, compositions comprising Compound A comprise an organic solvent(s). In some embodiments, compositions comprising Compound A comprise a residual amount of an organic solvent(s). In some embodiments, compositions comprising Compound A comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol. In one embodiment, the Class 3 solvent is ethyl acetate. In one embodiment, the Class 3 solvent is isopropyl acetate. In one embodiment, the Class 3 solvent is tert-butylmethylether. In one embodiment, the Class 3 solvent is heptane. In one embodiment, the Class 3 solvent is isopropanol. In one embodiment, the Class 3 solvent is ethanol.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this disclosure, the use of the singular includes the plural unless specifically stated otherwise. It must be noted that, as used in the specification and the appended claims, the singular forms "a," "an" and "the" include plural referents unless the context clearly dictates otherwise. In this disclosure, the use of "or" means "and/or" unless stated otherwise. Furthermore, use of the term "including" as well as other forms, such as "include," "includes," and "included," is not limiting.

The section headings used herein are for organizational purposes only and are not to be construed as limiting the subject matter described. All documents, or portions of documents, cited in this disclosure including, but not limited to, patents, patent application publications, articles, books, manuals, and treatises are hereby expressly incorporated by reference in their entirety for any purpose.

The term "acceptable" or "pharmaceutically acceptable," with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of a compound (e.g., Compound A) dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which the compound (e.g., Compound A) is absorbed into the general circulation when the pharmaceutical composition is taken orally as compared to intravenous injection.

"Blood plasma concentration" refers to the concentration of the compound (e.g., Compound A) in the plasma component of blood within a subject. It is understood that the plasma concentration of the compound (e.g., Compound A) may vary significantly between subjects, due to variability with respect to metabolism and/or possible interactions with other therapeutic agents. In accordance with one embodiment disclosed herein, the blood plasma concentration of the compound (e.g., Compound A) may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of the compound (e.g., Compound A) may vary from subject to subject.

The terms "co-administration" or the like, as used herein, are meant to encompass administration of the selected therapeutic agents to a single subject, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic use is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound (e.g., Compound A), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agent(s) refers to the ability to increase or prolong, either in potency or duration, the effect of therapeutic agents during treatment of a disease, disorder, or condition. An "enhancing-effective amount," as used herein, refers to an amount adequate to enhance the effect of a therapeutic agent in the treatment of a disease, disorder, or condition. When used in a subject, amounts effective for this use will depend on the severity and course of the disease, disorder, or condition, previous therapy, the patient's health status and response to the drugs, and the judgment of the treating physician.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits," "inhibiting," or "inhibitor" of a menin, as used herein, refer to inhibition of menin activity, for instance menin-MLL interaction and activity.

The term "covalent inhibitor," as used herein, refers to a compound that, upon contact with a target protein (e.g., menin or menin-MLL) causes the formation of a new covalent bond with or within the protein, whereby one or more of the target protein's biological activities (e.g., phosphotransferase activity) is diminished or abolished notwithstanding the subsequent presence or absence of the covalent inhibitor. In certain embodiments, the inhibitor is irreversible.

The term "covalent menin inhibitor," as used herein, refers to an inhibitor of menin that can form a covalent bond with an amino acid residue of menin. In certain embodiments, the inhibitor is irreversible.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "prophylactically effective amount," as used herein, refers that amount of a composition applied to a patient which will relieve to some extent one or more of the symptoms of a disease, condition, or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "subject" as used herein, refers to an animal which is the object of treatment, observation, or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound. In certain embodiments, a target protein is menin.

The terms "treat," "treating," or "treatment," as used herein, include alleviating, abating, or ameliorating a disease or condition symptoms, preventing additional symptoms, ameliorating or preventing the underlying metabolic causes of symptoms, inhibiting the disease or condition, for example, arresting the development of the disease or condition, relieving the disease or condition, causing regression of the disease or condition, relieving a condition caused by the disease or condition, or stopping the symptoms of the disease or condition. The terms "treat," "treating," or "treatment," include, but are not limited to, prophylactic and/or therapeutic treatments.

As used herein, an $IC_{50}$ refers to an amount, concentration, or dosage of a particular test compound that achieves a 50% inhibition of a maximal response, such as inhibition of menin, in an assay that measures such response.

As used herein, an $EC_{50}$ refers to a dosage, concentration, or amount of a particular test compound that elicits a dose-dependent response at 50% of maximal expression of a particular response that is induced, provoked, or potentiated by the particular test compound.

Pharmaceutical Compositions/Formulations

Pharmaceutical compositions may be formulated in a conventional manner using one or more physiologically acceptable carriers including excipients and auxiliaries which facilitate processing of the active compound(s) into preparations which can be used pharmaceutically.

Proper formulation is dependent upon the route of administration chosen. Any of the well-known techniques, carriers, and excipients may be used as suitable and as understood in the art. A summary of pharmaceutical compositions, iun addition to those described herein, may be found, for example, in Remington: *The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical*

*Dosage Forms*, Marcel Decker, New York, N.Y., 1980; and *Pharmaceutical Dosage Forms and Drug Delivery* Systems, Seventh Ed. (Lippincott Williams & Wilkins 1999), each of which are incorporated herein by reference in their entirety.

A pharmaceutical composition, as used herein, refers to a mixture of a compound (e.g., Compound A) with other chemical components, such as carriers, stabilizers, diluents, dispersing agents, suspending agents, thickening agents, and/or excipients. The pharmaceutical composition facilitates administration of the compound to a subject (e.g., a mammal). In practicing the methods of treatment or use provided herein, therapeutically effective amounts of, for example, Compound A are administered in a pharmaceutical composition to a subject (e.g., a mammal) having a disease, disorder, or condition to be treated. In one embodiment the subject is a mammal. In one embodiment, the mammal is a human. A therapeutically effective amount can vary widely depending on the severity of the disease, the age and relative health of the subject, the potency of the compound used, and other factors. The compound(s) can be used singly or in combination with one or more therapeutic agents as components of mixtures.

The term "pharmaceutical combination" as used herein, means a product that results from the mixing or combining of more than one active ingredient and includes both fixed and non-fixed combinations of the active ingredients. The term "fixed combination" means that the active ingredients, for example, Compound A and a co-agent, are both administered to a subject simultaneously in the form of a single entity or dosage. The term "non-fixed combination" means that the active ingredients, for example, Compound A and a co-agent, are administered to a subject as separate entities either simultaneously, concurrently, or sequentially with no specific intervening time limits, wherein such administration provides effective levels of the two compounds in the body of the subject. The latter also applies to cocktail therapy, for example, the administration of three or more active ingredients.

In some embodiments, crystalline Compound A is incorporated into pharmaceutical compositions to provide solid oral dosage forms. In other embodiments, crystalline Compound A is used to prepare pharmaceutical compositions other than oral solid dosage forms. The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by means of conventional mixing, dissolving, granulating, dragee-making, levigating, emulsifying, encapsulating, entrapping, or compression processes.

Dosage Forms

The pharmaceutical compositions described herein can be formulated for administration to a subject (e.g., a mammal) via any conventional means including, but not limited to, oral, parenteral (e.g., intravenous, subcutaneous, or intramuscular), buccal, intranasal, rectal or transdermal administration routes. As used herein, the term "subject" is used to mean an animal, for example a mammal, including a human or non-human. The terms patient and subject may be used interchangeably.

Moreover, the pharmaceutical compositions described herein, which include Compound A can be formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

Pharmaceutical preparations for oral use can be obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, for example, tablets, effervescent tablets, and capsules, are prepared by mixing particles of Compound A with one or more pharmaceutical excipients to form a bulk blend composition. When referring to these bulk blend compositions as homogeneous, it is meant that the particles of Compound A are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, for example, one or a combination of methods: (1) dry mixing; (2) direct compression; (3) milling; (4) dry or non-aqueous granulation; (5) wet granulation; or (6) fusion. See, for example, Lachman et al., *The Theory and Practice of Industrial Pharmacy* (1986). Other methods include, for example, spray drying, pan coating, melt granulation, granulation, fluidized bed spray drying or coating (e.g., wurster coating), tangential coating, top spraying, tableting, extruding and the like.

The pharmaceutical solid dosage forms described herein can include Compound A and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combinations thereof. In still other aspects, using standard coating procedures, such as those described in Remington's Pharmaceutical Sciences, 20th Edition (2000), a film coating is provided around the formulation of Compound A. In one embodiment, some or all of the particles of the Compound A are coated. In another embodiment, some or all of the particles of Compound A are microencapsulated. In still another embodiment, the particles of Compound A are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol, and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound (e.g., Compound A) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, for example, Avicel®, Avicel® PH101, Avicel® PH102, Avicel® PH105, Elcema® P100, Emcocel®, Vivacel®, Ming Tia®, Solka-Floc®, methylcellulose, croscarmellose, or a cross-linked cellulose such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, tragacanth, sodium starch glycolate, bentonite, a natural sponge, a surfactant, a resin such as a cation-exchange resin, citrus pulp, sodium lauryl sulfate, sodium lauryl sulfate in combination starch, and the like. In some embodiments provided herein, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments provided herein, the disintegrating agent is croscarmellose sodium.

Binders impart cohesiveness to solid oral dosage form formulations. For powder filled capsule formulation, they aid in plug formation that can be filled into soft or hard shell capsules and for tablet formulation, they ensure the tablet remains intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Agoate HS-LF and HS), hydroxyethylcellulose, hydroxypropylcellulose (e.g., Klucel®), ethylcellulose (e.g., Ethocel®), microcrystalline cellulose (e.g., Avicel®), microcrystalline dextrose, amylose, magnesium aluminum silicate, polysaccharide acids, bentonites, gelatin, polyvinylpyrrolidone vinyl acetate copolymer, crospovidone, povidone, starch, pregelatinized starch, tragacanth, dextrin, a sugar such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali metal and alkaline earth metal salts, such as aluminum, calcium, magnesium, and zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like. In some embodiments provided herein, the lubricant is selected from the group consisting of stearic acid, calcium hydroxide, talc, corn starch, sodium stearyl fumarate, stearic acid, sodium stearates, magnesium stearate, zinc stearate, and waxes. In some embodiments provided herein, the lubricant is magnesium stearate.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins, and the like. In some embodiments provided herein, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments provided herein, the diluent is microcrystalline cellulose.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$; e.g., Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS, and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, for example, Pluronic® (BASF), and the like. In some embodiments provided herein, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide, and propylene oxide. In some embodiments provided herein, the surfactant is sodium lauryl sulfate.

Suitable suspending agents for use in the solid dosage forms described here include, but are not limited to, polyvinylpyrrolidone, for example, polyvinylpyrrolidone K12, polyvinylpyrrolidone K17, polyvinylpyrrolidone K25, or polyvinylpyrrolidone K30, polyethylene glycol, for example, the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxypropylmethylcellulose, polysorbate-80, hydroxyethylcellulose, sodium alginate, gums, for example, gum tragacanth and gum acacia, guar gum, xanthans including xanthan gum, sugars, cellulosics, for example, sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone, and the like.

Suitable antioxidants for use in the solid dosage forms described herein include, for example, butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of a compound (e.g., Compound A) from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound (e.g., Compound A) inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole, or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of Compound A and one or more excipients are dry blended and compressed into a mass, such as a tablet, having a hardness sufficient to provide a pharmaceutical composition that substantially disintegrates within less than about thirty minutes, less than about thirty-five minutes, less than about forty minutes, less than about forty-five minutes, less than about fifty minutes, less than about fifty-five minutes, or less than about sixty minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with the compound (e.g., Compound A) which sufficiently isolate the compound (e.g., Compound A) from other non-compatible excipients. Materials compatible with the compound (e.g., Compound A) are those that delay the release of the compounds (e.g., Compound A) in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, for example, PEG 300, PEG 400, PEG 600, PEG 800, PEG 1450, and PEG 3350, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds (e.g., Compound A) may be formulated by methods known by one of ordinary skill in the art. Such known methods include, for example, spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, for example, complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of Compound A are microencapsulated prior to being formulated into one of the above forms. In still another embodiment, some or most of the particles are coated prior to being further formulated by using standard coating procedures, such as those described in *Remington's Pharmaceutical Sciences,* 20th Edition (2000).

In other embodiments, the solid dosage formulations of Compound A are plasticized (coated) with one or more layers. Recall, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with Compound A may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with this disclosure. Effervescent salts have been used to disperse medicines in water for oral administration. Effervescent salts are granules or coarse powders containing a medicinal agent in a dry mixture, usually composed of sodium bicarbonate, citric acid, and/or tartaric acid. When salts of the compositions described herein are added to water, the acids and the base react to liberate carbon dioxide gas, thereby causing "effervescence." Examples of effervescent salts include, for example, the following ingredients sodium bicarbonate or a mixture of sodium bicarbonate and sodium carbonate, citric acid, and/or tartaric acid. Any acid-base combination that results in the liberation of carbon dioxide can be used in place of the combination of sodium bicarbonate, citric acid, and tartaric acid, as long as the ingredients were suitable for pharmaceutical use and result in a pH of about 6.0 or higher.

In some embodiments, the solid dosage forms described herein can be formulated as enteric coated delayed release oral dosage forms (i.e., as an oral dosage form of a pharmaceutical composition as described herein which utilizes an enteric coating to affect release in the small intestine of the gastrointestinal tract). The enteric coated dosage form may be a compressed, molded, or extruded tablet/mold (coated or uncoated) containing granules, powder, pellets, beads, or particles of the active ingredient and/or other composition components, which are themselves coated or uncoated. The enteric coated oral dosage form may also be a capsule (coated or uncoated) containing pellets, beads, or granules of the solid carrier or the composition, which are themselves coated or uncoated.

The term "delayed release" as used herein refers to a delivery where the release can be accomplished at some generally predictable location in the intestinal tract more distal to that which would have been accomplished if there had been no delayed release alterations. In some embodiments, the method for delay of release is a coating. Any coating should be applied to a sufficient thickness such that the entire coating does not dissolve in the gastrointestinal fluids at a pH below about five, but does dissolve at pH about five and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media at pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS, and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D, and S are insoluble in stomach and dissolve in the intestine; and Cellulose Derivatives. Examples of suitable cellulose derivatives include ethyl cellulose; and reaction mixtures of partial acetate esters of cellulose with phthalic anhydride. The performance can vary based on the degree and type of substitution. Cellulose acetate phthalate (CAP) dissolves at pH>6. Aquateric (FMC) is an aqueous based system and is a spray dried CAP pseudolatex with particles <1 m. Other components in Aquateric can include pluronics, Tweens, and acetylated monoglycerides. Other suitable cellulose derivatives include cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as HP-50, HP-55, HP-55S, and HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF) which dissolves at pH 5.5, and AS-HG (HF) which dissolves at higher pH. These polymers are offered as granules, or as fine powders for aqueous dispersions; and Poly Vinyl Acetate Phthalate (PVAP). PVAP dissolves at pH>5, and is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate, and triacetin. Conventional coating techniques such as spray or pan coating are employed to apply coatings. Coating thickness sufficient to ensure that the oral dosage form remains intact until the desired site of topical delivery in the intestinal tract is recommended.

Colorants, detackifiers, surfactants, antifoaming agents, lubricants (e.g., carnuba wax or PEG) may be added to the coatings in lieu of plasticizers to solubilize or disperse the coating material, and to improve coating performance and the coated product.

In other embodiments, the formulations described herein, which include Compound A are delivered using a pulsatile dosage form. A pulsatile dosage form is capable of providing one or more immediate release pulses at predetermined time points after a controlled lag time, or at specific sites. Many other types of controlled release systems known to those of ordinary skill in the art and are suitable for use with the formulations described herein. Examples of such delivery systems include, for example, polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, for example, Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated herein by reference.

In some embodiments, pharmaceutical formulations are provided that include particles of Compound A at least one dispersing agent or suspending agent for oral administration to a subject. The formulations may be a powder and/or granules for suspension, and upon admixture with water, a substantially uniform suspension is obtained.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Dosing and Treatment Regimens

In some embodiments, the amount of Compound A that is administered to a subject (e.g., a mammal) is from 300 mg/day up to and including 1000 mg/day. In some embodiments, the amount of Compound A that is administered to a subject (e.g., a mammal) is from 420 mg/day up to and including 840 mg/day. In some embodiments, the amount of Compound A that is administered to a subject (e.g., a mammal) is about 420 mg/day, about 560 mg/day, or about 840 mg/day. In some embodiments, the amount of Compound A that is administered to a subject (e.g., a mammal) is about 300 mg/day, about 325 mg/day, about 350 mg/day, about 375 mg/day, about 400 mg/day, about 425 mg/day, about 450 mg/day, about 475 mg/day, about 500 mg/day, about 525 mg/day, about 550 mg/day, about 560 mg/day, about 575 mg/day, about 600 mg/day, about 625 mg/day, about 650 mg/day, about 675 mg/day, about 700 mg/day, about 725 mg/day, about 750 mg/day, about 775 mg/day, about 800 mg/day, about 825 mg/day, about 840 mg/day, about 850 mg/day, about 875 mg/day, about 900 mg/day, about 925 mg/day, about 950 mg/day, about 975 mg/day, or about 1000 mg/day. In some embodiments, the amount of Compound A that is administered to a mammal is about 420 mg/day. In some embodiments, the amount of Compound A that is administered to a mammal is about 560 mg/day. In some embodiments, the $AUC_{0\text{-}24}$ of Compound A is between about 150 and about 3500 ng*h/mL. In some embodiments, the $AUC_{0\text{-}24}$ of Compound A is between about 500 and about 1100 ng*h/mL. In some embodiments, Compound A is administered orally. In some embodiments, Compound A is administered once per day, twice per day, or three times per day. In some embodiments, Compound A is administered daily. In some embodiments, Compound A is administered once daily. In some embodiments, Compound A is administered every other day. In some embodiments, the Compound A is a maintenance therapy.

In certain embodiments, the dose of Compound A is selected from 25 mg to 1000 mg. In certain embodiments, the dose of Compound A is selected from 25 mg to 750 mg. In certain embodiments, the dose of Compound A is selected from 25 mg to 650 mg. In certain embodiments, the dose of Compound A is selected from 25 mg to 500 mg. In certain embodiments, the dose of Compound A is selected from 25 mg, 50 mg, 75 mg, 100 mg, 125 mg, 150 mg, 175 mg, 200 mg, 325 mg, 500 mg, and 650 mg. In certain embodiments, the dose of Compound A is 25 mg. In certain embodiments, the dose of Compound A is 50 mg. In certain embodiments, the dose of Compound A is 75 mg. In certain embodiments, the dose of Compound A is 100 mg. In certain embodiments, the dose of Compound A is 125 mg. In certain embodiments, the dose of Compound A is 150 mg. In certain embodiments, the dose of Compound A is 175 mg. In certain embodiments, the dose of Compound A is 200 mg. In certain embodiments, the dose of Compound A is 325 mg. In certain embodiments, the dose of Compound A is 500 mg. In certain embodiments, the dose of Compound A is and 650 mg.

In certain embodiments, Compound A is administered daily. In certain embodiments, Compound A is administered twice per day. In certain embodiments, Compound A is administered three times per day. In certain embodiments, Compound A is administered four times per day. In certain embodiments, Compound A is administered daily in divided doses. In certain embodiments, Compound A is administered daily for a cycle of twenty-eight days.

Compound A can be used in the preparation of medicaments for the inhibition of menin or a homolog thereof, or for the treatment of diseases or conditions that would benefit, at least in part, from inhibition of menin or a homolog thereof, including a subject diagnosed with a hematological malignancy. In addition, a method for treating any of the diseases or conditions described herein in a subject in need of such treatment, involves administration of pharmaceutical compositions containing Compound A, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing Compound A can be administered for prophylactic, therapeutic, or maintenance treatment. In some embodiments, compositions containing Compound A are administered for therapeutic applications (e.g., administered to a subject diagnosed with a hematological malignancy). In some embodiments, compositions containing Compound A are administered for therapeutic applications (e.g., administered to a subject susceptible to or otherwise at risk of developing a hematological malignancy). In some embodiments, compositions containing Compound A are administered to a patient who is in remission as a maintenance therapy.

Amounts of Compound A will depend on the use (e.g., therapeutic, prophylactic, or maintenance). Amounts of Compound A will depend on severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial). In some embodiments, the amount of Compound A is from 10 mg/day up to and including 250 mg/day. In some embodiments, the amount of Compound A is from 25 mg/day up to and including 300 mg/day. In some embodiments, the amount of Compound A is from 25 mg/day up to and including 100 mg/day. In some embodiments, the amount of Compound A is about 25 mg/day. In some embodiments, the amount of Compound A is about 50 mg/day. In some embodiments, the amount of Compound A is about 100 mg/day. In some embodiments, the amount of Compound A is about 150 mg/day. In some embodiments, the amount of Compound A is about 200 mg/day. In some embodiments, the amount of Compound A is about 250 mg/day. In some embodiments, the amount of Compound A is from 2 mg/kg/day up to and including 13 mg/kg/day. In some embodiments, the amount of Compound A is from 2.5 mg/kg/day up to and including 8 mg/kg/day. In some embodiments, the amount of Compound A is from 2.5 mg/kg/day up to and including 6 mg/kg/day. In some embodiments, the amount of Compound A is from 2.5 mg/kg/day up to and including 4 mg/kg/day. In some embodiments, the amount of Compound A is about 2.5 mg/kg/day. In some embodiments, the amount of Compound A is about 8 mg/kg/day.

In some embodiments, pharmaceutical compositions described herein include about 25 mg of Compound A. In some embodiments, a capsule formulation is prepared that includes about 100 mg of Compound A. In some embodiments, one, two, three, four, or five of the capsule formulations are administered daily. In some embodiments, three or four of the capsules are administered daily. In some embodiments, three of the 140 mg capsules are administered once daily. In some embodiments, four of the 140 mg capsules are administered once daily. In some embodiments, the capsules are administered once daily. In other embodiments, the capsules are administered multiple times a day.

In some embodiments, Compound A is administered once per day. In some embodiments, Compound A is administered twice per day. In some embodiments, Compound A is administered three times per day. In some embodiments, Compound A is administered four times per day.

In some embodiments, Compound A is administered until disease progression, unacceptable toxicity, or based on individual choice. In some embodiments, Compound A is administered daily until disease progression, unacceptable toxicity, or based on individual choice. In some embodiments, Compound A is administered every other day until disease progression, unacceptable toxicity, or based on individual choice.

In the case wherein the patient's status does improve, upon the physician's discretion, the administration of the compound (e.g., Compound A) may be given continuously; alternatively, the dose of drug being administered may be temporarily reduced or temporarily suspended for a certain length of time (i.e., a "drug holiday"). The length of the drug holiday can vary between two days and one year, including by way of example only, two days, three days, four days, five days, six days, seven days, ten days, twelve days, fifteen days, twenty days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder, or condition is retained. Patients can, however, require intermittent treatment on a long-term basis upon any recurrence of symptoms.

The amount of a given agent that will correspond to such an amount will vary depending upon factors such as the particular compound, the severity of the disease, the identity (e.g., weight) of the subject or host in need of treatment, but can nevertheless be routinely determined in a manner known in the art according to the particular circumstances surrounding the case, including, for example, the specific agent being administered, the route of administration, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four, or more sub-doses per day.

The pharmaceutical compositions described herein may be in unit dosage forms suitable for single administration of precise dosages. In unit dosage form, the formulation is divided into unit doses containing appropriate quantities of one or more compound (e.g., Compound A). The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative. In some embodiments, each unit dosage form comprises 140 mg of Compound A. In some embodiments, an individual is administered one unit dosage form per day. In some embodiments, an individual is administered two unit dosage forms per day. In some embodiments, an individual is administered three unit dosage forms per day. In some embodiments, an individual is administered four unit dosage forms per day.

The foregoing ranges are merely suggestive, as the number of variables in regard to an individual treatment regimen is large, and considerable excursions from these recommended values are common. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is known as the therapeutic index and it can be expressed as the ratio between $LD_{50}$ and $ED_{50}$. Compounds exhibiting high therapeutic indices are recommended. The data obtained from cell culture assays and animal studies can be used in formulating a range of dosages for use in, for example, humans. The dosage of such compounds lies within a range of circulating concentrations that include the $ED_{50}$ with minimal toxicity. The dosage may vary within this range depending upon the dosage form employed and the route of administration utilized.

Combination Therapy

In certain instances, it is appropriate to administer Compound A in combination with another therapeutic agent.

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration, and times of administration can be further modified.

In various embodiments, the compounds are administered concurrently (e.g., simultaneously, essentially simultaneously, or within the same treatment protocol) or sequentially, depending upon the nature of the disease, the condition of the patient, and the actual choice of compounds used. In certain embodiments, the determination of the order of administration, and the number of repetitions of administration of each therapeutic agent during a treatment protocol, is based upon evaluation of the disease being treated and the condition of the patient.

For combination therapies described herein, dosages of the co-administered compounds vary depending on the type of co-drug employed, on the specific drug employed, on the disease or condition being treated, and so forth.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

Disclosed herein, in certain embodiments, is a method for treating a cancer in an individual in need thereof, comprising administering to the individual an amount of Compound A. In some embodiments, the method further comprises administering a second cancer treatment regimen.

In some embodiments, administering a covalent inhibitor of menin-MLL interaction before a second cancer treatment regimen reduces immune-mediated reactions to the second cancer treatment regimen. In some embodiments, administering Compound A before atumumab reduces immune-mediated reactions to atumumab.

In some embodiments, the second cancer treatment regimen comprises a chemotherapeutic agent, a steroid, an immunotherapeutic agent, a targeted therapy, or a combination thereof. In some embodiments, the second cancer treatment regimen comprises a B cell receptor pathway inhibitor. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the second cancer treatment regimen comprises an antibody, B cell receptor signaling inhibitor, a PI3K inhibitor, an IAP inhibitor, an mTOR inhibitor, a radioimmunotherapeutic, a DNA damaging agent, a proteosome inhibitor, a Cyp3A4 inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof.

In some embodiments, the second cancer treatment regimen is a BCL-2 inhibitor. In some embodiments, the second cancer treatment regimen is selected from the group consisting of oblimersen (G3139), ABT-737 (CAS Reg. No. 852808-04-9), navitoclax (ABT-263), and venetoclax (ABT-199). In some embodiments, the second cancer treatment regimen is ABT-199 (venetoclax, RG7601, GDC-0199, CAS Reg. No. 1257044-40-8, or 4-(4-((2-(4-chlorophenyl)-4,4-dimethylcyclohex-1-en-1-yl)methyl)piperazin-1-yl)-N-((3-nitro-4-((tetrahydro-2H-pyran-4-ylmethyl)amino)phenyl)sulfonyl)-2-(1H-pyrrolo(2,3-b)pyridin-5-yloxy) benzamide). In some embodiments, the second cancer treatment regimen is ABT-199 (venetoclax) and the treatment is synergistic.

In some embodiments, the second cancer treatment regimen comprises chlorambucil, ifosfamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In some embodiments, the second cancer treatment regimen comprises cyclophosphamide, hydroxydaunorubicin, vincristine, and prednisone, and optionally rituximab.

In some embodiments, the second cancer treatment regimen comprises bendamustine and rituximab.

In some embodiments, the second cancer treatment regimen comprises fludarabine, cyclophosphamide, and rituximab.

In some embodiments, the second cancer treatment regimen comprises cyclophosphamide, vincristine, and prednisone, and optionally rituximab.

In some embodiments, the second cancer treatment regimen comprises etoposide, doxorubicin, vincristine, cyclophosphamide, prednisolone, and optionally rituximab.

In some embodiments, the second cancer treatment regimen comprises dexamethasone and lenalidomide.

In some embodiments, the second cancer treatment comprises a proteasome inhibitor. In some embodiments, the second treatment comprises bortezomib. In some embodiments, the second cancer treatment comprises an epoxyketone. In some embodiments, the second cancer treatment comprises epoxomicin. In some embodiments, the second cancer treatment comprises a tetrapeptide epoxyketone. In some embodiments, the second cancer treatment comprises carfilzomib. In some embodiments, the second cancer treatment comprises disulfram, epigallocatechin-3-gallate, salinosporamide A, ONX 0912m, CEP-18770, MLN9708, or MG132.

In some embodiments, the second cancer treatment comprises a Cyp3A4 inhibitor. In some embodiments, the second cancer treatment comprises indinavir, nelfinavir, ritonavir, clarithromycin, itraconazole, ketoconazole, and/or nefazodone. In some embodiments, the second cancer treatment comprises ketoconazole.

In some embodiments, the second cancer treatment comprises a Janus Kinase (JAK) inhibitor. In some embodiments, the second treatment comprises Lestaurtinib, Tofacitinib, Ruxolitinib, CYT387, Baricitinib, or Pacritinib.

In some embodiments, the second cancer treatment comprises a histone deacetylase inhibitor (HDAC inhibitor, HDI). In some embodiments, the second cancer treatment comprises a hydroxamic acid (or hydroxamate) such as trichostatin A, vorinostat (SAHA), belinostat (PXD101), LAQ824, and panobinostat (LBH589), a cyclic tetrapeptide such as trapoxin B, a depsipeptide, a benzamide such as entinostat (MS-275), CI994, and mocetinostat (MGCD0103), phenylbutyrate, an electrophilic ketone, or an aliphatic acid compound such as valproic acid.

Additional cancer treatment regimens include Nitrogen Mustards such as bendamustine, chlorambucil, chlormethine, cyclophosphamide, ifosfamide, melphalan, prednimustine, and trofosfamide; Alkyl Sulfonates like busulfan, mannosulfan, and treosulfan; Ethylene Imines like carboquone, thiotepa, and triaziquone; Nitrosoureas like carmustine, fotemustine, lomustine, nimustine, ranimustine, semustine, and streptozocin; Epoxides such as etoglucid; Other Alkylating Agents such as dacarbazine, mitobronitol, pipobroman, and temozolomide; Folic Acid Analogues such as methotrexate, permetrexed, pralatrexate, and raltitrexed; Purine Analogs such as cladribine, clofarabine, fludarabine, mercaptopurine, nelarabine, and tioguanine; Pyrimidine Analogs such as azacitidine, capecitabine, carmofur, cytarabine, decitabine, fluorouracil, gemcitabine, and tegafur; Vinca Alkaloids such as vinblastine, vincristine, vindesine, vinflunine, and vinorelbine; Podophyllotoxin Derivatives such as etoposide and teniposide; Colchicine derivatives such as demecolcine; Taxanes such as docetaxel, paclitaxel, and paclitaxel poliglumex; Other Plant Alkaloids and Natural Products such as trabectedin; Actinomycines such as dactinomycin; Antracyclines such as aclarubicin, daunorubicin, doxorubicin, epirubicin, idarubicin, mitoxantrone, pirarubicin, valrubicin, and zorubincin; Other Cytotoxic Antibiotics such as bleomycin, ixabepilone, mitomycin, and plicamycin; Platinum Compounds such as carboplatin, cisplatin, oxaliplatin, and satraplatin; Methylhydrazines such as procarbazine; Sensitizers such as aminolevulinic acid, efaproxiral, methyl aminolevulinate, porfimer sodium, and temoporfin; Protein Kinase Inhibitors such as dasatinib, erlotinib, everolimus, gefitinib, imatinib, lapatinib, nilotinib, pazonanib, sorafenib, sunitinib, and temsirolimus; Other Antineoplastic Agents such as alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, and vorinostat; Estrogens such as diethylstilbenol, ethinylestradiol, fosfestrol, and polyestradiol phosphate; Progestogens such as gestonorone, medroxyprogesterone, and megestrol; Gonadotropin Releasing Hormone Analogs such as buserelin, goserelin, leuprorelin, and triptorelin; Anti-Estrogens such as fulvestrant, tamoxifen, and toremifene; Anti-Androgens such as bicalutamide, flutamide, and nilutamide; Enzyme Inhibitors such as aminoglutethimide, anastrozole, exemestane, formestane, letrozole, and vorozole; Other Hormone Antagonists such as abarelix and degarelix; Immunostimulants such as histamine dihydrochloride, mifamurtide, pidotimod, plerixafor, roquinimex, and thymopentin; Immunosuppressants such as everolimus, gusperimus, leflunomide, mycophenolic acid, and sirolimus; Calcineurin Inhibitors such as ciclosporin and tacrolimus; Other Immunosuppressants such as azathioprine, lenalidomide, methotrexate, and thalidomide; and Radiopharmaceuticals such as iobenguane.

Additional cancer treatment regimens include interferons, interleukins, Tumor Necrosis Factors, Growth Factors, or the like.

Additional cancer treatment regimens include Immunostimulants such as ancestim, filgrastim, lenograstim, molgramostim, pegfilgrastim, and sargramostim; Interferons such as interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, and peginterferon alfa-2b; Interleukins such as aldesleukin and oprelvekin; Other Immunostimulants such as BCG vaccine, glatiramer acetate, histamine dihydrochloride, immunocyanin, lentinan, melanoma vaccine, mifamurtide, pegademase, pidotimod, plerixafor, poly I.C, poly ICLC, roquinimex, tasonermin, and thymopentin; Immunosuppressants such as abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, and sirolimus; TNF alpha Inhibitors such as adalimumab, afelimomab, certolizumab pegol, etanercept, golimumab, and infliximab; Interleukin Inhibitors such as anakinra, basiliximab, canakinumab, daclizumab, mepolizumab, rilonacept, tocilizumab, and ustekinumab; Calcineurin Inhibitors such as ciclosporin and tacrolimus; Other Immunosuppressants such as azathioprine, lenalidomide, methotrexate, and thalidomide.

Additional cancer treatment regimens include Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

Additional cancer treatment regimens include Monoclonal Antibodies such as alemtuzumab, bevacizumab, catumaxomab, cetuximab, edrecolomab, gemtuzumab, ofatumumab, panitumumab, rituximab, and trastuzumab; Immunosuppressants such as eculizumab, efalizumab, muromab-CD3, and natalizumab; TNF alpha Inhibitors such as adalimumab, afelimomab, certolizumab pegol, golimumab, and infliximab; Interleukin Inhibitors such as basiliximab, canakinumab, daclizumab, mepolizumab, tocilizumab, and ustekinumab; Radiopharmaceuticals such as ibritumomab tiuxetan, and tositumomab; Others Monoclonal Antibodies such as abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, and zalutumumab.

Additional cancer treatment regimens include agents that affect the tumor micro-enviroment such as cellular signaling network (e.g. phosphatidylinositol 3-kinase (PI3K) signaling pathway, signaling from the B-cell receptor and the IgE receptor). In some embodiments, the second agent is a PI3K signaling inhibitor or a syc kinase inhibitor. In one embodiment, the syk inhibitor is R788. In another embodiment, the second agent is a PKCγ inhibitor such as enzastaurin.

Examples of agents that affect the tumor micro-environment include PI3K signaling inhibitor, syc kinase inhibitor, Protein Kinase Inhibitors such as dasatinib, erlotinib, everolimus, gefitinib, imatinib, lapatinib, nilotinib, pazonanib, sorafenib, sunitinib, and temsirolimus; Other Angiogenesis Inhibitors such as GT-111, JI-101, and R1530; Other Kinase Inhibitors such as AC220, AC480, ACE-041, AMG 900, AP24534, Arry-614, AT7519, AT9283, AV-951, axitinib, AZD1152, AZD7762, AZD8055, AZD8931, bafetinib, BAY 73-4506, BGJ398, BGT226, BI 811283, B16727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMID 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, RO5185426, SAR103168, SCH 727965, SGI-1176, SGX523, SNS-314, TAK-593, TAK-901, TKI258, TLN-232, TTP607, XL147, XL228, XL281RO5126766, XL418, and XL765.

Further examples of anti-cancer agents for use in combination with a covalent inhibitor of menin-MLL interaction compound (e.g., Compound A) include inhibitors of mitogen-activated protein kinase signaling, for example, U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a covalent inhibitor of menin-HLL interaction compound (e.g., Compound A) include Adriamycin, Dactinomycin, Bleomycin, Vinblastine, Cisplatin, and acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer agents that can be employed in combination with a covalent inhibitor of menin-HLL interaction compound (e.g., Compound A) include 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorambucil; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogues; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin such as growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogues; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistant gene inhibitors; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidants; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulators; protein kinase C inhibitors; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugates; raf antagonists; raltitrexed; ramosetron; ras farnesyl protein transferase inhibitors; ras inhibitors; ras-GAP inhibitors; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding proteins; sizofiran; sobuzoxane; sodium borocaptate; sodium phenylacetate; solverol; somatomedin binding proteins; sonermin; sparfosic acid; spicamycin D; spiromustine; splenopentin; spongistatin 1; squalamine; stem cell inhibitors; stem-cell division inhibitors; stipiamide; stromelysin inhibitors; sulfinosine; superactive vasoactive intestinal peptide antagonists; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetics; thymalfasin; thymopoietin receptor agonists; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a covalent inhibitor of menin-HLL interaction compound (e.g., Compound A) include alkylating agents, antimetabolites, natural products, or hormones, for example, nitrogen mustards (e.g., mechloroethamine, cyclophosphamide, and chlorambucil, etc.), alkyl sulfonates (e.g., busulfan), nitrosoureas (e.g., carmustine, and lomusitne, etc.), or triazenes (e.g., decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, and pentostatin).

Examples of alkylating agents that can be employed in combination a covalent inhibitor of menin-MLL interaction compound (e.g., Compound A) include, but are not limited to, nitrogen mustards (e.g., mechloroethamine, cyclophosphamide, chlorambucil, and meiphalan, etc.), ethylenimine and methylmelamines (e.g., hexamethlymelamine, and thiotepa), alkyl sulfonates (e.g., busulfan), nitrosoureas (e.g., carmustine, lomusitne, semustine, and streptozocin, etc.), or triazenes (e.g., decarbazine, etc.). Examples of antimetabolites include, but are not limited to folic acid analog (e.g., methotrexate), or pyrimidine analogs (e.g., fluorouracil, floxouridine, and Cytarabine), and purine analogs (e.g., mercaptopurine, thioguanine, and pentostatin).

Examples of anti-cancer agents which act by arresting cells in the G2-M phases due to stabilized microtubules and which can be used in combination with a covalent inhibitor of menin-MLL interaction compound (e.g., Compound A) include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCI), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-4AABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

In certain embodiments, where the individual is suffering from or at risk of suffering from an autoimmune disease, an inflammatory disease, or an allergy disease, Compound A can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Kits or Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include those described in, for example, U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment.

In some embodiments, the compounds or compositions described herein, are presented in a package or dispenser device which may contain one or more unit dosage forms containing the active ingredient. The compound or composition described herein is packaged alone, or packaged with another compound or another ingredient or additive. In some embodiments, the package contains one or more containers filled with one or more of the ingredients of the pharmaceutical compositions described herein. In some embodiments, the package comprises metal or plastic foil, such as a blister pack. In some embodiments, the package or dispenser device is accompanied by instructions for administration, such as instructions for administering the compounds or compositions for treating a neoplastic disease. In some embodiments, the package or dispenser is accompanied with a notice associated with the container in a form prescribed by a governmental agency regulating the manufacture, use, or sale of pharmaceuticals, which notice is reflective of approval by the agency in the form of the drug for human or veterinary administration. In some embodiments, such notice, for example, is the labeling approved by the U.S. Food and Drug Administration for prescription drugs, or the approved product insert. In some embodiments, compositions include a compound described herein (e.g., Compound A) formulated in a compatible pharmaceutical carrier and are prepared, placed in an appropriate container, and labeled for treatment of an indicated condition.

For example, the container(s) include Compound A, optionally in a composition or in combination with another agent as described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers, or other characters forming the label are attached, molded, or etched into the container itself; a label is associated with a container when it is present within a receptacle or carrier that also holds the container, for example, as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein (e.g., Compound A). The pack, for example, contains metal or plastic foil, such as a blister pack. In one embodiment, the pack or dispenser device is accompanied by instructions for administration. In one embodiment, the pack or dispenser is also accompanied with a notice associated with the container in a form prescribed by a governmental agency regulating the manufacture, use, or sale of pharmaceuticals, which notice is reflective of approval by the agency in the form of the drug for human or veterinary administration. Such notice, for example, is the labeling approved by the U.S. Food and Drug Administration for prescription drugs, or the approved product insert. In one embodiment, compositions containing a compound provided herein (e.g., Compound A) formulated in a compatible pharmaceutical carrier are also prepared, placed in an appropriate container, and labeled for treatment of an indicated condition.

In another aspect, described herein is an deuterium analog of Compound A as a covalent inhibitor of menin-MLL interaction [N-[4-[4-(4-morpholinyl)-7H-pyrrolo[2,3-d]pyrimidin-6-yl]phenyl]-4-[[3-[(1-oxo-2-propen-1-yl)amino]-1-piperidinyl]methyl]-2-pyridinecarboxamide, deuterium analog], including stereoisomers, pharmaceutically acceptable solvates (including hydrates), polymorphs, and amorphous phases, and methods of uses thereof. In certain embodiments, only one hydrogen is replaced with deuterium. In certain embodiments, one or more hydrogens are replaced with deuterium.

In certain embodiments, the deuterium analog of Compound A is:

(I)

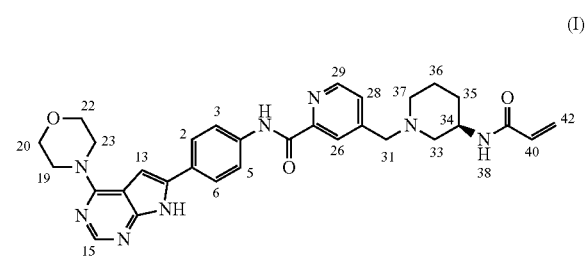 [SMILES: C=CC(=O)N[C@@H]1CCCN(Cc2ccnc(C(=O)Nc3ccc(-c4cc5c(N6CCOCC6)ncnc5[nH]4)cc3)c2)C1]

wherein deuterium is attached to any one or more positions selected from 2, 3, 5, 6, 13, 15, 19, 20, 22, 23, 26, 28, 29, 31, 33-37, 40, and 42 as shown above.

In certain embodiments, deuterium is attached to any one or more positions selected from 2, 3, 5, and 6 as shown above. In certain embodiments, deuterium is attached to any one or more positions selected from 13 and 15 as shown above. In certain embodiments, deuterium is attached to any one or more positions selected from 19, 20, 22, and 23 as shown above. In certain embodiments, deuterium is attached to any one or more positions selected from 26, 28, and 29 as shown above. In certain embodiments, deuterium is attached to position 31 as shown above. In certain embodiments, deuterium is attached to any one or more positions selected from 33-36 as shown above. In certain embodiments, deuterium is attached to any one or more positions selected from 40-42 as shown above.

In certain embodiments, the deuterium analog of Compound A is:

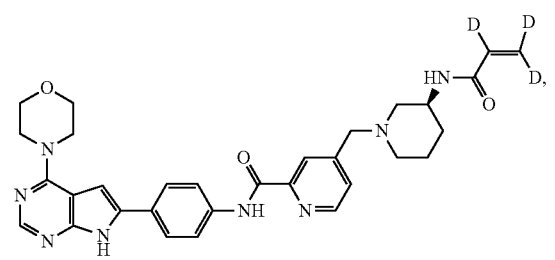

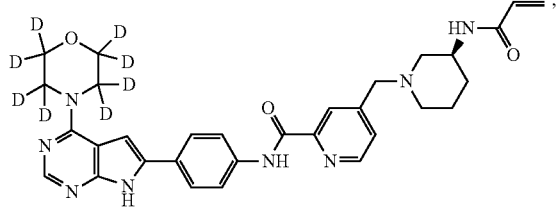

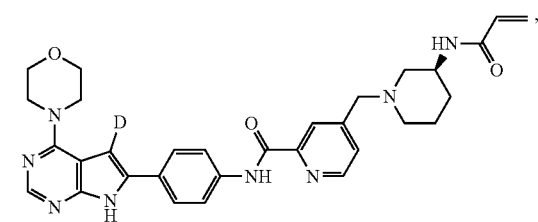

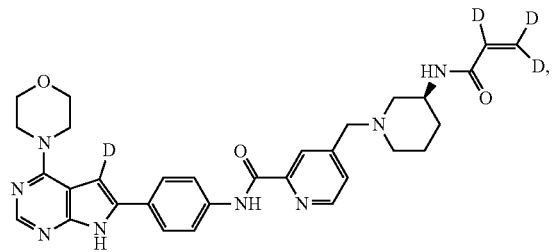

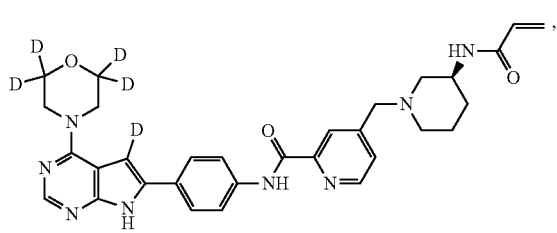

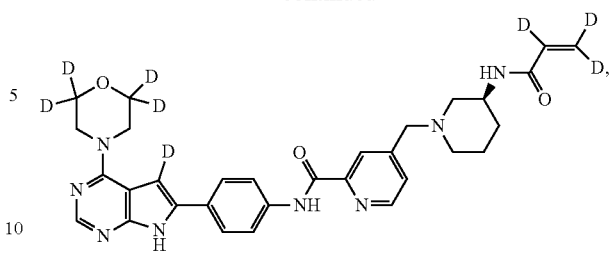

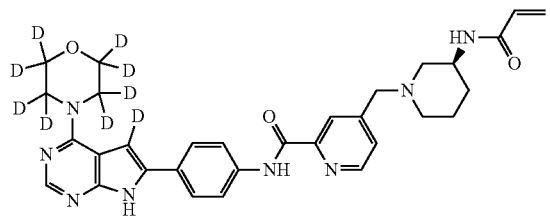

or

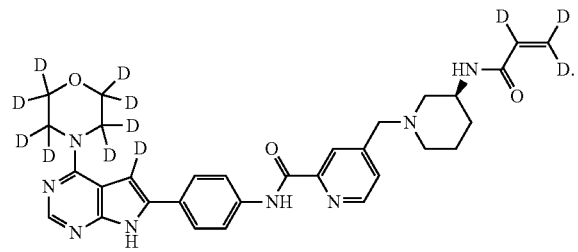

In certain embodiments, one or more hydrogens of the central pyridine ring is replaced with deuterium.

In another aspect, described herein is a covalent inhibitor of menin-MLL interaction, Compound P, including stereoisomers, pharmaceutically acceptable solvates (including hydrates), polymorphs, and amorphous phases, and methods of uses thereof. In certain embodiments, only one hydrogen of Compound P is replaced with deuterium.

Compound P

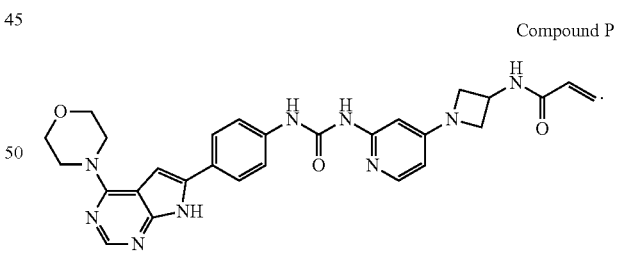

In another aspect, described herein is a deuterium analog of Compound P as a covalent inhibitor of menin-MLL interaction, including stereoisomers, pharmaceutically acceptable solvates (including hydrates), polymorphs, and amorphous phases, and methods of uses thereof. In certain embodiments, only one hydrogen of Compound P is replaced with deuterium. In certain embodiments, one or more hydrogens of Compound P are replaced with deuterium.

In certain embodiments, the deuterium analog of Compound P is:

Compound P

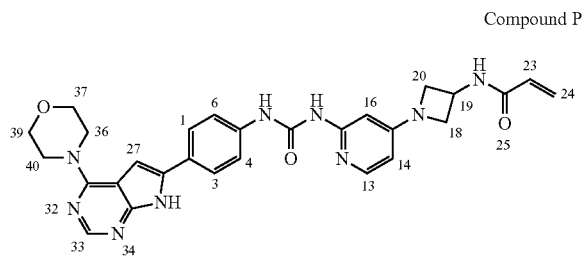 [SMILES: C=CC(=O)NC1CN(c2ccnc(NC(=O)Nc3ccc(-c4cc5c(N6CCOCC6)ncnc5[nH]4)cc3)c2)C1]

wherein deuterium is attached to any one or more positions selected from 1, 3, 4, 6, 13, 14, 16, 18-20, 23, 24, 27, 33, 36, 37, 39, and 40 as shown above.

In certain embodiments, deuterium is attached to any one or more positions selected from 1, 3, 4, and 6 as shown above.

In certain embodiments, deuterium is attached to any one or more positions selected from 13, 14, and 16 as shown above.

In certain embodiments, deuterium is attached to any one or more positions selected from 18-20 as shown above.

In certain embodiments, deuterium is attached to any one or more positions selected from 23, and 24 as shown above.

In certain embodiments, deuterium is attached to position 27 as shown above.

In certain embodiments, deuterium is attached to any one or more positions selected from 33 as shown above.

In certain embodiments, deuterium is attached to any one or more positions selected from 36, 37, 39, and 40 as shown above.

In certain embodiments, the deuterium analog of Compound P is:

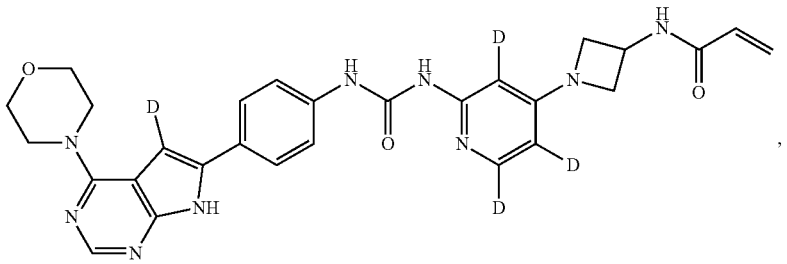

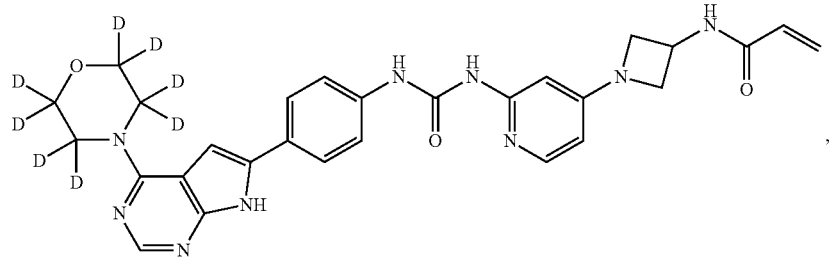

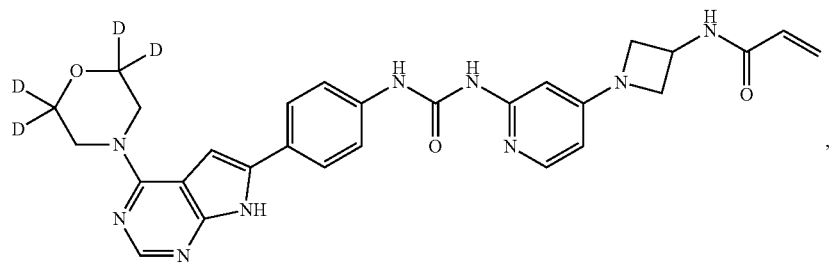

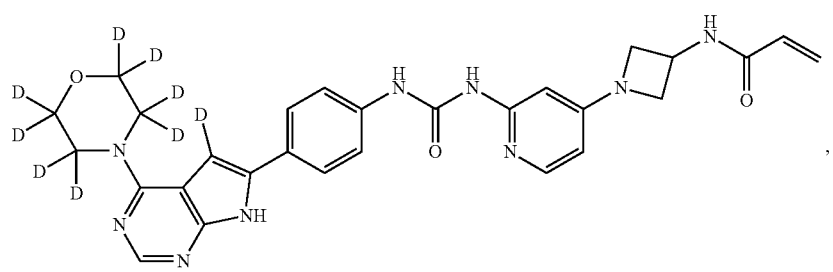

-continued
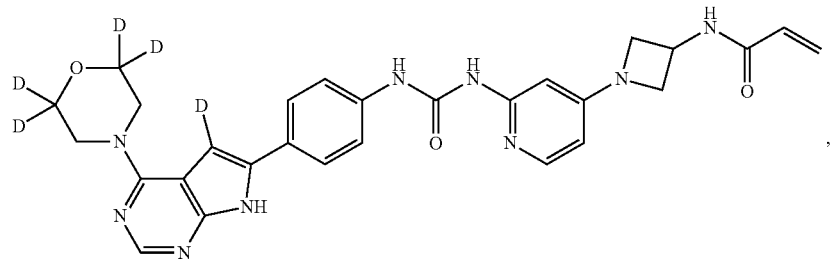
,
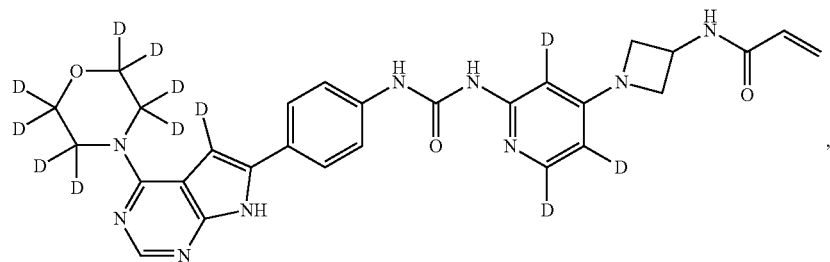
,
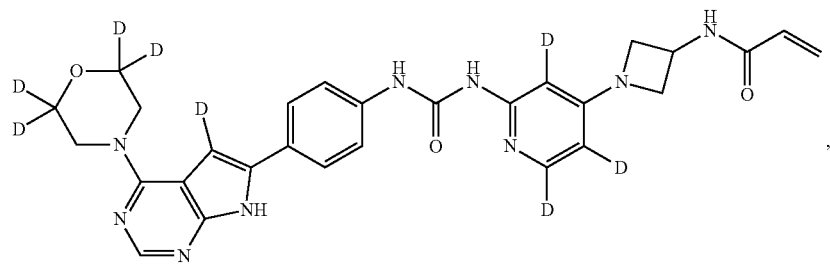
,
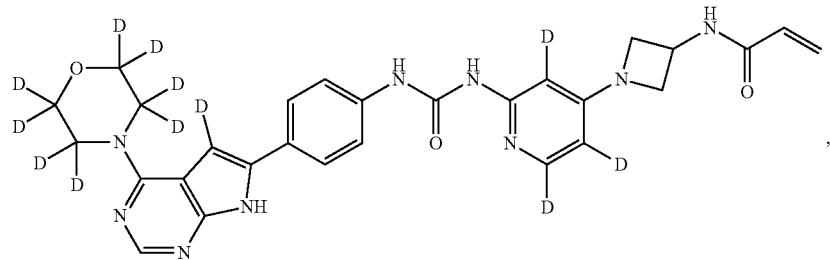
,
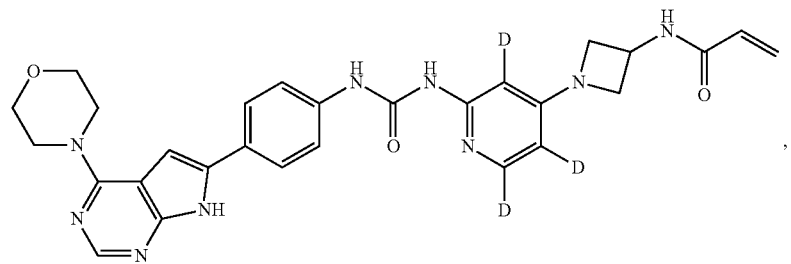
,
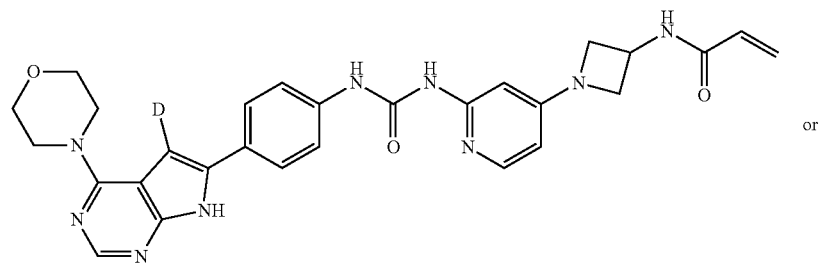
or -continued

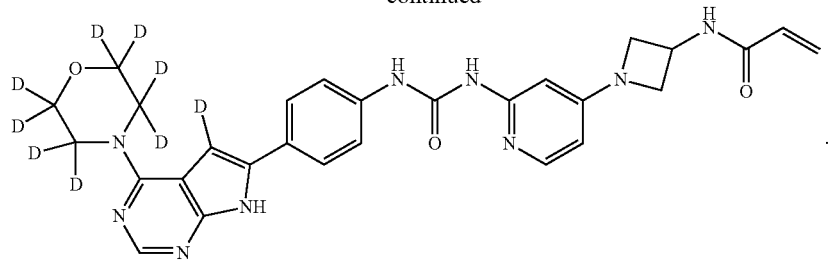

EXAMPLES

The following ingredients, formulations, processes, and procedures for making compounds and practicing the methods disclosed herein correspond to the compounds and methods described above.

Preparation of Compound A

Compound A was prepared according to the method described in U.S. Pat. No. 11,084,825 (incorporated by reference in its entirety).

Alternately, Compound A can be prepared following the synthetic scheme depicted below:

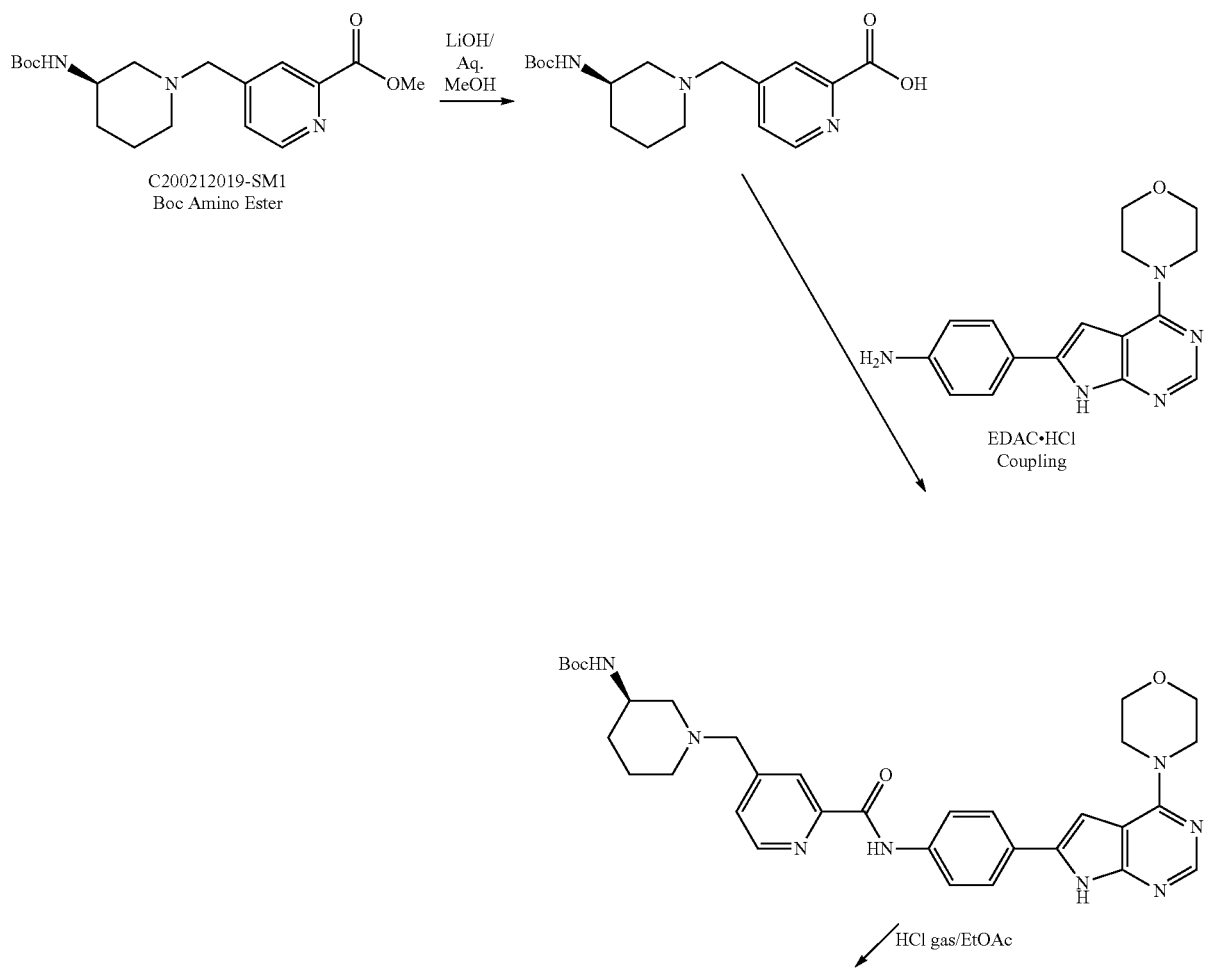

-continued

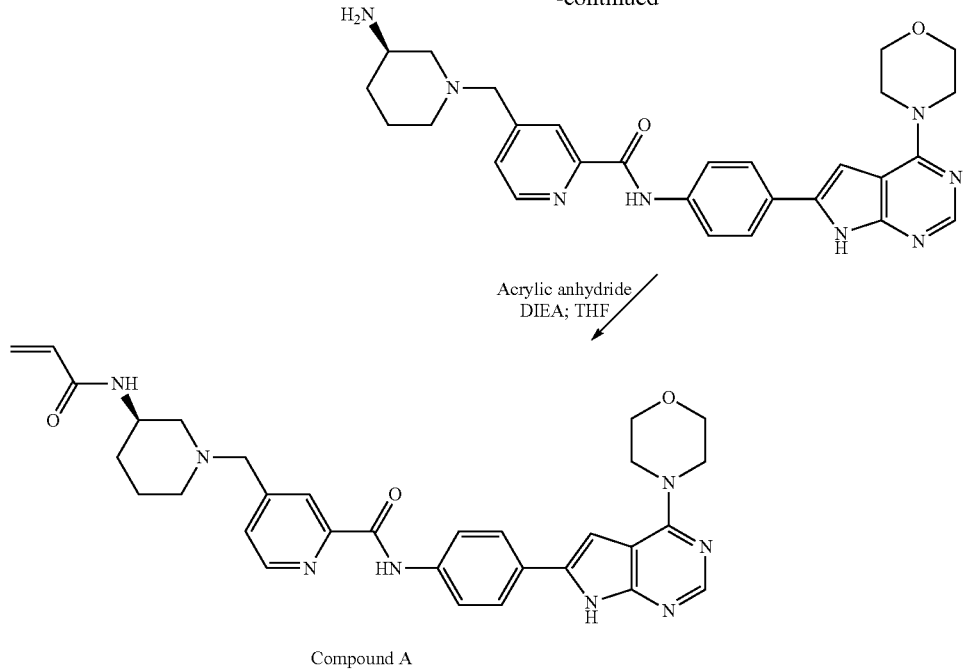

Compound A

Example 1: Preparation of Crystalline Forms of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A)

Preparation of Polymorph Pattern A

Compound A as an HCl salt was dissolved in deionized water (3.00 volumes) and sat. aq. NaHCO$_3$ was slowly added to the mixture until the solution was neutral (pH=7). Solid was precipitated out during the addition. The solid was collected by filtration and washed with MeOH (2.00 volumes). The filter cake was dried in an oven at 45° C. for 24 hrs to obtain Compound A as free base.

Preparation of Pattern B

Compound A was dissolved in DCM:MeOH (1:1, 150 volumes) and resin (SMA-905, 50% weight) was added. The mixture was then stirred at 65° C. for 12 hrs. Then the mixture was cooled to 25° C. and was filtered. The filtrate was concentrated under vacuum to provide Compound A.

Preparation of Polymorph Pattern C

Pattern C was successfully prepared using the procedure below.
  About 200 mg of Compound A, was weighed into a 4 mL glass vial. TFE (2.2 mL) was then added to the vial.
  The resulting suspension was kept as a slurry at 50° C. for about two hours; the slulrry was then kept stirring for about three days with protection from light.
  Solids were isolated by filtration and the wet cake was investigated by XRPD.
  Medium crystalline Pattern C was obtained as a pale yellow solid. Solids were further characterized by XRPD, TGA, DSC, and $^1$H NMR.

Characterization of Pattern C

| Characterization of Pattern C | | |
|---|---|---|
| Sample ID | | Pattern C |
| Parameters | Method | Results |
| Yield | | // |
| Purity | HPLC | // |
| DSC melting onset | DSC, 10° C./min | After being dried in the fume hood: No obvious melting point 150.2° C. (53 J/g) Wet cake: no obvious melting point 69.4° C. (17 J/g); 154.0° C. (7 J/g) |
| X-ray diffraction | 3-40° (2 Theta) | Middle crystallinity Pattern C, FIG. 3A |
| Thermo-gravimetry | TGA, 10° C./min | After being dried in the fume hood: 18.3% @ 200° C. |
| Residual solvent | $^1$H NMR (DMSO-d$_6$) | After being dried in the fume hood: 19.2% TFE by weight (1.35 equivalent by molar ratio) |

Explanation "//": Not carried out

Preparation of Polymorph Pattern E

Pattern E (DMSO solvate): About 50 mg of Compound A was equilibrated in DMSO (0.4 mL) at 25° C. with stirring. After one day, additional DMSO (0.4 mL) was added to maintain the suspension. After equilibration for two weeks, solids were isolated by centrifugal filtration and Pattern E was obtained.

Preparation of Polymorph Pattern G

Pattern G (TFE solvate): about 30 mg of Compound A was dissolved in TFE (2 mL). The resulting solution was filtered via a 0.45 m nylon filter. The resulting clear solution was slowly evaporated at ambient temperature. After eight days, the residual solids were analyzed by XRPD and Pattern G was obtained.

Preparation of Polymorph Pattern F

Pattern F was successfully prepared using the procedure below.
- About 250 mg of Compound A, was weighed to an 8 mL glass vial. MeOH:DCM (1:1 v/v, 4 mL) was added to the vial.
- The resulting suspension was kept as a slurry at 25° C. for about two hours and then was stirred for about five days with protection from light.
- Solids were isolated by filtration and the wet cake was investigated by XRPD.
- High crystalline Pattern F was obtained as a pale yellow solid. Solids were further characterized by XRPD and $^1$H NMR.

Characterization of Pattern F

| Sample ID | | Pattern F |
|---|---|---|
| Parameters | Method | Results |
| Yield | | // |
| Purity | HPLC | // |
| DSC melting onset | DSC, 10° C./min | // |
| X-ray diffraction | 3-40° (2 Theta) | High crystallinity Pattern F FIG. 6A |
| Thermogravimetry | TGA, 10° C./min | // |

Explanation "//": Not carried out

Preparation of Pattern Polymorph D

Pattern D, Compound A, Pattern D-dry, was successfully prepared using the procedure below.
- About 500 mg of Compound A was weighed to an 8 mL glass vial. THF:water (80:20 v/v, 8 mL) was added to the vial.
- The resulting suspension was kept as a slurry at 50° C. for about four days with protection from light.
- Solids were isolated by filtration and the wet cake was dried at 50° C. under vacuum for about 3 h.
- High crystalline Pattern D was obtained as a pale yellow solid (54% yield). Dried solids were further characterized by XRPD, TGA, DSC, $^1$H NMR, KF, and DVS.

Preparation of Polymorph Pattern D-1

Pattern D, Compound A, Pattern D-THF-water-dry, was successfully prepared using the procedure below.
- About 8 g of Compound A was weighed to a 120 mL glass vial. THF:water (80:20 v/v, 80 mL) was added to the vial to maintain a suspension.
- The resulting suspension was kept as a slurry at 50° C. for about two days with protection from light.
- THF:water (80:20 v/v, 20 mL) was added to maintain the suspension.
- Solids were isolated by filtration and the wet cake was dried at 50° C. under vacuum for about 12 h.
- 6.66 g medium crystalline Pattern D was obtained as a pale yellow solid (82.5% yield).
- The dry solids were further characterized by XRPD, TGA, DSC, $^1$H NMR, and KF.

Preparation of amorphous free form by manually grinding

Amorphous free form, Pattern D-grinding-amorphous free form was successfully prepared using the procedure below.
- 2 g free form Pattern D was ground manually with a mortar and pestle for 10 min.
- 1.83 g amorphous free form was obtained as a pale-yellow solid (91.5% yield).
- A yellow powder was investigated by XRPD and mDSC.

Preparation of Amorphous Free Form by Manual Grinding

| Exp. ID | XRPD | mDSC |
|---|---|---|
| GSE1(50 mg)(trial) | Amorphous form FIG. 22 | Glass transition: midpoint 137.1° C., ΔCp 0.3/(g.° C.) FIG. 23 |
| GSE1(600 mg) (trial) | Amorphous form FIG. 24 | Glass transition: midpoint 137.1° C., ΔCp 0.2/(g.° C.) FIG. 25 |
| GSE3(2 g) | Amorphous form FIG. 26 | Glass transition: midpoint 137° C., ΔCp 0.2/(g.° C.) FIG. 27 |

Characterization of Compound A amorphous free form, sample Pattern D-grinding-amorphous free form is reported the following table.

Characterization of Compound A Form Pattern D, sample scale up-Pattern D-THF-water-dry is reported in the following table.

| Polymorph | | Free form Pattern D | Free form Pattern D | Amorphous free form |
|---|---|---|---|---|
| Batch no. | | Pattern D-dry | Pattern D-THF-water-dry | Pattern D-grinding-amorphous free form |
| Parameters | Method | Results | | |
| Yield | | 54% | 82.5% | 91.5% |
| Purity | HPLC | 96.9% | 97.8% | 97.9% |
| X-ray diffraction | 3-40° (2 Theta) | High crystallinity Pattern D Figure FIG. 13 | Medium crystallinity Pattern D FIG. 18 | Amorphous form FIG. 26 |
| Melting onset and enthalpy | DSC, 10° C./min | Endothermic onset: 31.5° C. (47 J/g) FIG. 15 | Endothermic: 31.6° C.(18 J/g); melting onset: 268.6° C.(68 J/g) FIG. 20 | mDSC: glass transition: midpoint 137° C., ΔCp 0.2/(g.° C.) FIG. 27 |

| | | -continued | | |
|---|---|---|---|---|
| Thermogravimetry | TGA, 10° C./min | 2.7% @ 160° C. FIG. 14 | 1.4% @ 100° C. FIG. 19 | // |
| Residual solvent | ¹H-NMR (DMSO-d6) | No residual solvent FIG. 16 | No residual solvent FIG. 21 | // |
| Water content | Karl Fisher | 2.9% water by weight (0.9 equivalent by molar ratio) | 1.4% water by weight (0.5 equivalent by molar ratio) | 4.5% water by weight (1.5 equivalent by molar ratio) |
| Morphology | PLM/SEM | Aggregated crystals FIG. 17 | // | // |

Explanation "//": Not carried out

Preparation of Polymorph Pattern J

Compound A as an HCl salt was dissolved in deionized water (3.00 volumes) and sat. aq. NaHCO₃ was slowly added to the mixture until pH=7. Solids were precipitated out during the addition. Then the solids were collected by filtration and washed with MeOH (2.00 volumes). The filter cake was dried in an oven at 45° C. for 24 hrs to provide Compound A as Pattern J.

Example 2: X-Ray Powder Diffraction (XRPD)

X-ray powder diffraction patterns were collected on a Bruker AXS C2 GADDS or Bruker AXS D8 diffractometer.
Bruker AXS C2 GADDS X-ray Powder Diffraction patterns were collected on a Bruker AXS C2 GADDS diffractometer using Cu Kα radiation (40 kV, 40 mA), automated XYZ stage, laser video microscope for auto-sample positioning, and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate). The beam divergence (i.e., the effective size of the X-ray beam on the sample) was approximately 4 mm. A θ-θ continuous scan mode was employed with a sample—detector distance of 20 cm which gives an effective 2θ range of 3.2°—29.7°. Typically the sample would be exposed to the X-ray beam for 120 seconds. The software used for data collection was GADDS for WNT 4.1.16 and the data were analysed and presented using Diffrac Plus EVA v11.0.0.2 or v13.0.0.2.

Ambient Conditions

Samples run under ambient conditions were prepared as flat plate specimens using powder as received without grinding. Approximately 1-2 mg of the sample was lightly pressed on a glass slide to obtain a flat surface.

Non-Ambient Conditions

Samples run under non-ambient conditions were mounted on a silicon wafer with a heat conducting compound. The sample was then heated to the appropriate temperature at 10° C./min (unless otherwise stated) and subsequently held isothermally for one minute before data collection was initiated.
Bruker AXS D8 Advance X-ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analysed and presented using Diffrac Plus EVA v11.0.0.2 or v13.0.0.2. Samples were run under ambient conditions as flat plate specimens using powder as received. The sample was gently packed into a cavity cut into a polished, zero-background (510) silicon wafer. The sample was rotated via its own plane during analysis. The details of the data collection are:

Angular range: 2 to 42 2θ
Step size: 0.05 2θ
Collection time: 0.5 s/step

XRPD on Form A

The X-ray powder diffraction for Form A is displayed in FIG. 1A. Characteristic peaks include 3.5±0.1° 2-Theta, 10.4±0.1° 2-Theta, 14.7±0.1° 2-Theta, 17.1±0.1° 2-Theta, 21±0.1° 2-Theta, 24.9±0.1° 2-Theta, 29.5±0.1° 2-Theta, and 34.1±0.1° 2-Theta.

XRPD on Form B

The X-ray powder diffraction for Form B is displayed in FIG. 2A. Characteristic peaks include 5.9±0.1° 2-Theta, 8.6±0.1° 2-Theta, 10.5±0.1° 2-Theta, 12.6±0.1° 2-Theta, 16.9±0.1° 2-Theta, 19±0.1° 2-Theta, 20.5±0.1° 2-Theta, and 24.6±0.1° 2-Theta.

XRPD on Form C

The X-ray powder diffraction for Form C is displayed in FIG. 3A. Characteristic peaks include 5.2±0.1° 2-Theta, 5.9±0.1° 2-Theta, 7.2±0.1° 2-Theta, 8.7±0.1° 2-Theta, 10.6±0.1° 2-Theta, 12.2±0.1° 2-Theta, 14.3±0.1° 2-Theta, 15.1±0.1° 2-Theta, 15.9±0.1° 2-Theta, 17.5±0.1° 2-Theta, 18.1±0.1° 2-Theta, and 20.1±0.1° 2-Theta.

XRPD on Form D

The X-ray powder diffraction for Form D is displayed in FIG. 4A. Characteristic peaks include 3.4±0.1° 2-Theta, 5.3±0.1° 2-Theta, 7±0.1° 2-Theta, 8.7±0.1° 2-Theta, 10.8±0.1° 2-Theta, 12.9±0.1° 2-Theta, 14.3±0.1° 2-Theta, 15.6±0.1° 2-Theta, 17±0.1° 2-Theta, 18.5±0.1° 2-Theta, 19.6±0.1° 2-Theta, 21.5±0.1° 2-Theta, and 24.2±0.1° 2-Theta Crystallinity was unaffected after one week of storage at 40° C./75% RH, or after one week of storage at 25° C./92% RH.

XRPD on Form E

The X-ray powder diffraction for Form E is displayed in FIG. 5A. Characteristic peaks include 3.4±0.1° 2-Theta, 4.7±0.1° 2-Theta, 6.3 0.1° 2-Theta, 6.9±0.1° 2-Theta, 7.1±0.1° 2-Theta, 7.6±0.1° 2-Theta, 8.6±0.1° 2-Theta, 9.3±0.1° 2-Theta, 10.8±0.1° 2-Theta, 12±0.1° 2-Theta, 12.5±0.1° 2-Theta, 13±0.1° 2-Theta, 13.8±0.1° 2-Theta, 15.7±0.1° 2-Theta, 16.2±0.1° 2-Theta, 16.7±0.1° 2-Theta, 17±0.1° 2-Theta, 17.5±0.1° 2-Theta, 18.4±0.1° 2-Theta, 18.6±0.1° 2-Theta, 19.6±0.1° 2-Theta, 20.7±0.1° 2-Theta, 21.4±0.1° 2-Theta, 22.2±0.1° 2-Theta, 23±0.1° 2-Theta, 24.2±0.1° 2-Theta, 25.3±0.1° 2-Theta, 26±0.1° 2-Theta, 28±0.1° 2-Theta, 29.2±0.1° 2-Theta, 30.5±0.1° 2-Theta, 31.6±0.1° 2-Theta, 33.6±0.1° 2-Theta, and 34.5±0.1° 2-Theta.

XRPD on Form F

The X-ray powder diffraction for Form F is displayed in FIG. 6A. Characteristic peaks include 4.2±0.1° 2-Theta, 6.3±0.1° 2-Theta, 8.6±0.1° 2-Theta, 8.8±0.1° 2-Theta, 12±0.1° 2-Theta, 12.2±0.1° 2-Theta, 12.5±0.1° 2-Theta, 14.4±0.1° 2-Theta, 15±0.1° 2-Theta, 16±0.1° 2-Theta, 16.8±0.1° 2-Theta, 17.2±0.1° 2-Theta, 17.5±0.1° 2-Theta, 17.8±0.1° 2-Theta, 18.8±0.1° 2-Theta, 19.2±0.1° 2-Theta, 20.1±0.1° 2-Theta, 20.5±0.1° 2-Theta, 21.7±0.1° 2-Theta, 22.1±0.1° 2-Theta, 23.4±0.1° 2-Theta, 24.2±0.1° 2-Theta, 25.3±0.1° 2-Theta, 25.5±0.1° 2-Theta, 26.3±0.1° 2-Theta, 27.1±0.1° 2-Theta, 29±0.1° 2-Theta, 30.3±0.1° 2-Theta, 31.6±0.1° 2-Theta, 33.1±0.1° 2-Theta, 34.3±0.1° 2-Theta, and 35.6±0.1° 2-Theta.

XRPD on Form G

The X-ray powder diffraction for Form G is displayed in FIG. 7A. Characteristic peaks include 8±0.1° 2-Theta, 10.2±0.1° 2-Theta, 12.1±0.1° 2-Theta, 16.8±0.1° 2-Theta, 19.2±0.1° 2-Theta, and 24.6±0.1° 2-Theta.

XRPD on Form J

The X-ray powder diffraction for Form J is displayed in FIG. 8A. Characteristic peaks include 3.5±0.1° 2-Theta, 4.5±0.1° 2-Theta, 6.4±0.1° 2-Theta, 8.7±0.1° 2-Theta, 10.2±0.1° 2-Theta, 11.3±0.1° 2-Theta, 11.8±0.1° 2-Theta, 13.2±0.1° 2-Theta, 13.6±0.1° 2-Theta, 14±0.1° 2-Theta, 14.6±0.1° 2-Theta, 15.4±0.1° 2-Theta, 16.1±0.1° 2-Theta, 16.6±0.1° 2-Theta, 16.9±0.1° 2-Theta, 17.2±0.1° 2-Theta, 18.3±0.1° 2-Theta, 19.1±0.1° 2-Theta, 20.5±0.1° 2-Theta, 20.8±0.1° 2-Theta, 21.6±0.1° 2-Theta, 23.5±0.1° 2-Theta, 23.8±0.1° 2-Theta, 24.6±0.1° 2-Theta, 24.9±0.1° 2-Theta, 25.2±0.1° 2-Theta, 25.8±0.1° 2-Theta, 26.2±0.1° 2-Theta, 26.7±0.1° 2-Theta, 26.8±0.1° 2-Theta, 27.4±0.1° 2-Theta, 27.7±0.1° 2-Theta, 28.7±0.1° 2-Theta, 29.3±0.1° 2-Theta, 30.1±0.1° 2-Theta, 31.2±0.1° 2-Theta, 31.8±0.1° 2-Theta, 34.1±0.1° 2-Theta, 34.9±0.1° 2-Theta, 35.6±0.1° 2-Theta, 36.4±0.1° 2-Theta, 36.7±0.1° 2-Theta, 38.5±0.1° 2-Theta, and 38.8±0.1° 2-Theta.

Simulated XRPD on Form D

A simulated XRPD pattern was generated for Form D. The X-ray powder diffraction simulated pattern for Form D is displayed in FIG. 4A. Characteristic peaks include 5.3±0.1° 2-Theta, 7±0.1° 2-Theta, 8.7±0.1° 2-Theta, 10.8±0.1° 2-Theta, 12.9±0.1° 2-Theta, 14.3±0.1° 2-Theta, 15.6±0.1° 2-Theta, 17±0.1° 2-Theta, 18.5±0.1° 2-Theta, 19.6±0.1° 2-Theta, 21.5±0.1° 2-Theta, and 24.2±0.1° 2-Theta.

Example 4: Fourier Transform—Infra-Red (FTTR)

Data were collected on a Perkin-Elmer Spectrum One fitted with a universal Attenuated Total Reflectance (ATR) sampling accessory. The data were collected and analysed using Spectrum v5.0.1 software.

The infrared spectrum for Form D is displayed in FIG. 9A. Characteristic peaks observed in the infrared spectrum for Form D include peaks at about 3332 cm$^{-1}$ (not labeled), about 2853 cm$^{-1}$ (not labeled), about 1561 cm$^{-1}$ (not labeled), about 1523 cm$^{-1}$, about 1438 cm$^{-1}$, about 1257 cm$^{-1}$, 1112 cm$^{-1}$, and about 930 cm$^{-1}$.

Example 5: Differential Scanning Calorimetry (DSC) and Thermo-Gravimetric Analysis (TGA)

DSC data were collected on a TA Instruments Q2000 equipped with a 50 position autosampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 300° C. A purge of dry nitrogen at 50 mL/min was maintained over the sample, unless otherwise stated.

Modulated temperature DSC was carried out using an underlying heating rate of 2° C./min and temperature modulation parameters of ±0.318° C. (amplitude) every sixty seconds (period). The instrument control software was Advantage for Q Series v2.8.0.392 and Thermal Advantage v4.8.3 and the data were analysed using Universal Analysis v4.4A.

TGA data were collected on a TA Instruments Q500 TGA, equipped with a sixteen-position autosampler. The instrument was temperature calibrated using certified Alumel and Nickel. Typically 3-10 mg of each sample was loaded onto a pre-tared aluminium DSC pan and heated at 10° C./min from ambient temperature to 350° C. A nitrogen purge at 60 mL/min was maintained over the sample, unless otherwise stated. The instrument control software was Advantage for Q Series v2.8.0.392 and Thermal Advantage v4.8.3 and the data were analysed using Universal Analysis v4.4A.

Form A

In the DSC (rate of heating: 10° C./min or 20° C./min) an endotherm was observed having an onset at about 234.6° C. and a peak at about 245° C.

Form C

In the DSC (rate of heating: 10° C./min or 20° C./min) an endotherm was observed having an onset at about 150-151° C. and a peak at about 156-157° C.

Form D

In the DSC (rate of heating: 10° C./min or 20° C./min) an endotherm was observed having an onset at about 260-261° C. and a peak at about 273° C.

Form E

In the DSC (rate of heating: 10° C./min or 20° C./min) an endotherm was observed having an onset at about 112-113° C. and a peak at about 137-138° C.

In some embodiments, Form A is greater than 95% pure by HPLC analysis. In some embodiments, Form A is greater than 96% pure by HPLC analysis. In some embodiments, Form A is greater than 97% pure by HPLC analysis. In some embodiments, Form A is greater than 98% pure by HPLC analysis. In some embodiments, Form A is greater than 99% pure by HPLC analysis. In some embodiments, Form A is 99.8% pure by HPLC analysis.

In some embodiments, Form B is greater than 95% pure by HPLC analysis. In some embodiments, Form B is greater than 96% pure by HPLC analysis. In some embodiments, Form B is greater than 97% pure by HPLC analysis. In some embodiments, Form B is greater than 98% pure by HPLC analysis. In some embodiments, Form B is greater than 99% pure by HPLC analysis. In some embodiments, Form B is 97.8% pure by HPLC analysis. In some embodiments, Form B is 99.8% pure by HPLC analysis.

In some embodiments, Form C is greater than 95% pure by HPLC analysis. In some embodiments, Form C is greater than 96% pure by HPLC analysis. In some embodiments, Form C is greater than 97% pure by HPLC analysis. In some embodiments, Form C is greater than 98% pure by HPLC analysis. In some embodiments, Form C is greater than 99% pure by HPLC analysis. In some embodiments, Form C is 99.4% pure by HPLC analysis.

In some embodiments, Form D is greater than 95% pure by HPLC analysis. In some embodiments, Form D is greater than 96% pure by HPLC analysis. In some embodiments, Form D is greater than 97% pure by HPLC analysis. In some embodiments, Form D is greater than 98% pure by HPLC analysis. In some embodiments, Form D is greater than 99% pure by HPLC analysis. In some embodiments, Form D is 99.4% pure by HPLC analysis.

In some embodiments, Form E is greater than 95% pure by HPLC analysis. In some embodiments, Form E is greater than 96% pure by HPLC analysis. In some embodiments, Form E is greater than 97% pure by HPLC analysis. In some embodiments, Form E is greater than 98% pure by HPLC analysis. In some embodiments, Form E is greater than 99% pure by HPLC analysis. In some embodiments, Form E is 99.4% pure by HPLC analysis.

In some embodiments, Form F is greater than 95% pure by HPLC analysis. In some embodiments, Form F is greater than 96% pure by HPLC analysis. In some embodiments, Form F is greater than 97% pure by HPLC analysis. In some embodiments, Form F is greater than 98% pure by HPLC analysis. In some embodiments, Form F is greater than 99% pure by HPLC analysis. In some embodiments, Form F is 99.4% pure by HPLC analysis.

In some embodiments, Form G is greater than 95% pure by HPLC analysis. In some embodiments, Form G is greater than 96% pure by HPLC analysis. In some embodiments, Form G is greater than 97% pure by HPLC analysis. In some embodiments, Form G is greater than 98% pure by HPLC analysis. In some embodiments, Form G is greater than 99% pure by HPLC analysis. In some embodiments, Form G is 99.4% pure by HPLC analysis.

Solid Oral Dosage Forms

In some embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is formulated into a solid oral dosage form. In some embodiments, the crystallinity of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is maintained in the solid oral dosage form. In some embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is formulated into tablets. In some embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is formulated into pills. In some embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is formulated into capsules. In some embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is placed into capsules without excipients or with excipients. In any of these embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is Form A. In any of these embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is Form B. In any of these embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is Form C. In any of these embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is Form D. In any of these embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is Form E. In any of these embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is Form F. In any of these embodiments, crystalline N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is a mixture of two or more crystalline forms selected from the group consisting of Form A, Form B, Form C, Form D, Form E, and Form F.

Example 6: Capsule Formulations

In one embodiment, capsule formulations of Compound A for administration to humans is prepared with the following ingredients:

TABLE 1

| | Capsule Formulations | | | | | | | |
|---|---|---|---|---|---|---|---|---|
| | 25 mg Capsule | | 100 mg Capsule | | 25 mg Capsule | | 200 mg Capsule | |
| Component | w/w % | mg/capsule | w/w % | mg/capsule | w/w % | mg/capsule | w/w % | mg/capsule |
| Crystalline Compound A | 20.6 | 25.0 | 15.7 | 100.0 | 20.6 | 25 | 15.7 | 100 |
| Starch 1500 | 37.2 | 45.16 | 52.0 | 330.6 | 37.2 | 45.2 | 28.4 | 180.6 |
| Lactose 316 | 35.6 | 43.44 | 27.3 | 173.8 | 35.8 | 43.4 | 27.3 | 173.8 |
| Crospovidone | 5.0 | 6.08 | 3.8 | 24.3 | 5.0 | 6.1 | 3.8 | 24.3 |
| Fumed silica | 1.0 | 1.22 | 0.8 | 4.9 | 1.0 | 1.2 | 0.8 | 4.86 |
| Magnesium stearate | 0.5 | 0.61 | 0.4 | 2.4 | 0.5 | 0.6 | 0.4 | 2.43 |
| Total intragranular | NA | NA | NA | NA | 76.4 | 121.5 | 76.4 | 485.9 |
| Starch 1500 (extragranular) | NA | NA | NA | NA | 23.6 | 37.5 | 23.6 | 150 |

In some embodiments, the manufacturing process includes the following steps: weigh the indicated amount of the components, mix together and add into an appropriate size capsule, and close the capsule. In some embodiments, the capsules are stored at room temperature for an extended period of time until they are used.

Example 7: Compound A

The process steps for manufacturing compound A capsules, 25 mg and 100 mg, are described below (Table 2 and Table 3). The API is blended with pregelatinized starch, lactose, crospovidone, and colloidal silicon dioxide in a tumble blender. The blend is milled (to de-lump) using a conical mill. The milled blend is blended again in the tumble blender. Magnesium stearate is added, and the powder is blended. The blend is roller compacted. For the 100 mg capsules, extra-granular pregelatinized starch is added to the granulation and blended. The final blend is filled into capsules using a semi-manual process. The capsules are dedusted/polished, checked for metals, and weight sorted.

TABLE 2

Composition of Compound A Capsules, 25 mg

| Component | Function | Quantity per Capsule (mg) |
|---|---|---|
| Compound A* | Active ingredient | 25.0 |
| Pregelatinized Starch** | Diluent | 45.2 |
| Lactose Monohydrate | Diluent | 43.4 |
| Crospovidone | Disintegrant | 6.1 |
| Collidal Silicon Dioxide | Glidant | 1.2 |
| Magnesium Stearate | Lubricant | 0.6 |
| Swedish Orange Gelatin Capsule | Capsule shell | 1 capsule (Nominal weight: 39) |

TABLE 3

Composition of Compound A Capsules, 100 mg

| Component | Function | Quantity per Capsule (mg) |
|---|---|---|
| Compound A * | Active ingredient | 100.0 |
| Pregelatinized Starch** | Diluent | 330.6 |
| Lactose Monohydrate | Diluent, binder | 173.7 |
| Crospovidone | Disintegrant | 24.3 |
| Collidal Silicon Dioxide | Glidant | 4.9 |
| Magnesium Stearate | Lubricant | 2.4 |
| White Opaque Gelatin Capsule | Capsule shell | 1 capsule (Nominal weight: 117) |

* A correction factor may be applied to account for the API potency.
**Pregelatinized Starch is adjusted to accommodate the API correction factor.

Example 8: Safety and Tolerability Study of Compound A in Chronic Lymphocytic Leukemia In an open-label, dose-escalation study of Compound A, the safety, tolerability, PK/PD, and clinical activity of escalating doses of Compound A are determined. The compound is administered daily in 28-day cycles using an accelerated titration design (ATD) with the dose escalation following a modified Fibonacci sequence (i.e., using the incremental ratios: 2.00 for the initial escalation, 1.67 for the second, 1.50 for the third, and then 1.33 for all subsequent dose levels) when administered to adult patients (i.e., individuals age≥18 years) with R/R acute leukemia including ALL, AML, and acute mixed-phenotype leukemia (AMPL).

Two separate dose escalations are performed in parallel, with the dose-escalation arms (Arm A, Arm B) selectively enrolling patients who are not (Arm A) or are (Arm B) receiving drugs that inhibit cytochrome P450 3A4 (CYP3A4) activity. Following determination of the optimal biologic doses (OBDs), two expansion cohorts (differentiated based on whether the patient is/is not receiving a CYP3A4 inhibitor) of approximately twelve patients with R/R acute leukemia each are performed during the latter part of Phase 1 to further assess the safety and tolerability of the agent when dosed at the OBDs and to identify initial efficacy signals. If a single OBD can be identified, a single expansion cohort of approximately twenty-four patients with R/R acute leukemia is to be performed.

Compound A is administered once daily as an oral dose in continuous 28-day cycles. Doses are escalated and/or expanded up to a potential maximum tolerated dose to determine optimum biological dose and recommended Phase 2 dose.

In a second phase, patients with acute leukemia are enrolled. Patients include subjects with R/R AML, ALL, or AMPL containing rearrangements of the mixed-lineage leukemia gene (MLL, aka Lysine Methyltransferase 2A, KMT2A), MLL/KMT2A partial tandem duplication (MLL-PTD), PICALM-AF10 (aka CALM-AF10) rearrangement, Nucleophosmin 1 (NPM1) mutation, translocations of meningioma-1 (MN1), or CCAAT Enhancer Binding Protein Alpha (CEBP/A) mutation. Patients are treated starting on day one for a 28-day continuous cycle. Patients are assessed for pharmacokinetics and pharmacodynamics throughout the study. Endpoints include complete remission, complete remission with partial hematological recovery, overall survival, and event-free survival.

Example 9: Safety and Tolerability Study of Compound A in Chronic Lymphocytic Leukemia Purpose: The purpose of this study is to establish the safety and optimal dose of orally administered Compound A (25 or 100 mg/day) in patients with B-cell chronic lymphocytic leukemia/small lymphocytic lymphoma/diffuse well-differentiated lymphocytic lymphoma.

Primary Outcome Measures: Safety and tolerability of Compound A (frequency, severity, and relatedness of adverse events).

Secondary Outcome Measures: Pharmacokinetic/Pharmacodynamic assessments. Tumor response: overall response rate as defined by recent guidelines on CLL and SLL (B cell lymphoma) and duration of response.

Eligibility: eighteen years and older; both genders are eligible.

Inclusion Criteria: 1. For treatment-naive group only: Men and women ≥sixty-five years of age with confirmed diagnosis of CLL/SLL, who require treatment per NCI or International Working Group guidelines 11-14. 2. For relapsed/refractory group only: Men and women ≥eighteen years of age with a confirmed diagnosis of relapsed/refractory CLL/SLL unresponsive to therapy (i.e., failed ≥2 previous treatments for CLL/SLL and at least one regimen had to have had a purine analog [e.g., fludarabine] for subjects with CLL). 3. Body weight ≥40 kg. 4. ECOG performance status of <2. 5. Agreement to use contraception during the study and for thirty days after the last dose of study drug if sexually active and able to bear children. 6. Willing and able to participate in all required evaluations and procedures in this study protocol including swallowing capsules without difficulty. 7. Ability to understand the purpose and risks of the study and provide signed and dated informed consent and authorization to use protected health information (in accordance with national and local subject privacy regulations).

Exclusion Criteria: 1. A life-threatening illness, medical condition or organ system dysfunction which, in the investigator's opinion, could compromise the subject's safety, interfere with the absorption or metabolism of Compound A PO, or put the study outcomes at undue risk. 2. Any immunotherapy, chemotherapy, radiotherapy, or experimental therapy within four weeks before first dose of study drug (corticosteroids for disease-related symptoms allowed but require 1-week washout before study drug administration). 3. Central nervous system (CNS) involvement by lymphoma. 4. Major surgery within four weeks before first dose of study drug. 5. Creatinine >1.5×institutional upper limit of normal (ULN); total bilirubin >1.5×ULN (unless due to Gilbert's disease); and aspartate aminotransferase (AST) or alanine aminotransferase (ALT) >2.5×ULN unless disease related. 6. Concomitant use of medicines known to cause QT prolongation or torsades de pointes. 7. Significant screening electrocardiogram (ECG) abnormalities including left bundle branch block, 2nd degree AV block type II, 3rd degree block, bradycardia, and QTc >470 msec. 8. Lactating or pregnant.

Example 10: Safety and Efficacy of Compound A in Subjects With Relapsed/Refractory (R/R) Mantle Cell Lymphoma (MCL)

The primary objective of this trial is to evaluate the efficacy of Compound A in relapsed/refractory (R/R) subjects with Mantle Cell Lymphoma (MCL). The secondary objective is to evaluate the safety of a fixed daily dosing regimen of Compound A (25 or 100 mg/day in the form of capsules) in this population.

Primary Outcome Measures: To measure the number of participants with a response to Compound A.

Secondary Outcome Measures: To measure the number of participants with adverse events as a measure of safety and tolerability. To measure pharmacokinetics to assist in determining how the body responds to the study drug. Patient reported outcomes (to measure the number of participants reported outcomes in determining the health related quality of life).

Eligibility: eighteen years and older; both genders are eligible.

Inclusion Criteria: Men and women ≥18 years of age. ECOG performance status of <2. Pathologically confirmed MCL, with documentation of either overexpression of cyclin D1 or t(11;14), and measurable disease on cross sectional imaging that is ≥2 cm in the longest diameter and measurable in two perpendicular dimensions. Documented failure to achieve at least partial response (PR) with, or documented disease progression after, the most recent treatment regimen. At least one, but no more than five, prior treatment regimens for MCL (Note: Subjects having received ≥2 cycles of prior treatment with bortezomib, either as a single agent or as part of a combination therapy regimen, will be considered to be bortezomib-exposed.). Willing and able to participate in all required evaluations and procedures in this study protocol including swallowing capsules without difficulty. Ability to understand the purpose and risks of the study and provide signed and dated informed consent and authorization to use protected health information (in accordance with national and local subject privacy regulations).

Major exclusion criteria: Prior chemotherapy within three weeks, nitrosoureas within six weeks, therapeutic anticancer antibodies within four weeks, radio- or toxin-immunoconjugates within ten weeks, radiation therapy within three weeks, or major surgery within two weeks of first dose of study drug. Any life-threatening illness, medical condition, or organ system dysfunction which, in the investigator's opinion, could compromise the subject's safety, interfere with the absorption or metabolism of Compound A capsules, or put the study outcomes at undue risk. Clinically significant cardiovascular disease such as uncontrolled or symptomatic arrhythmias, congestive heart failure, or myocardial infarction within six months of screening, or any Class 3 or Class 4 cardiac disease as defined by the New York Heart Association Functional Classification. Malabsorption syndrome, disease significantly affecting gastrointestinal function, or resection of the stomach or small bowel or ulcerative colitis, symptomatic inflammatory bowel disease, or partial or complete bowel obstruction. Any of the following laboratory abnormalities: 1. Absolute neutrophil count (ANC) <750 cells/mm$^3$ (0.75×109/L) unless there is documented bone marrow involvement. 2. Platelet count <50,000 cells/mm3 (50×109/L) independent of transfusion support unless there is documented bone marrow involvement. 3. Serum aspartate transaminase (AST/SGOT) or alanine transaminase (ALT/SGPT) ≥3.0× upper limit of normal (ULN). 4. Creatinine >2.0×ULN.

Example B1a

Pan KRAS In Vitro Inhibitory Activity

The present example evaluates the ability of compounds provided herein to inhibit proliferation of KRAS mutant cells.

The inhibitory effect on cell proliferation was investigated in the human pancreas KRAS mutated cell lines MIA PaCa-2, HuP-T4, HPAF-II, human lung KRAS mutated cell line NCI-H358, and human colon KRAS mutated cell lines SW837, SW60, and NCI-H747. Cells were maintained in RPMI-1640 medium (ThermoFisher catalog no. 61870036), Eagle's Minimum Essential medium (EMEM, ATCC catalog no. 30-2003), Leibovitz's L-15 medium (L-15, ATCC catalog no. 30-2008), and supplemented with 10% of Heat Inactivated FBS (ThermoFisher catalog no. A31605) and 1% Pen-Strep (ThermoFisher catalog no. 10378016) according to cell line vendor medium requirements and cultured at 37° C. in a humidified incubator with 5% $CO_2$. Cells were grown by adhering to culture flasks, and maintained at 70%-80% confluency.

ATP is present in all metabolically active cells and is considered as a marker for viable cells. The number of metabolically active live cells in culture was determined using the CellTiter-Glo kit (Promega catalog no. G7572), an ATP monitoring system based on the production of luminescence by the reaction of ATP with added UltraGlo® recombinant luciferase (Kawano et al., 2016, PLOS One, 8;11 (7): e0158888), according to the supplier's experimental recommendations. The cell proliferation assay was performed using a 96-well plate format.

Agent A was dissolved in DMSO (Sigma catalog no. D8418; purity ≥99.9%) to prepare a 10 mM stock solution. Eight concentrations of test compound were assessed in duplicate for each experimental run. 100% cell proliferation is represented by the untreated cells (0.2% DMSO).

On the day of the experiment (To), cells were detached with TrypLE (ThermoFisher catalog no. 12604054), quantified using the cell viability analyser NucleoCounter (Chemometec NC-200) and resuspended in fresh medium at a cell density of about 5000 cells per 200 µL medium. 200 µL of cell suspension were added to each well of a 96-well plate.

Compound A exhibited significantly greater growth inhibition of KRAS-mutated cell lines across all cancer cell types tested compared to a known KRAS therapeutic. Each KRAS mutation, irrespective of subtype, was sensitive to Compound A. Compound A exhibited high potency and growth inhibition of KRAS-mutated patient samples of CRC, NSCLC, and pancreatic cancer. Compound A was significantly more potent and exerted dramatically greater growth reduction of ex vivo patient samples compared to clinical reversible menin inhibitors. Compound A is potent as a single agent and exhibits advantages over a known KRAS therapeutic and over reversible menin inhibitors in CRC, NSCLC, and pancreatic preclinical models.

Example B1a

Compound a in Triple-Hit Lymphoma (THL), Double Expresser Lymphoma (DEL), and Multiple Myeloma (MM)

The present example evaluates the ability of compounds provided herein to inhibit Triple-Hit Lymphoma (THL), Double Expresser Lymphoma (DEL) DLBCL, and Multiple Myeloma in pre-clinical models.

THL and DEL represent subsets of DLBCL that exhibit poor response to standard R-CHOP/R-EPOCH therapy and have a high unmet clinical need. THL harbors translocations in MYC, and BCL2/BCL6 and DEL have high expression of MYC/BCL2. Collectively, they represent tumors that are highly MYC-driven. This example evaluates Compound A in THL and DEL preclinical models, as well as a panel of MM cell lines and patient samples exhibiting various mutations and cytogenetic translocations.

Compound A was tested against a THL cell line (VAL), and a DEL cell line (U2932). An expanded panel of DHL cell lines were tested for sensitivity to Compound A. Ex vivo patient samples of THL and MYC-amplified DLBCL were tested with Compound A. Sensitivity of THL and MYC-driven DLBCL in both in vitro and ex vivo models were compared with clinical reversible menin inhibitors. Compound A was tested against a panel of MM cell lines and ex vivo MM patient samples of p53del, 13qdel, and relapsed/refractory cases.

Compound A exhibited high potency against THL and DEL cell line models with complete growth inhibition. An expanded DHL cell line panel was highly sensitive to growth inhibition by Compound A. Compound A was highly potent against ex vivo patient samples with a THL/R-CHOP-refractory clinical profile, and a MYC amplification/R-EPOCH refractory clinical profile, with both models exhibiting complete growth inhibition. Compound A was significantly more potent and exerted markedly greater growth inhibition of both in vitro models of DHL/THL/DEL and ex vivo patient samples of THL/MYC amplified-DLBCL compared to clinical reversible menin inhibitors. MM cell lines harboring mutations in TP53, KRAS, and NRAS were sensitive to Compound A as a single agent, and achieving 100% growth inhibition at 1 µM exposure.

Combination treatments of Compound A with standard-of-care agents in MM cell lines was also explored. Compound A has demonstrated efficacy against a panel of ex vivo MM patient samples.

Compound A is a potent single agent in MYC-driven DHL/THL/DEL DLBCL subsets and exhibits multi-fold higher potency compared to clinical reversible menin inhibitors in these preclinical models. Compound A also exhibits activity as a single agent in MM cell lines and ex vivo patient samples.

Example B2a

This example describes a PhaseI first-in-human dose-escalation and dose-expansion study of Compound A, an oral covalent menin Inhibitor, in adult patients with relapsed or refractory (R/R) acute lymphocytic leukemia (ALL) or acute myeloid leukemia (MLL), R/R diffuse large B-cell lymphoma (DLBCL), and R/R multiple myeloma (MM). Additional conditions or diseases that can be treated include acute lymphoblastic leukemia, acute mixed-phenotype, leukemia, cancer, lymphoma, non-Hodgkin lymphoma, myelomatosis, plasma cell myeloma, and/or all R/R subtypes thereof.

Approximately one hundred participants can be enrolled for this PhaseI study. This study can be a non-randomized, unmasked, prospective, open-label, multi-cohort, and multicenter study evaluating the safety, tolerability, and clinical activity of escalating doses of oral Compound A administered once daily in patients with R/R ALL, R/R AML, R/R DLBCL, and R/R MM who have received standard therapy. During the dose-escalation phase of this study, the optimal biologic dose (OBD) and recommended Phase 2 dose (RP2D) of Compound A will be determined. Subjects in Cohort 1 (acute leukemia) are assigned to one of two parallel arms: ARM A (subjects not receiving CYP3A4 inhibitors), and ARM B (subjects receiving CYP3A4 inhibitors). Subjects in Cohort 2 (DLBCL) and Cohort 3 (multiple myeloma) are assigned to a single arm (ARM A). The dose-expansion phase will obtain further safety, as well as efficacy data for Compound A when dosed at the OBD and RP2D.

In ARM A, study participants who are not receiving a moderate or strong CYP3A4 inhibitor, there is a dose escalation phase for Cohort 1: participants with acute leukemia; Cohort 2: participants with diffuse large B-cell lymphoma; and Cohort 3: participants with multiple myeloma. Participants will receive 100 mg Compound A orally once per day in continuous twenty-eight day cycles to identify the OBD/RP2D. There is also a dose expansion phase where Cohorts 1, 2, and 3 will receive Compound A at the OPD/RP2D to further assess the safety/efficacy of the investigational drug.

In ARM B, study participants who are receiving a moderate or strong CYP3A4 inhibitor, there is a dose escalation phase for Cohort 1: participants with acute leukemia. Participants will receive 25 mg Compound A orally once per day in continuous twenty-eight day cycles to identify the OBD/RP2D. There is also a dose expansion phase where Cohort 1 will receive Compound A at the OBD/RP2D to further assess the safety and efficacy of the investigational drug.

Primary and secondary outcome measures for this study will be determined. The primary outcome measure is to determine OBD and RP2D of Compound A monotherapy for Cohorts 1, 2, and 3 within a time frame of twenty-eight days in subjects with refractory or relapsed (R/R) acute leukemia (Cohort 1), diffuse large B-cell lymphoma (Cohort 2), and multiple myeloma (Cohort 3). The secondary outcome measure is to evaluate the safety of Compound A as expressed by treatment-emergent adverse events (TEAEs) and serious adverse events (SAEs) within a time frame of thirty-two cycles.

Utilizing an accelerated titration design, doses of Compound A are escalated in single-subject cohorts independently for each indication until one subject experiences either a ≥Grade 2 related adverse event or dose limiting toxicity (DLT). At that point, the cohort will switch to a classical "3±3" design. Treatment continues in 28-day cycles until progression or intolerability. Expansion cohorts for each indication enroll patients to obtain further safety and efficacy data. Patients with R/R ALL, R/R DLBCL who receive ≥2 but ≤5 therapies, and R/R MM who receive ≥3 therapies and either fail or are ineligible for any standard therapies are eligible. Patients have ECOG PS≤2, and adequate organ function. Key exclusion criteria include known CNS disease involvement, prior menin inhibitor therapy, and clinically significant cardiovascular disease (FIG. 28A).

Inclusion criteria for this study includes persons aged eighteen years or more. All subjects must have histologically or pathologically confirmed diagnosis of their malignancy and/or measurable R/R disease, as follows:
1. Cohort 1 only: Refractory or relapsed acute leukemia defined as >5% blasts in the bone marrow or reappearance of blasts in the peripheral blood;
2. Cohort 2 only: Previously treated, pathologically confirmed de novo DLBCL, or DLBCL transformed from previously indolent lymphoma (e.g., follicular lymphoma) with documented clinical or radiological evidence of progressive or persistent disease. At study entry, subjects must have measurable disease as per the revised criteria for response assessment of lymphoma; and
3. Cohort 3 only: Measurable MM based on International Myeloma Working Group (IMWG) guidelines.

Patients must be refractory or must have progressed on, or following discontinuation of, the most recent anti-cancer therapy, with the following considerations:
1. Cohort 1 only: Have failed or are ineligible for any approved standard of care therapies, including Hematopoietic Stem Cell Transplantation (HSCT);
2. Cohort 2 only: Must have received at least two but no more than five previous systemic regimens for the treatment of their de novo or transformed DLBCL (i.e., transformed from a previously diagnosed indolent lymphoma [e.g., follicular lymphoma]); and
3. Cohort 3 only: Must have received at least three but no more than six prior anti-MM regimens including proteasome inhibitor (e.g., bortezomib or carfilzomib) and immunomodulatory drug (IMiD) (e.g., lenalidomide or pomalidomide) therapy.

Exclusion Criteria for this study is defined by subjects who meet any of the following criteria (all cohorts, unless otherwise indicated):
Certain disease subtypes or occurrences, as follows:
1. Cohort 1: acute promyelocytic leukemia (APL), chronic myeloid leukemia (CML) in blast crisis, isolated extramedullary relapse (iEMR);
2. Cohort 2: Primary mediastinal B-cell lymphoma (PMBCL), DLBCL transformed from diseases other than indolent non-Hodgkin's Lymphoma (NHL); and
3. Cohort 3: Active plasma cell leukemia, myeloma with amyloidosis, systemic light chain amyloidosis;
White Blood Count (WBC) >25,000/μL (uncontrollable with cytoreductive therapy);
Known central nervous involvement, as follows:
4. Cohort 1: Clinically active central nervous system (CNS) leukemia. Previously controlled CNS leukemia is acceptable;
5. Cohort 2: Active CNS lymphoma or meningeal involvement;

Prior menin inhibitor therapy;
Known positive test for human immunodeficiency virus, hepatitis C, or hepatitis B surface antigen;
Subjects with a pre-existing disorder predisposing them to a serious or life-threatening infection (e.g., cystic fibrosis, congenital or acquired immunodeficiency, bleeding disorder, or cytopenias not related to acute leukemia, DLBCL, or MM); and
An active uncontrolled acute or chronic systemic fungal, bacterial, or viral infection.

Example B2b

This example describes the anti-tumor activity of covalent menin inhibitor Compound A in high grade B-cell lymphoma and multiple myeloma preclinical models.

Figure 28B:
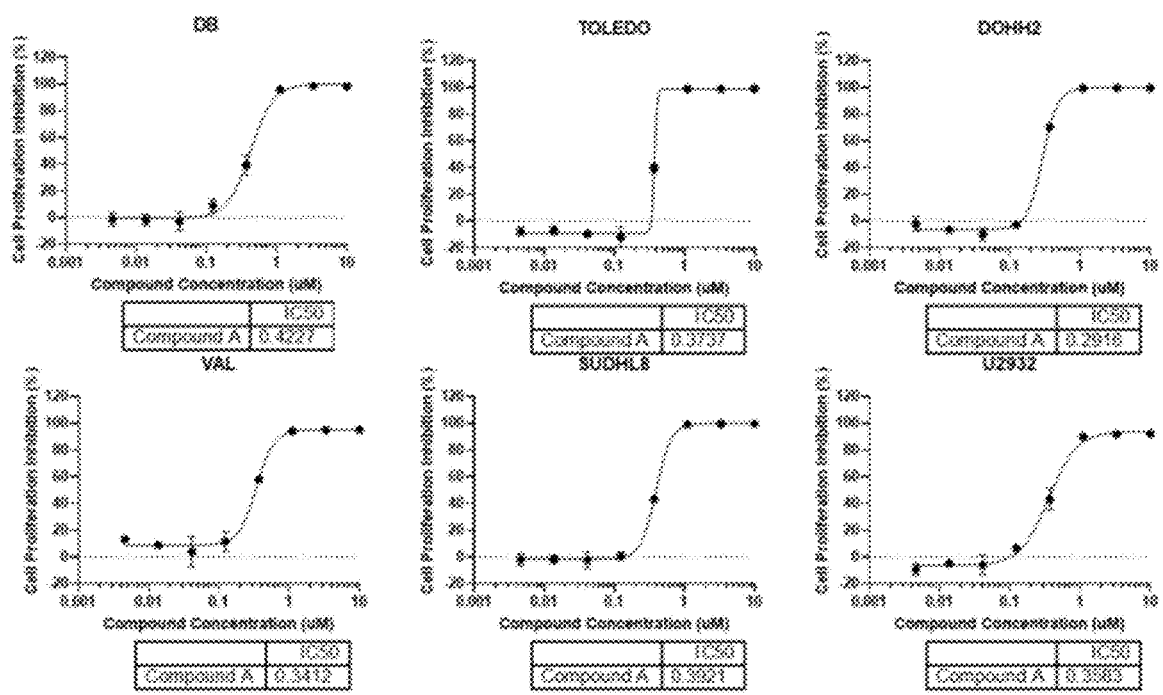
FIG. 28B shows anti-proliferative effects and potent cell lethality in representative DLBCL cell lines treated with Compound A or PS-341 after four days of treatment at eight dose concentrations ranging from 0.005 µM to 10 µM in DHL (DB, Toledo, DOHH2), THL (VAL), DEL (U2932), and GCB (SUDH8L) DLBCL subtypes.

DLBCL cell line TOLEDO was cultured in the presence of Compound A or clinical reversible menin inhibitors for six and fourteen hours. Menin protein expression was reduced up to 60% at 1 μM by Compound A after fourteen hours compared to clinical reversible inhibitors at <20% at similar concentrations. Menin protein expression was measured by the Wes system and analyzed using the Compass software (automated western blotting, Protein Simple). Signal was normalized to GAPDH and referenced to DMSO control (FIG. 28F). DLBCL and MM cell lines were cultured with Compound A, bortezomib (PS-341), or DMSO for four days and cell proliferation was measured by Cell Titer Glo. Ex vivo studies of DLBCL and MM models were conducted by measurement of cell proliferation (Cell Titer Glo) after six days of treatment with Compound A, PS-341, or DMSO control.

Figure 28C:
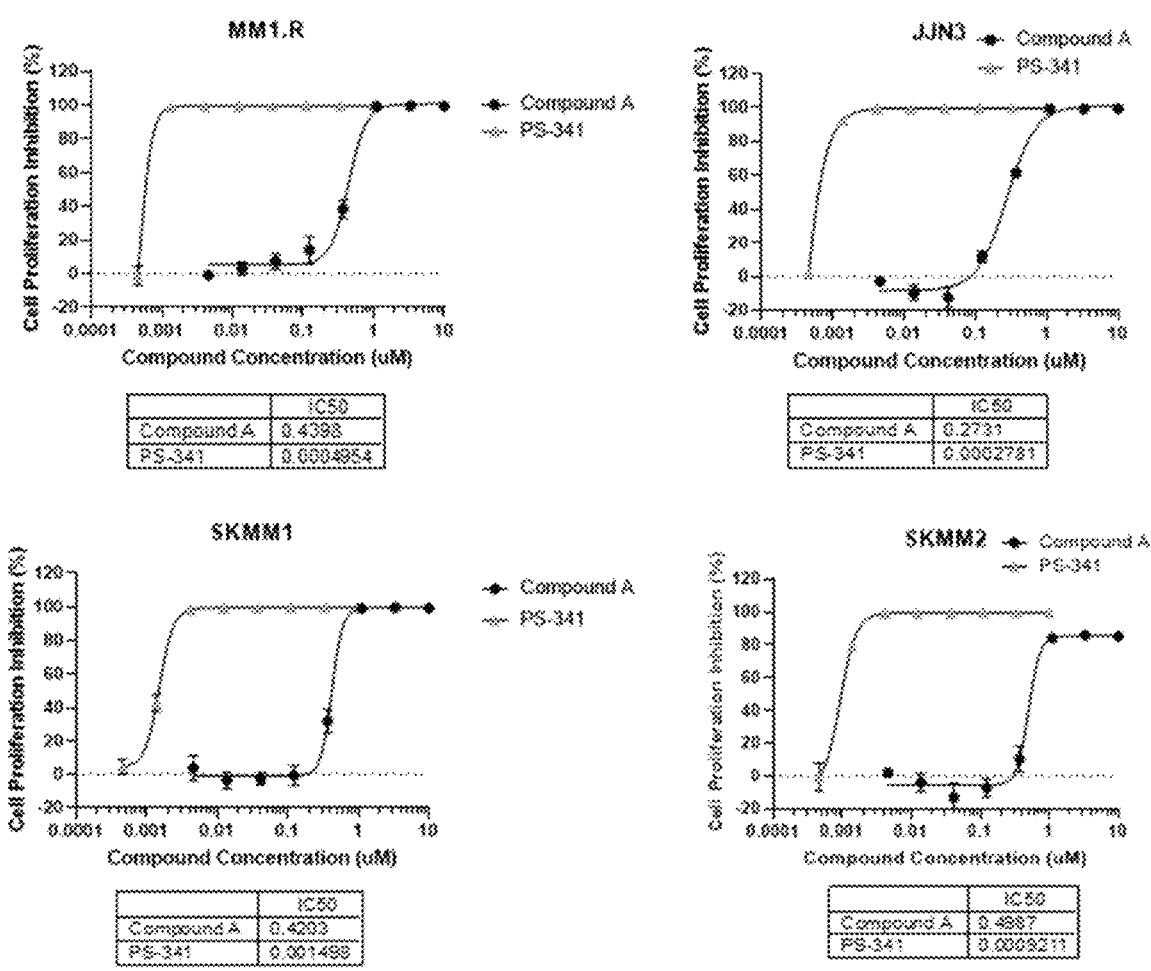
FIG. 28C shows anti-proliferative effects and cell lethality of representative MM cell lines treated with Compound A or PS-341 after four days of treatment at eight dose concentrations ranging from 0.005 µM to 10 µM in MM1.R, JJN3, SKMM1, and SKMM2 cell lines.
Figure 28D:
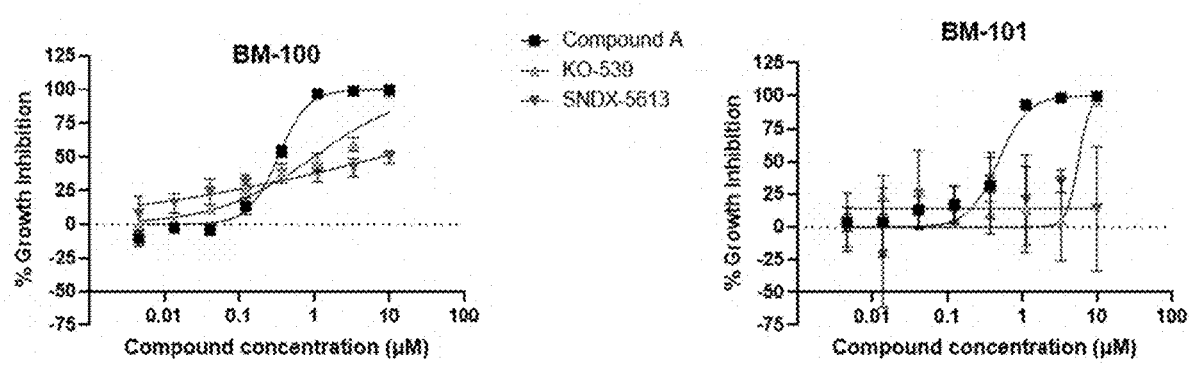
FIG. 28D shows relative viability of patient-derived DLBCL Triple Hit Lymphoma (THL) and MYC-amplified PDX samples treated with Compound A or clinical reversible menin inhibitors after six days of treatment.
Figure 28F:
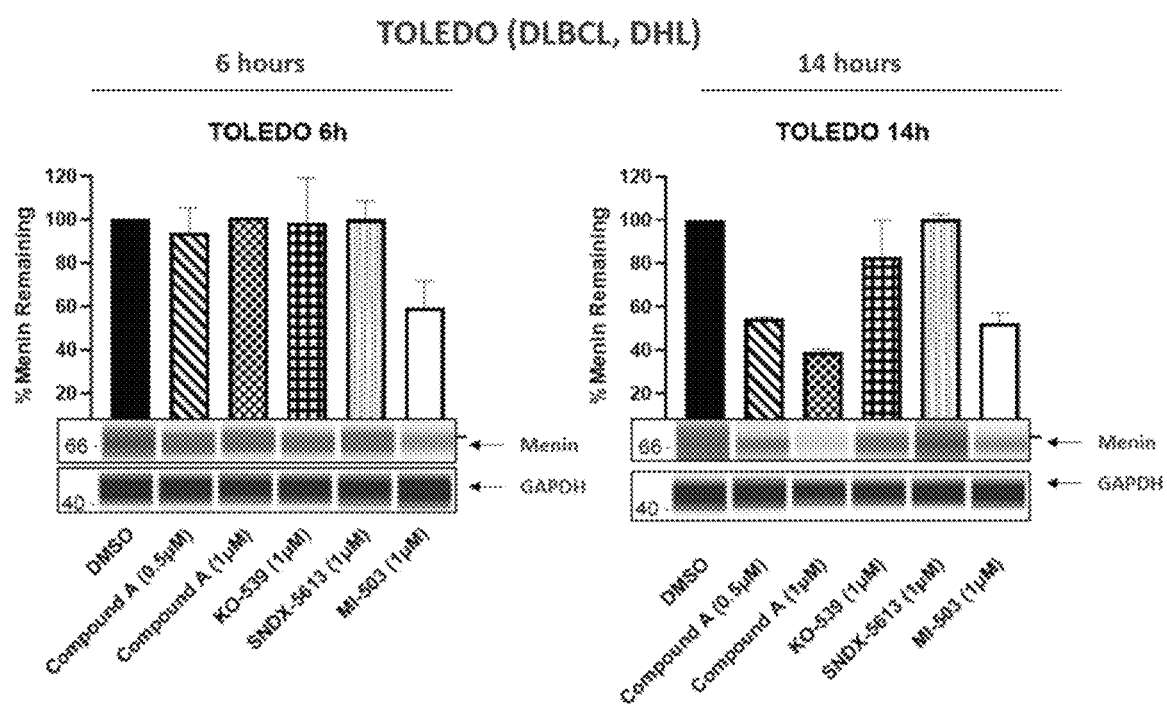
FIG. 28F shows Compound A reduces menin protein in DLBCL cells.

Compound A exhibited high potency and >90% cell lethality against DHL, THL, and DEL DLBCL cell lines (FIG. 28B, Table 4) and >99% cell lethality against MM cell lines (FIG. 28C, Table 5). Compound A exerted marked relative viability of THL and MYC-amplified DLBCL PDX models ex vivo (FIG. 28D). Compound A was highly potent against newly diagnosed and R/R MM patient-derived specimens (FIG. 28E).

TABLE 4

Compound A Achieves >90% of Cell Lethality in All DLBCL Cell Lines Tested

| DLBCL Cell Line | Category | Translocation | Average % Max Inhibition by Compound A | Average $IC_{50}$ ± Standard Deviation (μM) |
|---|---|---|---|---|
| DB | DHL | MYC/BCL2 | | |
| Toledo | DHL | MYC/BCL2 | 98.8 | 0.311 ± 0.065 |
| DOHH2 | DHL | MYC/BCL2 | 99.7 | 0.323 ± 0.031 |
| VAL | THL | MYC/BCL2/BCL6 | 97.1 | 0.271 ± 0.070 |
| U2932 | DEL-ABC | MYC/BCL2 Overexpression | 92.4 | 0.370 ± 0.012 |
| SUDHL8 | GCB | — | 99.6 | 0.601 ± 0.209 |
| Pfeiffer | GCB | — | 99.6 | 0.167 ± 0.040 |
| OCI-LY7 | GCB | — | 99.6 | 0.650 ± 0.260 |

TABLE 5

Compound A Achieves >99% of Cell Lethality in the Majority of MM Cell Lines Tested

| MM Cell Line | Translocation | Mutation | Inhibition by Compound A | Average $IC_{50}$ ± Standard Deviation (μM) |
|---|---|---|---|---|
| MM1.S | t(14; 16) | KRAS G12A | 99.5 | 0.467 ± 0.17 |
| MM1.R | t(14; 16) | KRAS G12A | 99.6 | 0.462 ± 0.17 |
| SKMM1 | t(14; 20) | NRAS G12A | 99.2 | 0.467 ± 0.05 |
| SKMM2 | t(11; 14) | TP53 | 80.2 | 0.654 ± 0.15 |
| JJN3 | t(14; 16) | NRAS Q61K | 99.2 | 0.289 ± 0.02 |

In ex vivo studies, Compound A was highly effective against R-CHOP and R-EPOCH refractory patient models with THL and MYC-amplified genetic backgrounds (FIG. 28D). Compound A demonstrated single-agent efficacy ($IC_{50}$ values between 0.1 μM and 0.3 μM) against a panel of newly diagnosed and R/R ex vivo MM samples (FIG. 28E), including a p53-deleted clinical profile (Table 6).

TABLE 6

Clinical Profiles of MM Patient-derived BMMC Specimens Tested With Compound A

| Multiple Myeloma Specimen ID | Stage at Diagnosis | Treatment Status | Prior Therapy and Response | Translocation |
|---|---|---|---|---|
| 16-669/0219 | IIIA | Newly Diagnosed | None | No data |
| 16-684/1019 | IIIA | Newly Diagnosed | None | No data |
| 241-9949/06-19 | IIIA | Refractory | VCD N4 (resistant) | p53 deletion |
| 241-10514/0720 | IIIA | Refractory | VCD N 4 (responded) High dose CPH (SC-mobilization) (responded) Consolidation (AutoSCT, double transplant) Bortezomib-maintenance (resistant) RVD #4 (resistant) PRD #4 (resistant) | p53 deletion-negative |

Example B3

This example describes Compound A as a covalent menin inhibitor for the growth inhibition of KRAS-mutated solid tumors.

MOLM-13 and MiaPaCa-2 cells were incubated with Compound A for twenty-four hours and were analyzed by RNA-seq on an Illumina NextSeq 550 platform. Compound A, clinically reversible menin inhibitors, or a clinically approved KRAS G12C inhibitor, sotorasib, were cultured with colorectal cancer (CRC), non-small cell lung cancer (NSCLC), and pancreatic cancer cell lines for four days. Cell viability was measured using CellTiter Glo. Human ex vivo PDX tissue models harboring KRAS mutations were cultured with Compound A and clinical reversible menin inhibitors for six days. Cell viability was measured using CellTiter Glo.

Figure 29:
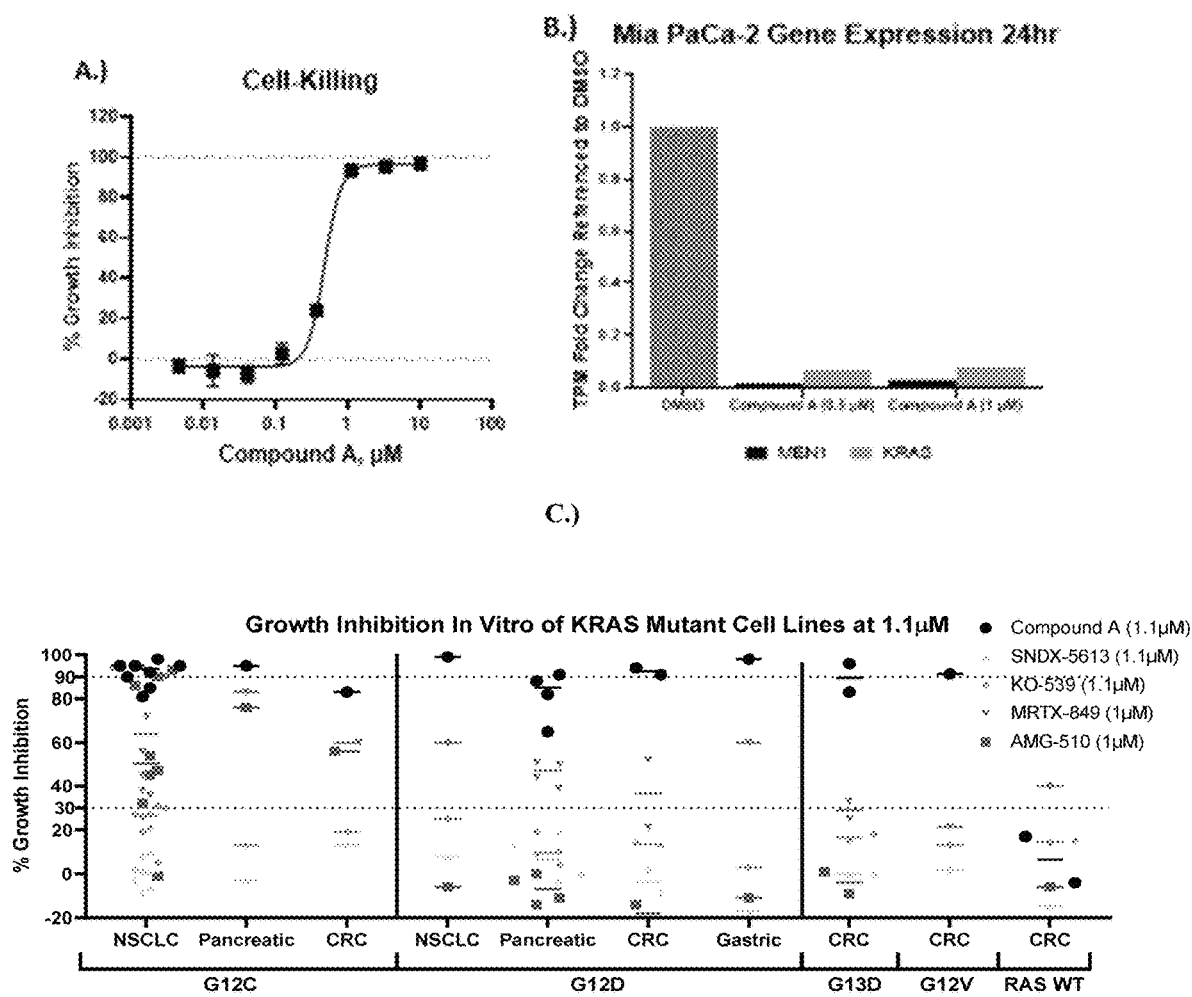
FIG. 29A shows Compound A induces cell killing of a KRAS G12C cell line.
FIG. 29B shows that KRAS and MEN1 KRAS mutated cell line gene expression changes.
FIG. 29C shows Compound A inhibits KRAS mutant cell growth in vitro.
Figure 30A:
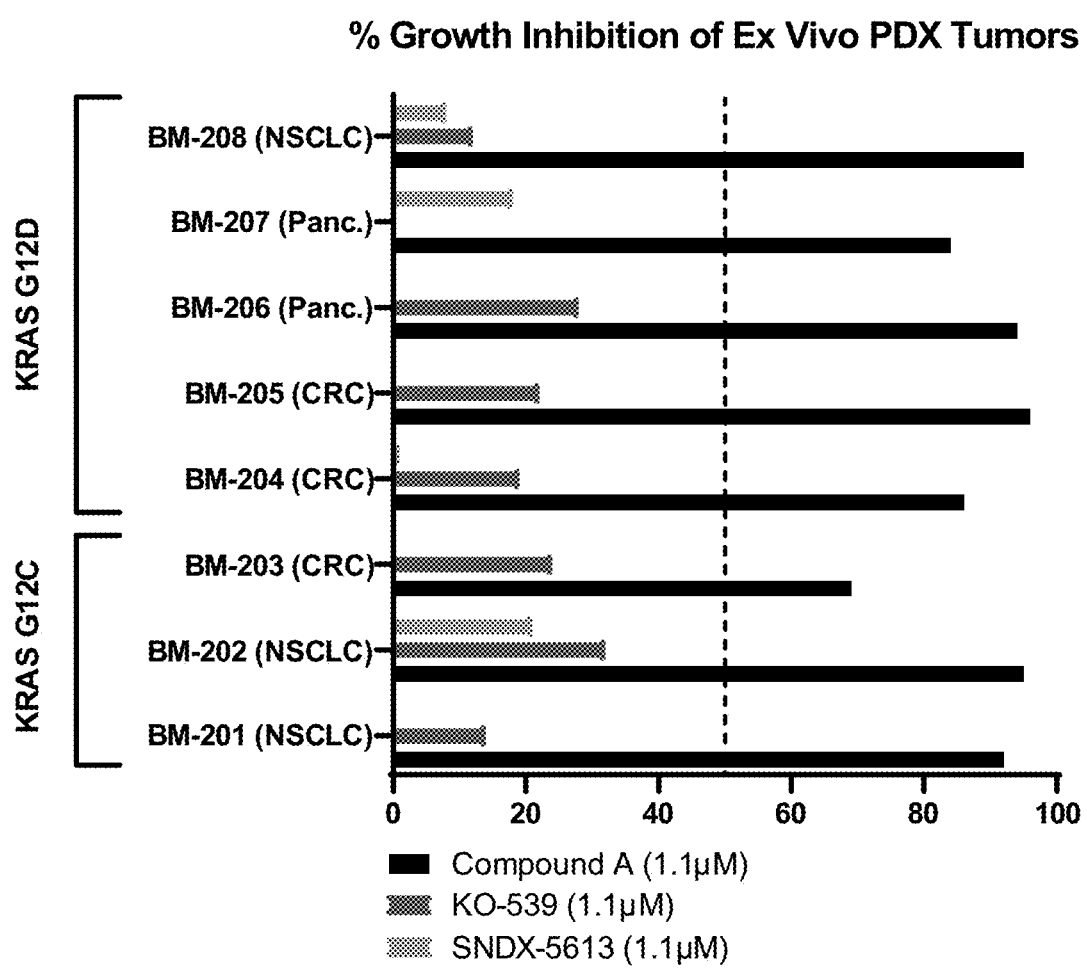
FIG. 30A shows % growth inhibition of ex vivo PDX tissues.
Figure 30B:
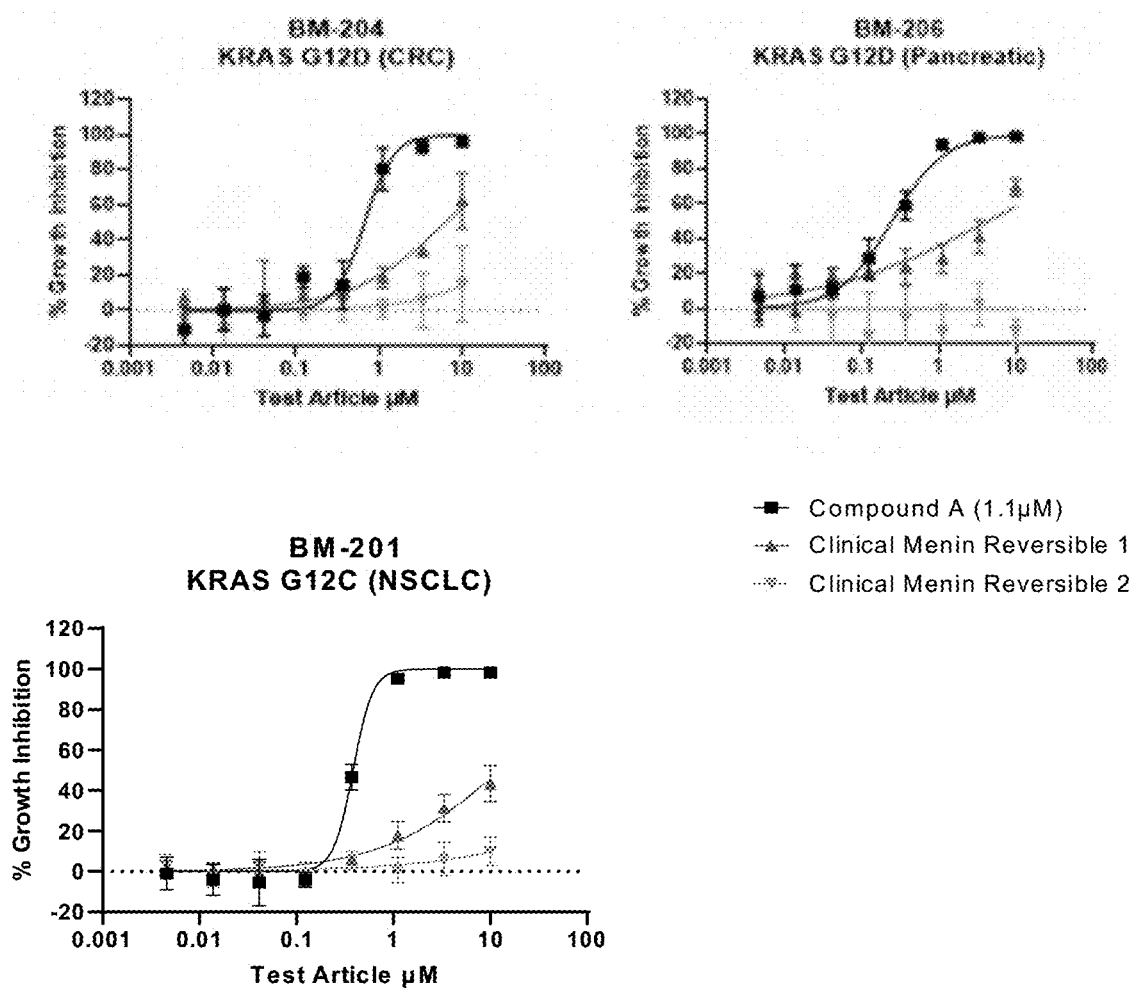
FIG. 30B shows ex vivo PDX tissue dose response curves.
Figure 32A:
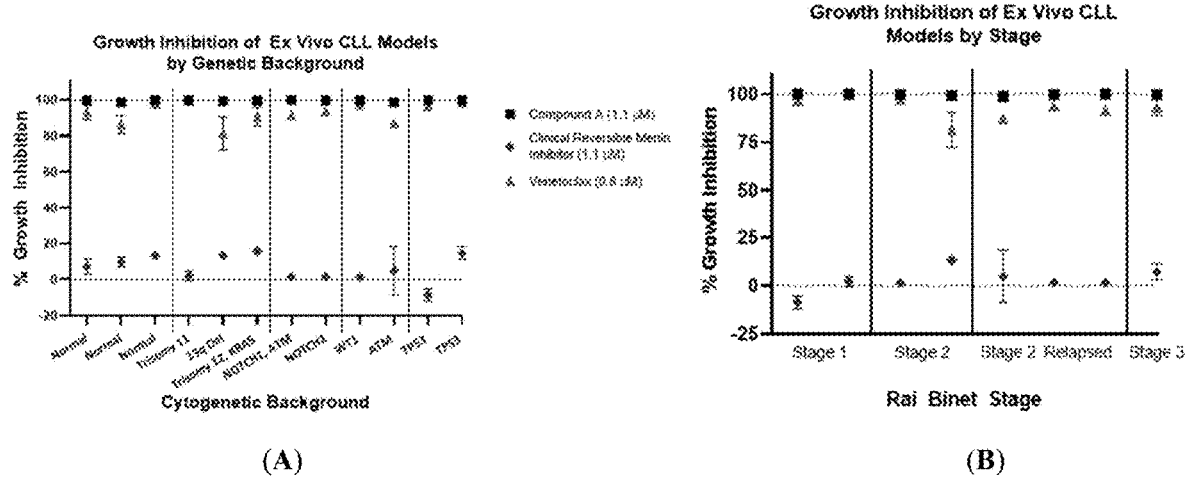
FIGS. 32A and 32B show growth inhibition of patient-derived CLL PDX samples treated with Compound A or clinical reversible menin inhibitors after six days of treatment, arranged by genetic background (A) or Rai-Binet Stage where data is available (B).
Figure 32B:
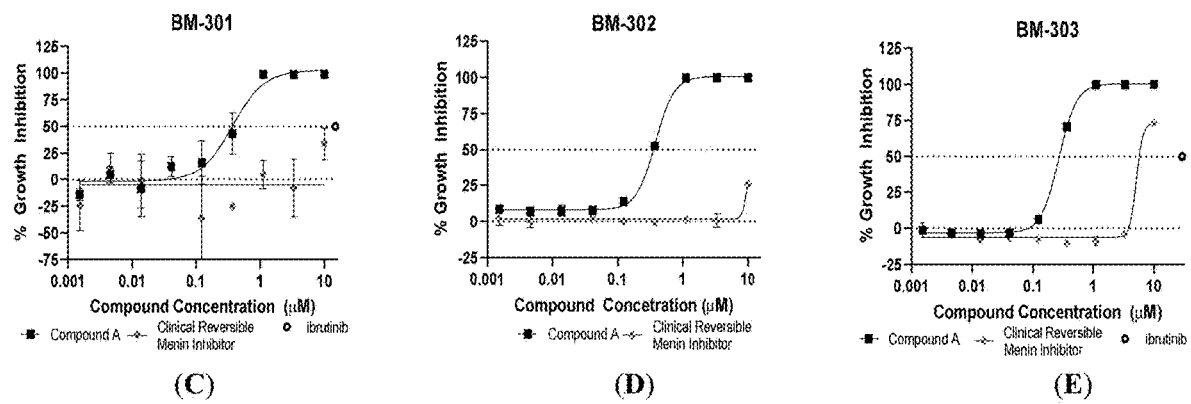
Figure 33:
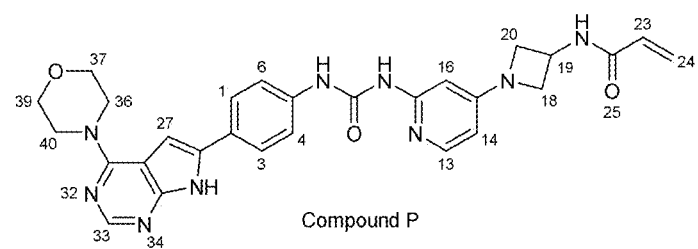
FIG. 33 depicts Compound P, a covalent inhibitor of menin-HLL interaction.

MiaPaCa-2, a KRAS G12C mutated cell line, showed % growth inhibition (FIG. 29A; plot represents three or more experiments) after four days of Compound A treatment, and marked reduction of KRAS and MEN1 expression levels in MiaPaCa-2 cells at 0.5 μM and 1 μM after twenty-four hours of Compound A treatment (FIG. 29B). An expanded panel of fourteen CRC, NSCLC, and pancreatic KRAS mutated cell lines, harboring G12C, G12D, G12V, and G13D mutations, revealed single agent Compound A activity after a four-day treatment. Most of the cell lines tested exhibited >90% inhibition of growth, independent of KRAS mutation type (FIG. 29C; each data point is the mean of two or more experiments). Sotorasib reached a maximum of 86-93% growth inhibition in three of ten KRAS G12C NSCLC cell lines (FIG. 29C). In contrast, Compound A inhibited cell viability ≥90% in seven of ten KRAS G12C NSCLC cell lines (FIG. 29C). Human CRC, NSCLC, and pancreatic ex vivo preclinical models with G12C and G12D KRAS mutations were all sensitive to Compound A six-day treatment (FIG. 30A). Complete abrogation of growth was observed in all samples with $GI_{50}$ values ranging between 0.2 μM-0.7 μM. Clinical reversible menin inhibitors were less active in all preclinical models tested (FIG. 30B).

Overall, MEN1 and KRAS gene expression dramatically decreased after twenty-four hour treatment with Compound A in KRAS G12C mutated cell line MIA PaCa-2 (Pancreatic cancer) (FIG. 29B). Single agent treatment of Compound A in vitro at 1 μM in KRAS-mutated cell lines demonstrated high growth inhibition across various tissue types compared to the standard of care KRAS G12C inhibitor, sotorasib, other clinical reversible menin inhibitors, and a clinical KRAS G12C covalent inhibitor, MRTX-849 (FIG. 29C). Compound A achieves high tumor growth inhibition broadly across KRAS-mutated ex vivo treated patient derived CRC, NSCLC, and pancreatic models (FIG. 30). And, in comparison to two highly specific KRAS G12C inhibitors, Compound A exhibited potency broadly across KRAS-mutated cell lines and PDX tissue models indicating Compound A may provide therapeutic advantages over these KRAS mutation-specific inhibitors for use in CRC, NSCLC, and pancreatic cancers. At clinically relevant concentrations, potent clinical KRAS inhibitors like sotorasib are highly efficacious up to 50% inhibition. However, at these concentrations Compound A is more proficient, achieving higher percent of cell killing, suggesting that Compound A produces an increase in the depth of response.

TABLE 7

KRAS Mutant Cell Line $GI_{50}$ Summary

| | KRAS G12C $GI_{50}$ (μM) | | | KRAS G12D $GI_{50}$ (μM) | | | | KRAS G13D $GI_{50}$ (μM) | KRAS G12V $GI_{50}$ (μM) | RAS WT $GI_{50}$ (μM) |
|---|---|---|---|---|---|---|---|---|---|---|
| Tumor Type | NSCLC (8) | Pancreatic (1) | CRC (1) | NSCLC (1) | Pancreatic (4) | CRC (2) | Gastric (1) | CRC (2) | CRC (1) | CRC (2) |
| Compound A | 0.36-0.57 | 0.43 | 0.57 | 0.29 | 0.43-0.83 | 0.42 | 0.34 | 0.37-0.57 | 0.45 | 1.6, LR |

TABLE 7-continued

KRAS Mutant Cell Line GI$_{50}$ Summary

| | KRAS G12C GI$_{50}$ (μM) | | | KRAS G12D GI$_{50}$ (μM) | | | | KRAS G13D GI$_{50}$ (μM) | KRAS G12V GI$_{50}$ (μM) | RAS WT GI$_{50}$ (μM) |
|---|---|---|---|---|---|---|---|---|---|---|
| Tumor Type | NSCLC (8) | Pancreatic (1) | CRC (1) | NSCLC (1) | Pancreatic (4) | CRC (2) | Gastric (1) | CRC (2) | CRC (1) | CRC (2) |
| SNDX-5613 | LR | LR | LR | LR | LR | LR | LR | LR | LR | LR |
| KO-539 | 1.8-6.2, LR | 3.1 | 6.9 | 2.0 | 4.1-7.2 | 6.5 | 3.8 | 3.9-6.3 | 3.2 | 3.3, LR |
| Clinical KRAS G12C Covalent, MRTX-849 | 0.026-4.7 | 0.0038 | 0.017 | 0.84 | 1.1-4.0 | 1.1 | 0.70 | 1.4-2.3 | 1.8 | 1.3 |
| Sotorasib KRAS G12C | 0.033-5.6, LR | 0.0054 | 0.035 | LR | 6.7, LR | LR | LR | LR | LR | LR |

Limited Response (LR) = % growth inhibition < 30%. Values next to tumor cell type (#) are numbers of unique cell lines tested. Data represents mean of two or three independent repeats

TABLE 8

KRAS Mutated PDX Specimen Profiles GI$_{50}$ Summary (μM)

| Patient Clinical Stage at Collection | Prior Therapy | KRAS Mutation | Specimen Type | Compound A | KO-539 | SNDX-5613 |
|---|---|---|---|---|---|---|
| BM-207 (Not Available) | N/A | G12D | Pancreatic | 0.559 | LR | LR |
| BM-206 (Not Available) | N/A | G12D | Pancreatic | 0.244 | 4.27 | LR |
| BM-204 (Stage IV) | 1) 5-FU/Oxaliplatin; 2) 5-FU/Irinotecan/Bevacizumab; 3) 5-FU/Panitumumab | G12D | CRC | 0.671 | 6.32 | LR |
| BM-205 (Stage IV) | 1) 5-FU/Oxaliplatin/Bevacizumab (mixed response) 2) Capecitabine/Irinotecan/Bevacizumab 3) Irinotecan/Cetuximab/Capecitabine (responded, progression unknown) | G12D | CRC | 0.298 | 9.98 | LR |
| BM-203 (Stage IV) | 1) 5-FU/Oxaliplatin | G12C | CRC | 0.624 | 8.23 | LR |
| BM-208 (Stage IV) | 1) Cisplatin/Etoposide (mixed response) 2) Carboplatin/Pemetrexed (mixed response) 3) Ramucirumab/Docetaxel (mixed response) | G12D | NSCLS | 0.480 | 7.39 | LR |
| BM-201 (Stage III) | 1) Carboplatin/Nab-paclitaxel; 2) Carboplatin/Docetaxel | G12C | NSCLS | 0.384 | LR | LR |
| BM-202 (Not Available) | 1) Cisplatin/Bevacizumab | G12C | NSCLS | 0.352 | 7.75 | LR |

Example B4

This example describes preclinical activity of covalent menin inhibitor, Compound A, in chronic lymphocytic leukemia (CLL).

A comprehensive panel of CLL samples isolated from patients with Rai Stages 1 to 3 disease, including relapsed or refractory disease, were cultured ex vivo in the presence of Compound A or clinical reversible menin inhibitor to assess the antileukemic activity of the compounds.

Compound A elicits >90% reduction of BCL2 transcript at twenty-four hours post treatment in MOLM-13 cells as the gene expression data is not in CLL cells. Fold change was calculated relative to vehicle control (FIG. 31). Compound A achieves >9800 cell lethality against diverse CLL ex vivo models (FIGS. 32A-32E).

Compound A demonstrated high potency, achieving >98% cell lethality at 1 μM exposure in all patient samples tested, with IC$_{50}$ values in the range of 0.1 to 0.38 μM. Specimens isolated from patients with clinical profiles containing high-risk genetic backgrounds associated with inferior outcomes to standard therapy, such as mutations in TP53 and NOTCH1, and chromosomal aberrations such as del (13q), trisomy 12 and complex karyotype, exhibited high sensitivity to Compound A treatment (Table 9).

TABLE 9

Clinical Profiles of CLL Patient Samples and Response to Compound A

| Sample | Mutation | Cytogenetics | Prior Treatment | Rai Binet Stage | Compd A IC$_{50}$ (nM) | Compd A % Max Inhibition |
|---|---|---|---|---|---|---|
| BM-301 | ATM | Normal | Bendamustine (responded, then progressed) | Stage 2 (Relapsed) | 373 | 98.7 |
| BM-302 | NOTCH1 | Normal | Ibrutinib (responded, then progressed) | Stage 2 (Relapsed) | 332 | 99.7 |
| BM-303 | TP53 | N/A | Ibrutinib (pre-collection), ibrutinib and venetoclax (responded, then progressed post-collection) | Stage 1 | 285 | 99.8 |
| BM-304 | None or N/A | *see below | Ibrutinib (responded, progression data N/A) | Stage 1 | 104 | 99.9 |
| BM-305 | WT1 | Normal | Rituximab/Ibrutinib (responded, no progression) | Stage 2 | 384 | 100 |
| BM-306 | TP53 | Normal | Ibrutinib (responded, no progression) | Stage 3 | 380 | 100 |
| BM-307 | KRAS, KMT2A, TET2 | **see below | Rituximab/Methyl prednisolone (responded, progression N/A), ibrutinib (response N/A) | N/A | 145 | 99.5 |
| BM-308 | None or N/A | *** see below | Rituximab/Ibrutinib (responded, no progression) | Stage 2 | 359 | 99 |
| BM-309 | None or N/A | Normal | Ibrutinib (responded, progression N/A) | Stage 3 | 331 | 100 |
| BM-310 | None or N/A | Normal | Ibrutinib (responded, no progression) | N/A | 357 | 99 |
| BM-311 | NOTCH1, ATM | N/A | N/A | Stage 2 (Relapsed) | 359 | 100 |
| BM-312 | None or N/A | N/A | N/A | N/A | 384 | 100 |

*44, XX, add(3)(q21), −5, add(6)(p12), +11, der(11; 13)(q10; q10), −13, t(15; 18)(q15; q21), add(16)(p13.3), add(17)(p11.2) [cp15]/46, XX [6]
**47, XY, +12, t(14; 19)(q32; q13.3), t(16; 20)(p13.3; q13.1) [13]/46, XY [7]
*** 46~47, XY, del(6)(q13q25), dic(7; 21)(q31; p13), add(11)(q13), del(13)(q12q14), +2mar, inc [cp4]/46, XY [3]

TABLE 10

Compound A Exhibits Higher Ex vivo Potency Compared to Standard-of-care Agents

| Sample | Mutation | Compound A IC$_{50}$ (µM) | Compound A % Max Inhibition | Ibrutinib IC$_{50}$ (µM) | Bendamustine IC$_{50}$ (µM) | Idelasib IC$_{50}$ (µM) |
|---|---|---|---|---|---|---|
| BM-301 | ATM | 0.373 | 98.7 | 14.8 | 15.6 | 8.91 |
| BM-302 | NOTCH1 | 0.332 | 99.7 | N/A | N/A | N/A |
| BM-303 | TP53 | 0.285 | 99.8 | 29.1 | 31.9 | 37.2 |
| BM-304 | None or N/A | 0.104 | 99.9 | N/A | N/A | N/A |
| BM-305 | WT1 | 0.384 | 100 | 34.8 | 17.1 | 35.7 |
| BM-306 | TP53 | 0.38 | 100 | 24.1 | 6.65 | 2.21 |
| BM-307 | KRAS, KMT2A, TET2 | 0.145 | 99.5 | 18.3 | 16.1 | 0.271 |
| BM-308 | None or N/A | 0.359 | 99 | 26.7 | 15.7 | 22.7 |
| BM-309 | None or N/A | 0.331 | 100 | 29.0 | 25.2 | 38.1 |

TABLE 10-continued

Compound A Exhibits Higher Ex vivo Potency Compared to Standard-of-care Agents

| Sample | Mutation | Compound A $IC_{50}$ (μM) | Compound A % Max Inhibition | Ibrutinib $IC_{50}$ (μM) | Bendamustine $IC_{50}$ (μM) | Idelasib $IC_{50}$ (μM) |
|---|---|---|---|---|---|---|
| BM-310 | None or N/A | 0.357 | 99 | 12.4 | 6.84 | 1.67 |
| BM-311 | NOTCH1, ATM | 0.359 | 100 | 29.1 | 32.2 | 35.7 |
| BM-312 | None or N/A | 0.384 | 100 | N/A | N/A | N/A |

Compound A was also highly effective against patient samples with clinical profiles of resistance to bendamustine, ibrutinib, and venetoclax therapy (FIGS. 32C-32E). Clinical reversible menin inhibitors demonstrated no significant activity across all patient samples tested, with incalculable $IC_{50}$ values and <1500 reduction in cell viability at 1 μM exposure (FIGS. 32C-32E). Collectively, the data demonstrate the potent preclinical activity of Compound A against CLL patient specimens harboring various mutational and cytogenetic backgrounds, including categories of high-risk, highlighting the unique potential of covalent menin inhibition as a novel therapeutic option for patients with CLL.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, for example, diluents, binders, lubricants, fillers, and the like.

What is claimed is:

1. A crystalline Form D of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide (Compound A) of Formula (I):

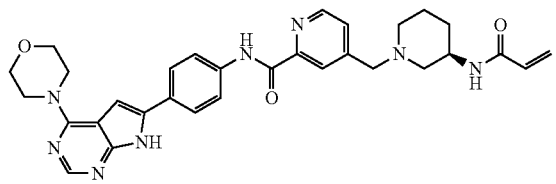

(I)

wherein the crystalline Form D is characterized by an X-ray powder diffraction pattern comprising characteristic peaks at angles (° 2θ) selected from the group consisting of 18.5°±0.1° 2θ, 19.6°±0.1° 2θ, and 24.2°±0.1° 2θ.

2. The crystalline Form D of claim 1, wherein the crystalline Form D is further characterized by an X-ray powder diffraction pattern comprising one, two, three, or four additional characteristic peaks at angles (° 2θ) selected from the group consisting of 3.4°±0.1° 2θ, 8.7°±0.1° 2θ, 10.72±0.1° 2θ, and 15.6°±0.1° 2θ.

3. The crystalline Form D of claim 1, wherein the crystalline Form D is further characterized by an X-ray powder diffraction pattern comprising four, five, or six additional characteristic peaks at angles (° 2θ) selected from the group consisting of 3.4°±0.1° 2θ, 5.3°±0.1° 2θ, 7°±0.1° 2θ, 8.7°±0.1° 2θ, 10.8°±0.1° 2θ, 12.9°±0.1° 2θ, 14.3°±0.1° 2θ, 15.6°±0.1° 2θ, and 17°±0.1° 2θ.

4. The crystalline Form D of claim 1, wherein the crystalline Form D is further characterized by an X-ray powder diffraction pattern comprising seven, eight, or nine additional characteristic peaks at angles (° 2θ) selected from the group consisting of 3.4°±0.1° 2θ, 5.3°±0.1° 2θ, 6.9°±0.1° 2θ, 7°±0.1° 2θ, 8.7°±0.1° 2θ, 10.8°±0.1° 2θ, 12.9°±0.1° 2θ, 14.3°±0.1° 2θ, 15.6°±0.1° 2θ, 17°±0.1° 2θ, and 21.5°±0.1° 2θ.

5. The crystalline Form D of claim 1, wherein the crystalline Form D is further characterized by an X-ray powder diffraction pattern as shown in FIG. 4A.

6. The crystalline Form D of claim 1, wherein the crystalline Form D is further characterized by any one of the following properties (a), (b), or (c):
   (a) the crystalline Form D has the same X-ray powder diffraction pattern post storage in an open container at 40° C. and 75% relative humidity (RH) for at least a week; or
   (b) the crystalline Form D has the same X-ray powder diffraction pattern post storage in an open container at 25° C. and 92% relative humidity (RH) for at least a week; or
   (c) the crystalline Form D has the same X-ray powder diffraction pattern post storage in a closed container at 60° C. and 75% relative humidity (RH) for at least a week.

7. The crystalline Form D of claim 1, wherein the crystalline Form D has the same X-ray powder diffraction pattern post storage in an open container at 25° C. and 92% relative humidity (RH) for at least a week.

8. The crystalline Form D of claim 1, wherein the crystalline Form D has the same X-ray powder diffraction pattern post storage in an open container at 40° C. and 75% relative humidity (RH) for at least a week.

9. The crystalline Form D of claim 1, wherein the crystalline Form D has the same X-ray powder diffraction pattern post storage in a closed container at 60° C. and 75% relative humidity (RH) for at least a week.

10. A pharmaceutical composition comprising a pharmaceutically acceptable excipient, carrier, or diluent and the crystalline Form D of claim 1.

11. A method for treating a cancer in a mammal, wherein the method comprises administering to the mammal in need thereof a therapeutically effective amount of the crystalline Form D of claim 1.

12. The method of claim 11, wherein the cancer is a leukemia.

13. The method of claim 11, wherein the cancer is acute myeloid leukemia (AML) or acute lymphoblastic leukemia (ALL).

14. The method of claim 11, wherein the crystalline Form D of N-[4-[4-(4-morpholinyl)-7H-pyrrolo[2,3-d]pyrimidin-6-yl]phenyl]-4-[[3(R)-[(1-oxo-2-propen-1-yl)amino]-1-piperidinyl]methyl]-2-pyridinecarboxamide is administered to the mammal in need thereof in a therapeutically effective amount selected from the group consisting of 25 mg, 50 mg, 75 mg, 100 mg, 125 mg, 150 mg, 175 mg, 200 mg, 325 mg, 500 mg, and 650 mg.

15. A method for treating a KRAS mutation cancer in a mammal, wherein the method comprises administering to the mammal in need thereof a therapeutically effective amount of the crystalline Form D of claim 1.

16. The method of claim 15, wherein the cancer is a solid tumor.

17. A method for treating diffuse large B-cell lymphoma or multiple myeloma in a mammal, wherein the method comprises administering to the mammal in need thereof a therapeutically effective amount of the crystalline Form D of claim 1.

18. A process for preparing crystalline Form D of N-[4-[4-(4-morpholinyl)-7H-pyrrolo[2,3-d]pyrimidin-6-yl]phenyl]-4-[[3(R)-[(1-oxo-2-propen-1-yl)aminol-1-piperidinyl]methyl]-2-pyridinecarboxamide (Compound A) of the Formula (I) according to claim 1:

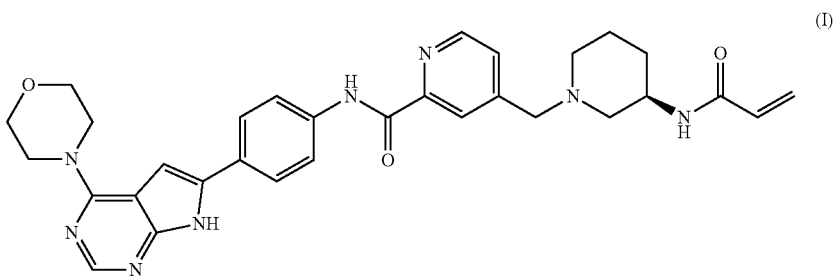 [SMILES: C=CC(=O)N[C@@H]1CCCN(Cc2ccnc(C(=O)Nc3ccc(-c4cc5c(N6CCOCC6)ncnc5[nH]4)cc3)c2)C1]

(I)

wherein the crystalline Form D is characterized by an X-ray diffraction pattern comprising characteristic peaks at angles (° 2θ) selected from the group consisting of 18.5°±0.1° 2θ, 19.6°±0.1° 2θ, and 24.2°±0.1° 2θ; and wherein the process comprises the following steps:
(1) adding N-[4-[4-(4-morpholinyl)-7H-pyrrolo[2,3-d]pyrimidin-6-yl]phenyl]-4-[[3(R)-[(1-oxo-2-propen-1-yl)aminol-1-piperidinyl]methyl]-2-pyridinecarboxamide (Compound A) of Formula (I):

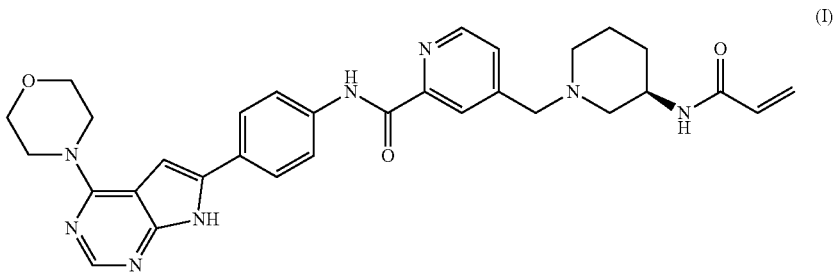 [SMILES: C=CC(=O)N[C@@H]1CCCN(Cc2ccnc(C(=O)Nc3ccc(-c4cc5c(N6CCOCC6)ncnc5[nH]4)cc3)c2)C1]

(I)

to a vial containing a tetrahydrofuran:water mixture, to form a suspension;
(2) slurrying the suspension formed in step (1) above at 50° C. for four days with protection from light;
(3) filtering the suspension formed in step (3) above, to obtain a wet cake containing crystalline Form D of N-[4-[4-(4-morpholinyl)-7H-pyrrolo[2,3-d]pyrimidin-6-yl]phenyl]-4-[[3(R)-[(1-oxo-2-propen-1-yl)aminol-1-piperidinyl]methyl]-2-pyridinecarboxamide (Compound A) of Formula (I) above; and
(4) drying the wet cake obtained in step (3) above at 50° C. under vacuum for three hours, to obtain crystalline Form D of N-[4-[4-(4-morpholinyl)-7H-pyrrolo[2,3-d]pyrimidin-6-yl]phenyl]-4-[[3(R)-[(1-oxo-2-propen-1-yl)aminol-1-piperidinyl]methyl]-2-pyridinecarboxamide (Compound A) of Formula (I) above.

19. The process of claim 18, wherein the tetrahydrofuran:water mixture is an 80:20 v/v tetrahydrofuran:water mixture.

* * * * *